(12) United States Patent
Béliveau et al.

(10) Patent No.: US 7,919,103 B2
(45) Date of Patent: Apr. 5, 2011

(54) COMPOUND AND METHOD FOR REGULATING PLASMINOGEN ACTIVATION AND CELL MIGRATION

(75) Inventors: Richard Béliveau, Montreal (CA); Michel Demeule, Longueuil (CA); Yanick Bertrand, Longueuil (CA); Jonathan Michaud-Levesque, Montreal (CA); Yannève Rolland, Montreal (CA); Julie Jodoin, Montreal (CA)

(73) Assignee: Transfert Plus, Montreal (CA)

( * ) Notice: Subject to any disclaimer, the term of this patent is extended or adjusted under 35 U.S.C. 154(b) by 0 days.

(21) Appl. No.: 10/556,145

(22) PCT Filed: May 7, 2004

(86) PCT No.: PCT/CA2004/000697
§ 371 (c)(1),
(2), (4) Date: Aug. 21, 2006

(87) PCT Pub. No.: WO2004/099410
PCT Pub. Date: Nov. 18, 2004

(65) Prior Publication Data
US 2007/0053894 A1    Mar. 8, 2007

Related U.S. Application Data

(60) Provisional application No. 60/469,000, filed on May 9, 2003.

(51) Int. Cl.
*A61K 39/00* (2006.01)
*A61K 39/38* (2006.01)
(52) U.S. Cl. .................................. 424/198.1; 424/184.1
(58) Field of Classification Search ........................ None
See application file for complete search history.

(56) References Cited

U.S. PATENT DOCUMENTS 6,455,494 B1 * 9/2002 Jefferies et al. .................. 514/2
2002/0119095 A1 * 8/2002 Gabathuler et al. ......... 424/1.49

OTHER PUBLICATIONS

Freshney, R.I. Culture of Animal Cells, A Manual of Basic Technique, Alan R. Liss, Inc. 1983, New York, p. 4.*
Dermer, G.B. Another anniversary for the war on cancer. Bio/technology, 1994. vol. 12, p. 320.*
MSNBC News Services, Nov. 9, 2000. Mixed results on new cancer drug.*
Gura, T. Systems for identifying new drugs are often faulty. Science, 1997. vol. 278, pp. 1041-1042.*
Sala, Roberta et al., European Journal of Cell Biology, vol. 81, No. 11, Nov. 2002, pp. 599-607.
Demeule, Michel et al., Blood, vol. 102, No. 5, Sep. 1, 2003, pp. 1723-1731.
Rose, T.M. et al., Proceedings of the National Academy of Sciences of USA, National Academy of Science. vol. 83, Mar. 1986, pp. 1261-1265.
Schlingemann, R.O. et al., American Journal of Pathology, vol. 136, No. 6, 1990, pp. 1393-1406.
Alemany et al., 1993, J Cell Sci, 104:1155-1162.
Andreasen et al., 1997, Int. J Cancer, 72:1-22.
Baker et al., 1992, FEBS Letters, 298(2,3):215-218.
Bass et al., 2002, J Biol Chem, 277(49):46845-46848.
Brown et al., 1981, Proc Natl Acad Sci USA, 78(1):539-543.
Brown et al., 1982, Nature, 296:171-173.
Bu et al., 1996, J Biol Chem, 271(36):22218-22224.
Conese et al., 1995, J Cell Biol, 131(6):1609-1622.
Cubellis et al., 1989, Proc Natl Acad Sci USA, 86:4828-4832.
Dano et al., 1985, Adv Cancer Res, 44:139-266.
Dehouck et al., 1992, J Neurochem, 58 (5):1790-1797.
Demeule, et al., 2002 J Neurochem 83:924-933.
Fillebeen et al., 1999 J Biol Chem 274(11):7011-7017.
Food et al., 1994 J Biol Chem. 269(4):3034-3040.
Gong et al., 2001 J Biol Chem 276(22):19078-19083.
Herz et al., 2001J Clin Invest 108(6):779-784.
Jefferies et al., 1996 Brain Res 712:122-126.
Johnsson et al., 1991 Anal Biochem 198:268-277.
Kennard et al., 1996 Nat Med 2:1230-1235.
Kozyraki et al., 2001 Proc Natl Acad Sci USA 98(22):12491-12496.
Li et al., 2002 J Biol Chem 277(44):42366-42371.
Liu et al., 2002 J. Biol Chem 276(31):28889-28896.
Min et al., 1996 Cancer Res 56:2428-2433.
Neels et al., 1999 J Biol Chem 274(44):31305-31311.
Nielsen et al., 1988 J. Biol Chem 263(5):2358-2363.
Nykjaer et al., 1997 EMBO J 16(10):2610-2620.
Olson et al., 1992 J Biol Chem 267(13):9129-9133.
Ploug et al., 1991 J Biol Chem 266(3):1926-1933.
Reijerkerk et al., 2000 Eur J Cancer, 36:1695-1705.
Richardson, 2000 Eur J. Biochem 267:1290-1298.
Sekyere et al., 2000 FEBS Letters 483:11-16.
Stahl et al., 1997 Int J Cancer 71:116-122.
Tarui et al., 2002 J Biol Chem 277(37):33564-33570.
Weaver et al., 1997 J Biol Chem 272(22):14372-14379.
Woodbury et al., 1980 Proc Natl Acad Sci USA 77(4):2183-2187.
Woodbury et al., 1981, Int J Cancer, 27:145-149.
Richardson, et al., "The role of the membrane-bound tumour antigent, melanotransferrin (p97), in iron uptake by the human malignant melanoma cell," Eur.J.Biochem., vol. 267, pp. 1290-1298 (2000).

(Continued)

*Primary Examiner* — Anne M. Gussow
(74) *Attorney, Agent, or Firm* — Birch, Stewart, Kolasch & Birch, LLP

(57) ABSTRACT

The invention relates to novel regulators of plasminogen activation and their use for regulating cell migration, plasminolysis, angiogenesis, fibrinolysis, for treating cancer and thrombo-embolic diseases such as heart stroke. Furthermore, the present invention relates to novel pharmaceutical compositions form regulating cell migration, plasminolysis, angiogenesis and for treating cancer. In particular, the present invention relates to a method of regulating the activation of plasminogen comprising contacting a solution of pro-urokinase (uPA) or tissue plasminogen activator (tPA) and plasminogen with melanotransferrin (p97) for a time sufficient to effect regulation thereof.

7 Claims, 33 Drawing Sheets

OTHER PUBLICATIONS

Sekyere, et al., "Examination of the distribution of the transferrin homologue, melanotransferrin (tumour antigen p97), in mouse and human," Biochimica, vol. 1722, pp. 131-142 (2005).

Dunn, et al., "The function of melanotransferrin: a role in melanoma cell proliferation and tumorigenesis," Carcinogenesis, vol. 27, No. 11, pp. 2157-2169 (2006).

Rahmanto, et al., "Identification of distinct changes in gene expression after modulation of melanoma tumor antigen p97 (melanotransferrin) in multiple models in vitro and in vivo," Carcinogenesis, vol. 28, No. 10, pp. 2172-2183 (2007).

Sekyere, et al., "Role of melanotransferrin in iron metabolism: studies using targeted gene disruption in vivo," Blood, vol. 107, pp. 2599-2601 (2006).

* cited by examiner

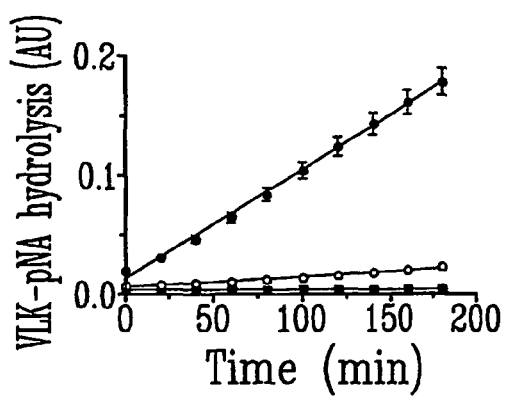 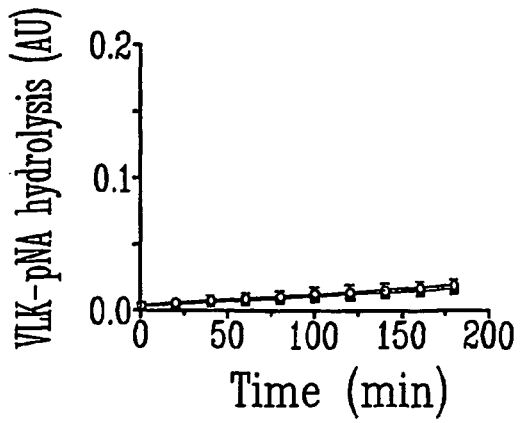
*Fig-4A*  *Fig-4B*
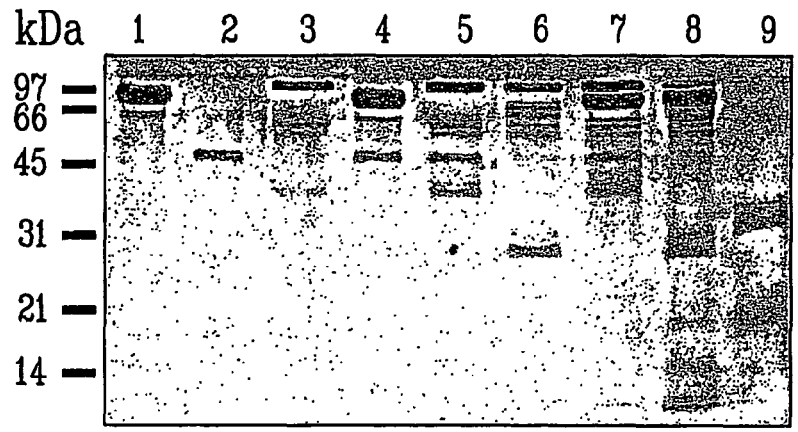
*Fig-4C*
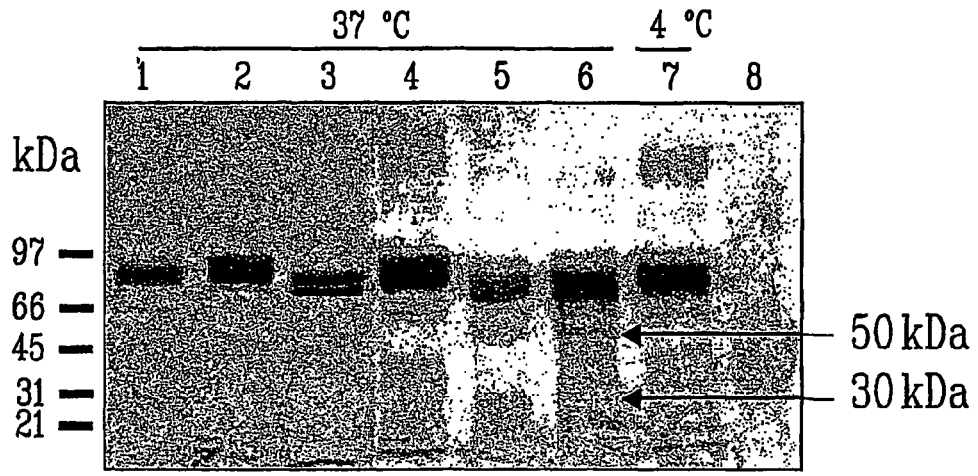
*Fig-4D*

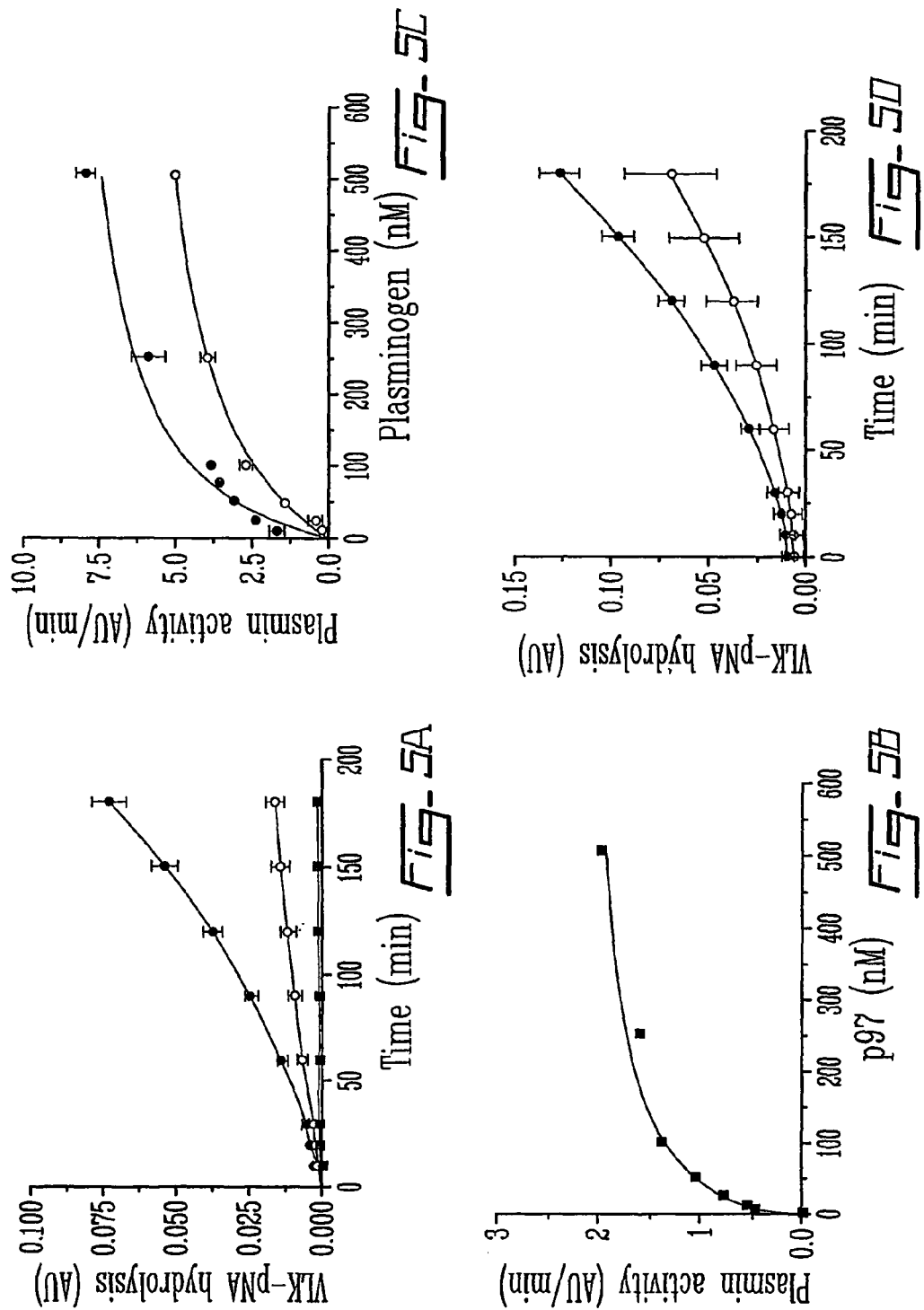

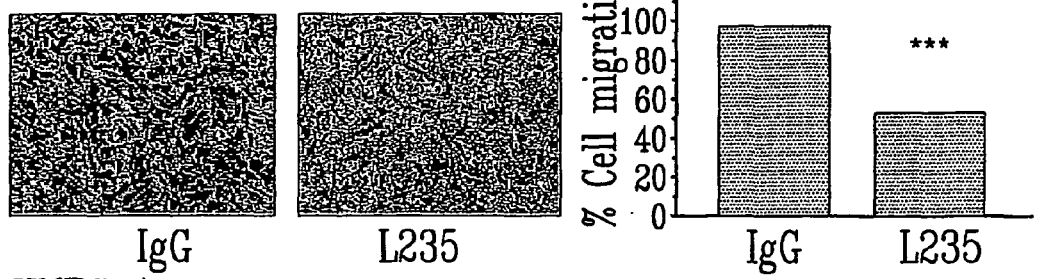
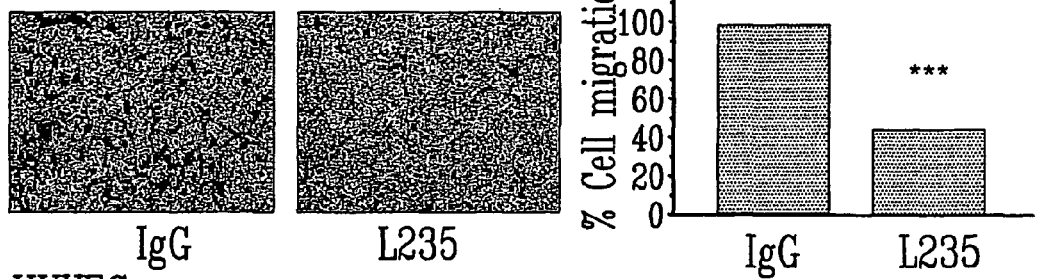
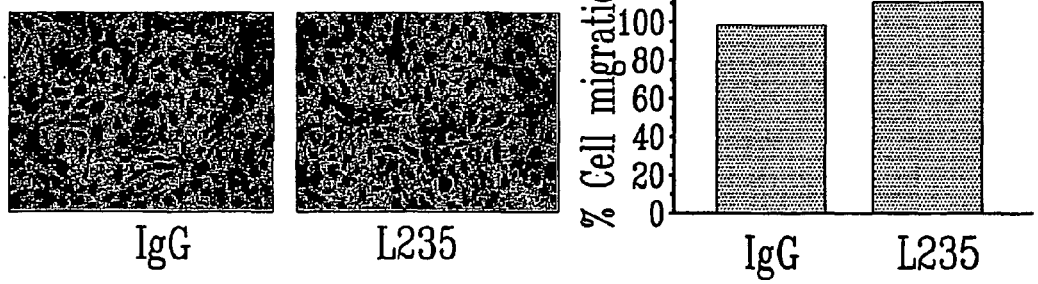
FIG-6A
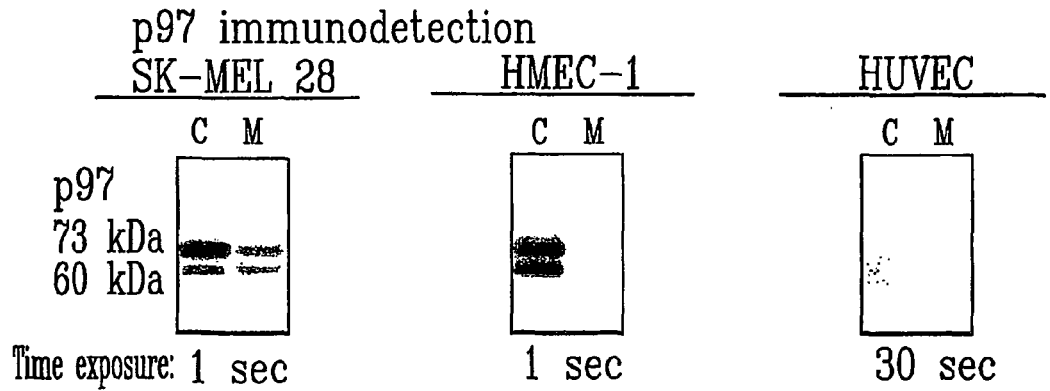
FIG-6B

HMEC-1
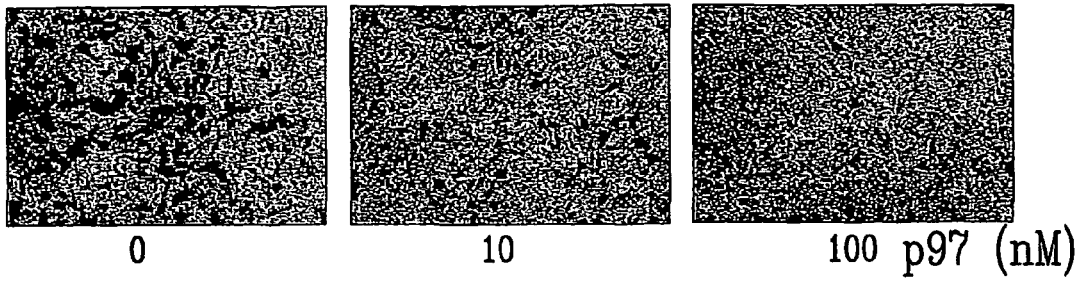
*Fig-7A*
SK-MEL 28
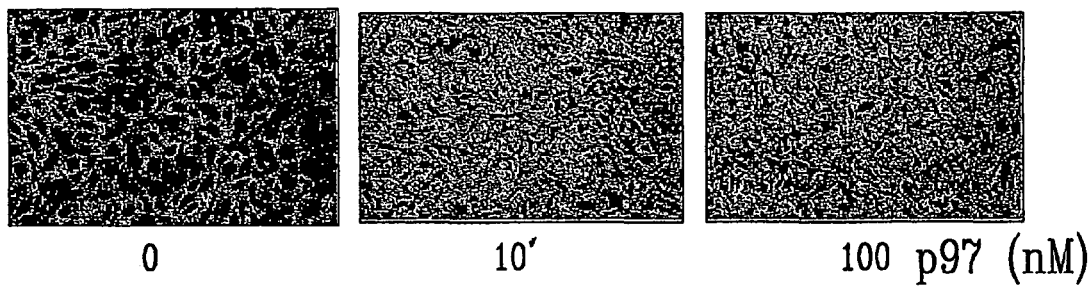
*Fig-7B*
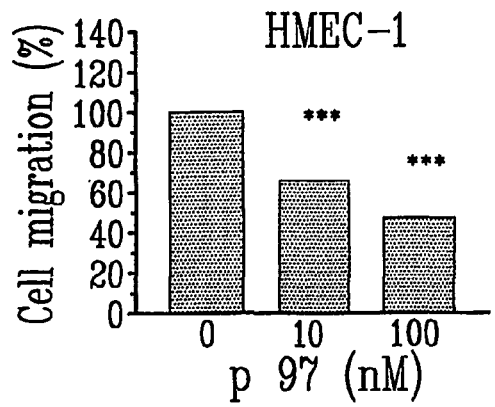 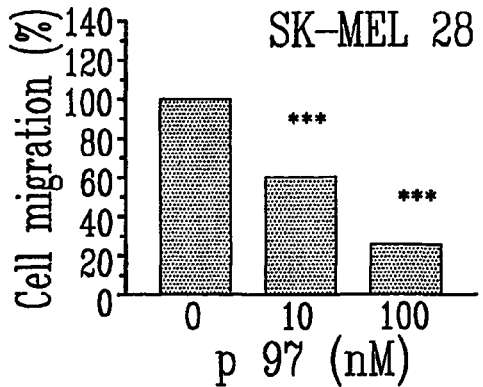
*Fig-7C*

HMEC-1

HMEC-1

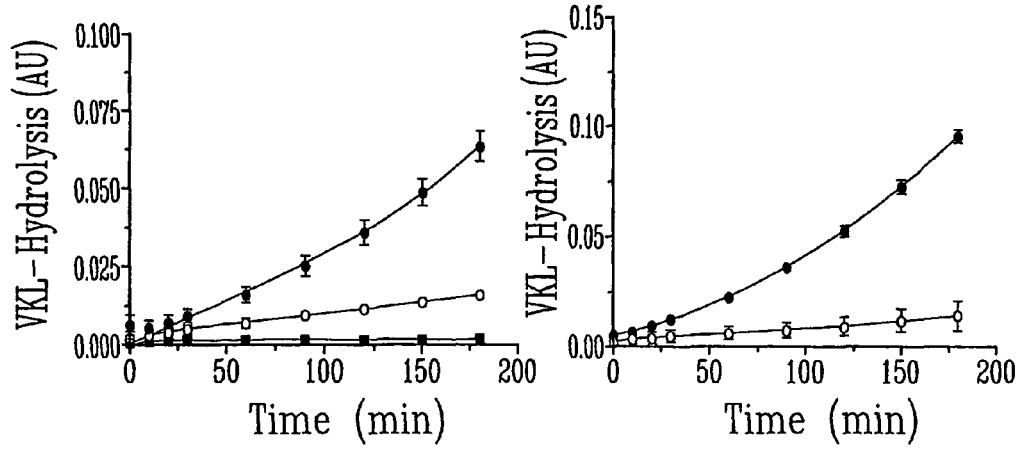
*Fig-23A*   *Fig-23B*
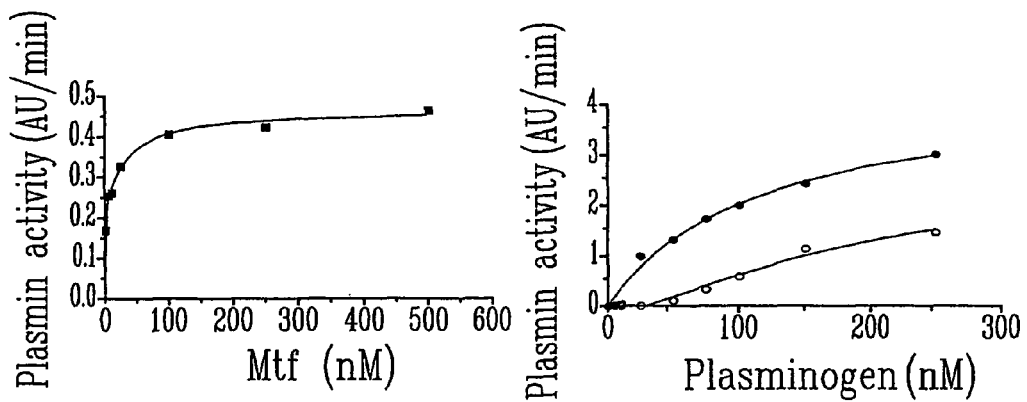
*Fig-23C*   *Fig-23D*

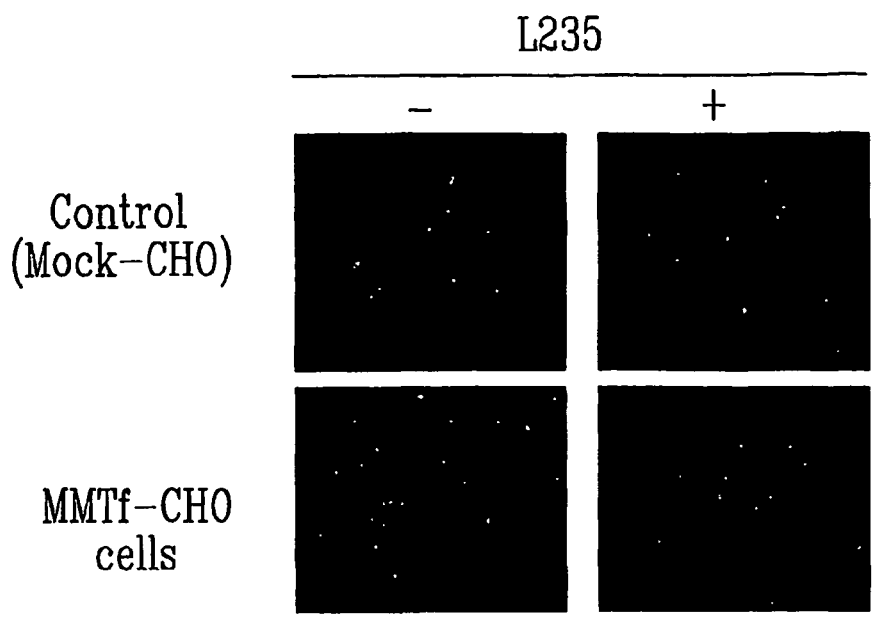
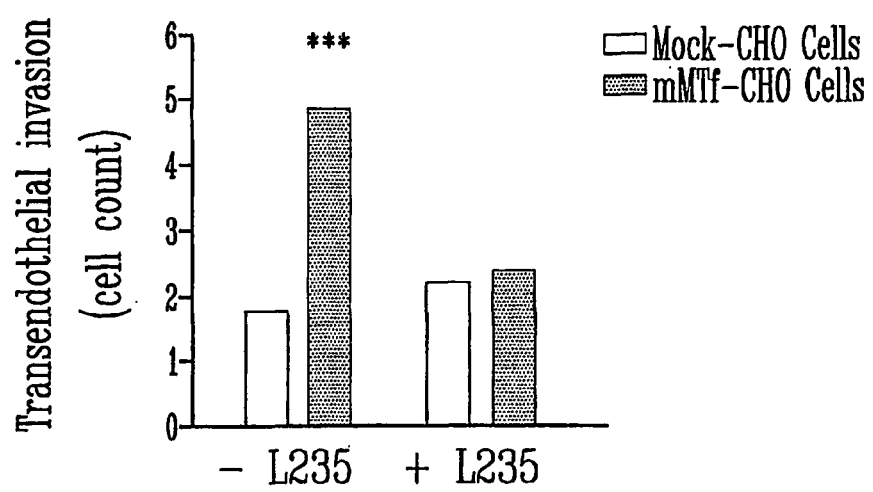
Fig-28

Pro-uPA and plasminogen interaction with soluble p97

Inhibition by mAb L235

Competition of exogenous p97 for pro-uPA and plasminogen interaction

COMPOUND AND METHOD FOR REGULATING PLASMINOGEN ACTIVATION AND CELL MIGRATION

This National Phase PCT application claims priority under 35 U.S.C. 119(e) on U.S. Provisional Application No. 60/469,000 filed on May 9, 2003 of which is hereby incorporated by reference.

BACKGROUND OF THE INVENTION (a) Field of the Invention

The invention relates to novel regulators of plasminogen activation and their use for regulating cell migration and treating cancer. Furthermore, the present invention relates to novel pharmaceutical compositions form regulating cell migration and treating cancer.

(b) Description of the Prior Art

Melanotransferrin (p97) possesses a high level of homology (37-39%) with human serum transferrin, human lactoferrin and chicken transferrin. It is a glycosylated protein that reversibly binds iron and was first found at high levels in malignant melanoma cells. Two forms of p97 have been reported, one of which is bound to cell membranes by a glycosylphosphatidylinositol anchor while the other form is both soluble and actively secreted. The exact physiological role of either membrane-bound p97 or secreted p97 is largely unexplored.

In the early 1980s, p97 was found to be expressed in much larger amounts in neoplastic cells and fetal tissues than in normal tissues. More recently, it was reported that p97 mRNA is widespread in normal human tissues. p97 is also expressed in reactive microglia associated with amyloid plaques in Alzheimers disease. Normal serum contains very low levels of p97, which were reported to increase by 5- to 6-fold in patients with Alzheimer's disease.

It was previously demonstrated that recombinant human melanotransferrin (p97) is transported at high rate into the brain using both an in vitro model of the blood brain barrier (BBB) and in situ mouse brain perfusion (Demeule M, et al., 2002 J Neurochem 83:924-933). It was also shown that p97 transcytosis might involve the low-density lipoprotein related protein (LRP). This receptor is also known to mediate the internalization of the urokinase:plasminogen activator inhibitor:urokinase receptor complex (uPA:PAI-1:uPAR). Briefly, single-chain proenzyme-uPA is activated upon binding to its cell surface receptor uPAR; which is a glycosylphosphatidylinositol (GPI)-anchored membrane protein. After its activation, uPA (which catalyzes the conversion of plasminogen to plasmin) is quickly inhibited by the plasminogen activator inhibitor type-1 (PAI-1). The inactive uPA:PAI-1 complex binds to uPAR and then is rapidly internalized by LRP. The uPA:PAI-1 complex is degraded in lysosomes whereas the uPAR is recycled at the cell surface. Other LRP ligands include pro-uPA, PAI-1, receptor-associated protein (RAP) and a diverse spectrum of structurally unrelated proteins.

Heart disease has topped the list of killer diseases every year but one since 1900. (The exception was 1918, when an influenza epidemic killed more than 450,000 Americans.) Stroke is the third leading cause of death in the United States, following cancer. Much of the progress is due to the development of effective medicines to control blood pressure and cholesterol, according to officials of the National Heart, Lung and Blood Institute. But, experts warn, the war against heart disease and stroke is not yet won. Every 33 seconds, an American dies of either heart disease or stroke. Nearly 62 million Americans have one or more types of cardiovascular disease, and these diseases cost our society more than $350 billion a year.

Two strategies are presently used to restore the flow after thrombosis: 1) clot dissolution with administration of plasminogen activators and 2) clot permeation by surgical intervention. The tissue-type plasminogen activator (tPA) and its conventional substrate plasminogen, are key players involve in fibrinolysis. Currently, tPA is used as a stroke therapy, however, its associated adverse effects might limit its efficiency.

It would be highly desirable to be provided with novel regulators of plasminogen activation and their use for regulating cell migration and treating cancer.

It would also be highly desirable to be provided with novel pharmaceutical compositions form regulating cell migration and treating cancer.

It would be highly desirable to be provided with a new treatment for thromboembolic disorders such as venous or arterial thrombosis, thrombophlebitis, pulmonary and cerebral embolism, thrombotic microangiopathy and intravascular clotting. Some of these disorders will lead for example in heart and cerebral strokes.

It would be also desirable to be provided with a new method for increasing fibrinolysis or for preventing angiogenesis.

SUMMARY OF THE INVENTION

One aim of the present invention is to provide novel regulators of plasminogen activation and their use for regulating cell migration and treating cancer.

Another aim of the present invention is to provide novel pharmaceutical compositions form regulating cell migration and treating cancer.

A further aim of the present invention is to provide a new treatment for thromboembolic disorders such as, for example, without limitation, venous or arterial thrombosis, thrombophlebitis, pulmonary or cerebral embolism, thrombotic microangiopathy or intravascular clotting, some of which will lead for example in heart or cerebral strokes.

An additional aim of the present invention is to provide a new method for increasing fibrinolysis or for preventing angiogenesis.

In accordance with one embodiment of the present invention there is provided a method for increasing fibrinolysis, said method comprising contacting a solution containing pro-uroquinase plasminogen activator (pro-uPA) with melanotransferrin (p97) or an enzymatically active fragment thereof for a time sufficient to cause increased fibrinolysis.

In a preferred embodiment, p97 increase plasminogen activation through tissue plasminogen activator (t-PA).

In accordance with another embodiment of the present invention there is provided a method for inhibiting plasminogen activation, said method comprising the step of contacting pro-uroquinase plasminogen activator (pro-uPA) with membrane bound melanotransferrin (p97) for a time sufficient to prevent plasminogen activation.

In accordance with a further embodiment of the invention, there is provided a method for preventing cell migration, said method comprising the step of contacting a cell expressing melanotransferrin (p97) on its surface with exogenous soluble 97 or an antibody, or an antigen binding fragment thereof, directed to said p97 expressed on the surface of said cell, said soluble p97 competing with the p97 expressed on the cell surface, activating plasminogen in solution instead of membrane-bound plasminogen, thus preventing cell migration, said antibody, or active fragment thereof binding p97 on the surface of the cell thus preventing activation of membrane-bound plasminogen, preventing cell migration.

In a preferred embodiment of the invention, the antibody is a monoclonal antibody, and more preferably one of L235, HybC, HybE, HybF, 9B6 or 2C7.

The cell can be for example, without limitation, an endothelial cell or a tumor cell, such as one selected from the group consisting of human microvascular endothelial cells (HMEC-1) and human melanoma SK-MEL28 cells.

Still in accordance with the present invention, there is provided a method for treating cancer caused by cells expressing melanotransferrin (p97) at their surface, said method comprising the step of administering to a patient in need thereof exogenous soluble p97 or an antibody an antibody, or active fragment thereof, directed to said p97 expressed on the surface of said cell, said soluble p97 competing with the p97 expressed on the cell surface, activating plasminogen in solution instead of membrane-bound plasminogen, thus preventing cell migration, said antibody, or active fragment thereof binding p97 on the surface of the cell thus preventing activation of membrane-bound plasminogen, preventing cell migration, preventing cancer cells from spreading.

Further in accordance with the present invention, there is provided a method for regulating capillary tube formation, said method comprising the step administering to a patient in need thereof soluble 97, wherein said soluble p97 prevents or reduces capillary tube formation.

Also in accordance with the present invention, there is provided a pharmaceutical composition for use in regulating activation of plasminogen, said composition comprising a therapeutically effective amount of melanotransferrin (p97) or an enzymatically active fragment thereof in association with a pharmaceutically acceptable carrier.

Preferably, p97 is soluble p97 for increasing activation of plasminogen.

In accordance with the present invention there is also provided a method of regulating the activation of plasminogen, comprising administering to an individual in need thereof a therapeutically effective amount of the aforementioned pharmaceutical composition.

In accordance with the present invention there is also provided a pharmaceutical composition for use in regulating cell migration of a cell showing p97 activity, comprising a therapeutically effective amount of one of p97, an enzymatically active fragment thereof, or an antibody recognizing specifically p97, or an antigen binding fragment thereof, in association with a pharmaceutically acceptable carrier.

Further in accordance with the present invention there is also provided a method of regulating cell migration of a cell showing p97 activity, comprising administering to an individual in need thereof a therapeutically effective amount of the aforementioned pharmaceutical composition.

In accordance with the present invention there is further provided a pharmaceutical composition for treating cancer comprising a therapeutically effective amount of one of melanotransferrin (p97), an enzymatically active fragment thereof, or an antibody recognizing specifically p97, or an antigen binding fragment thereof, in association with a pharmaceutically acceptable carrier.

Also in accordance with the present invention there is further provided a method of treating cancer, comprising administering to an individual a therapeutically effective amount of the aforementioned pharmaceutical composition.

The cancer can be, for example, without limitation, selected from the group consisting of melanoma, prostate cancer, leukemia, hormone dependent cancer, breast cancer, colon cancer, lung cancer, skin cancer, ovarian cancer, pancreatic cancer, bone cancer, liver cancer, biliary cancer, urinary organ cancer (for example, bladder, testis), lymphoma, retinoblastoma, sarcoma, epidermal cancer, liver cancer, esophageal cancer, stomach cancer, cancer of the brain and cancer of the kidney.

In accordance with the present invention there is also provided a pharmaceutical composition for use in regulating angiogenesis comprising a therapeutically effective amount of melanotransferrin (p97) or an enzymatically active fragment thereof in association with a pharmaceutically acceptable carrier.

Still in accordance with the present invention there is also provided a method of regulating angiogenesis, comprising administering to an individual a pharmaceutically effective amount of the aforementioned pharmaceutical composition.

In accordance with the present invention, there is provided the use of p97, or an enzymatically active fragment thereof, or of any of the aforementioned composition for the various uses described herein or for the manufacture of medication for the various use described herein.

For the purpose of the present invention the following terms are defined below.

The term "p97" is also referred to in the present invention as Melanotransferrin, MTf, or P97. All of these terms are being used interchangeably. The term soluble p97 thus make reference to soluble p97 or soluble melanotransferrin.

The term "cancer" is intended to mean any cellular malignancy whose unique trait is the loss of normal controls which results in unregulated growth, lack of differentiation and ability to invade local tissues and metastasize. Cancer can develop in any tissue of any organ. More specifically, cancer is intended to include, without limitation, melanoma, prostate cancer, leukemia, hormone dependent cancers, breast cancer, colon cancer, lung cancer, skin cancer, ovarian cancer, pancreatic cancer, bone cancer, liver cancer, biliary cancer, urinary organ cancers (for example, bladder, testis), lymphomas, retinoblastomas, sarcomas, epidermal cancer, liver cancer, esophageal cancer, stomach cancer, cancer of the brain and cancer of the kidney cancer is also intended to include, without limitation, metastasis, whether cerebral, pulmonary or bone metastasis, from various types of cancers, such as melanomas, or from any types of cancer mentioned above.

The terms "treatment", "treating" and the like are intended to mean obtaining a desired pharmacologic and/or physiologic effect, e.g., inhibition of cancer cell growth. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) inhibiting the disease, (e.g., arresting its development); or (B) relieving the disease (e.g., reducing symptoms associated with the disease).

The term "administering" and "administration" is intended to mean a mode of delivery including, without limitation, oral, rectal, parenteral, subcutaneous, intravenous, intramuscular, intraperitoneal, intraarterial, transdermally or via a mucus membrane. The preferred one being orally. One skilled in the art recognizes that suitable forms of oral formulation include, but are not limited to, a tablet, a pill, a capsule, a lozenge, a powder, a sustained release tablet, a liquid, a liquid suspension, a gel, a syrup, a slurry, a suspension, and the like. For example, a daily dosage can be divided into one, two or more doses in a suitable form to be administered at one, two or more times throughout a time period.

The term "therapeutically effective" is intended to mean an amount of a compound sufficient to substantially improve some symptom associated with a disease or a medical condition. For example, in the treatment of cancer, a compound which decreases, prevents, delays, suppresses, or arrests any symptom of the disease would be therapeutically effective. A therapeutically effective amount of a compound is not required to cure a disease but will provide a treatment for a disease such that the onset of the disease is delayed, hindered, or prevented, or the disease symptoms are ameliorated, or the term of the disease is changed or, for example, is less severe or recovery is accelerated in an individual.

The compounds of the present invention may be used in combination with either conventional methods of treatment and/or therapy or may be used separately from conventional methods of treatment and/or therapy.

When the compounds of this invention are administered in combination therapies with other agents, they may be administered sequentially or concurrently to an individual. Alternatively, pharmaceutical compositions according to the present invention may be comprised of a combination of a compound of the present invention, as described herein, and another therapeutic or prophylactic agent known in the art.

It will be understood that a specific "effective amount" for any particular individual will depend upon a variety of factors including the activity of the specific compound employed, the age, body weight, general health, sex, and/or diet of the individual, time of administration, route of administration, rate of excretion, drug combination and the severity of the particular disease undergoing prevention or therapy.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include citric acid, lactic acid, tartaric acid, fatty acids, and the like.

As used herein, "pharmaceutically acceptable carrier" includes any and all solvents (such as phosphate buffered saline buffers, water, saline), dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients can also be incorporated into the compositions.

BRIEF DESCRIPTION OF THE DRAWINGS

FIG. 4 illustrates the effects of p97 on pro-uPA, tPA and plasminogen and shows that (A) VLK-pNA hydrolysis by pro-uPA increases when p97 is added to the reaction; (B) p97 elicits no observable effect on tPA; (C) the interaction of p97 with pro-uPA does not result in the cleavage of either protein; and (D) p97 alters the cleavage of glu-plasminogen by pro-uPA;

FIG. 5 illustrates plasminogen activation by p97 and shows that (A) VLK-pNA hydrolysis is 4-fold higher when p97 is added to pro-uPA and plasminogen; (B) p97 stimulates plasminogen cleavage by pro-uPA in a dose-dependent manner; (C) p97 positively affects the activation of plasminogen by pro-uPA by increasing the catalytic efficiency of pro-uPA; and (D) the effect of p97 upon pro-uPA's activation of plasminogen is specific and involves the epitope recognized by the mAb L235;

FIG. 6 illustrates the inhibition of cell migration by mAb L235, an antibody to p97, and shows that (A) the presence of mAb L235, inhibits the migration of HMEC-1 and SK-MEL28 cells but not HUVEC cells; and (B) p97 is highly expressed in lysates from HMEC-1 and SK-MEL29 cells and at lower levels in their respective conditioned culture media, but is almost undetectable in HUVEC cells;

FIG. 7 illustrates that (A) exogenous p97 inhibits the migration of MHEC-1 cells and (B) SK-MEL28 cells; and (C) the level of inhibition is 50% and 70%, respectively at 100 nM p97 for those same cells respectively;

FIG. 23 illustrates the effects of p97 interaction with plasminogen (Plg) on tPA-dependant plasmin activity, and more specifically demonstrates that the presence of p97 increases the plasminogen activation (23A), that the induction caused by p97 of the plasminogen activity is inhibited by the monoclonal antibody directed against p97 (23B), the plasminolytic activity of tPA in the presence of p97 (23C), and that soluble p97 decreases the apparent $K_m$ of tPA for plasminogen (23D);

FIG. 28 illustrates transendothelial invasion across the blood-brain barrier of CHO cells transfected with (mMTf-CHO cells) or without (Mock-CHO cells) membrane bound p97.

DETAILED DESCRIPTION OF THE INVENTION

Materials and Methods

Figure 1A:
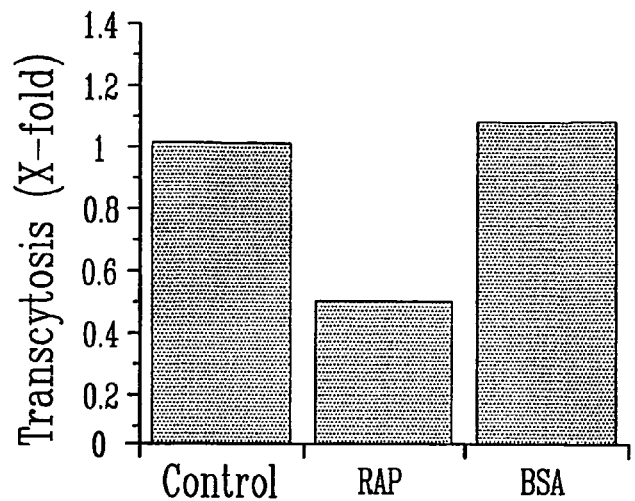
FIG. 1A-1B illustrates that (1A) a significant (>50%) reduction in the transport of [125I]-p97 (25 nM) from the apical (blood side) to the basolateral side (brain side) of bovine brain capillary endothelial cell (BBCEC) monolayers is observed in the presence of 640 nM receptor-associated protein (RAP) and that (1B) no interactions are observed between RAP and BSA proteins and p97, suggesting that the inhibition of [$^{125}$I]-p97 transcytosis is not related to protein interactions between p97 and RAP.

Soluble human recombinant p97 which is produced by introducing a stop codon following the glycine residue at position #711 (of SEQ ID NO:1) and monoclonal antibodies (mAbs) directed against p97 were kindly provided by Biomarin Pharmaceutical Inc. (Novato, Calif.). TPA, PAI-1 and plasmin are from Calbiochem (La Jolla, Calif.). Pro-uPA and plasminogen are from American Diagnostica (Greenwich, Conn.). Angiostatin is purchased from Angiogenesis Laboratories (Tucson, Ariz.) whereas uPA is from Roche Biochemicals (Laval, QC). CM5 sensor chips are from BIAcore (Piscataway, N.J.). The plasmin substrate (D-val-leu-lys-p-nitraniline or VLK-pNA) and other biochemical reagents are from Sigma (Oakville, ON).

Antibodies directed against α-LRP (8G1 clone) and u-PAR (#3937) were from Research Diagnostics Inc. (Flanders, N.J.) and American Diagnostica (Greenwich, Conn.), respectively. Antibodies directed against Cav-1 (#C3721) and phosphorylated Cav-1 (pCav-1) (#61438) were from BD Transduction Laboratories (Lexington, Ky.). The antibody directed against eNOS (#N30020) was from BD Biosciences (Mississauga, ON) and the antibody directed against GAPDH (#RGM2) was from Advanced Immunochemical Inc. (Long Beach, Calif.). Antibodies directed against extracellular signal-regulated kinase 1/2 (ERK 1/2) (#9102) and pERK 1/2 (#9101S) were from Cell Signaling Technology (Beverly, Mass.). Other biochemical reagents were from Sigma (Oakville, ON).

Blood-Brain Barrier Model and Transcytosis Experiments

The in vitro model of the blood-brain barrier (BBB) is established by using a co-culture of bovine brain capillary endothelial cells (BBCEC) and newborn rat astrocytes as previously mentioned (Demeule et al., *Journal of Neurochemistry*, 83: 924-933, 2002). p97 is radioiodinated with standard procedures using an iodo-beads kit and D-Salt Dextran desalting columns from Pierce, as previously described (Demeule M, et al., 2002 J Neurochem 83:924-933). Transcytosis experiments are performed as follows: one insert covered with BBCECs is set into a six-well microplate with 2 ml of Ringer-Hepes and is pre-incubated for 2 h at 37° C. [$^{125}$I]-p97 (0.5-1.5 μCi/assay), at a final concentration of 25 nM, is then added to the upper side of the insert. At various times, the insert is sequentially transferred into a fresh well to avoid possible reendocytosis of p97 by the abluminal side of the BBCECs. At the end of the experiment, [$^{125}$I]-p97 is assayed in 500 μl of the lower chamber of each well following TCA precipitation.

Cell Culture

Cells are cultured under 5% $CO_2$/95% air atmosphere. Human microvascular endothelial cells (HMEC-1) are from the Center for Disease Control and Prevention (Atlanta, Ga.) and are cultured in MCDB 131 media (Sigma) supplemented with 10 mM L-glutamine, 10 ng/ml epidermal growth factor (EGF), 1 μg/ml hydrocortisone and 10% inactivated foetal bovine serum (FBS). Human umbilical vein endothelial cells (HUVEC) and SK-MEL28 are obtained from ATCC (Manasas, Va.). HUVECs are cultured in EGM-2 medium (bullet kit, Clonetics #CC-3162) and supplemented with 20% FBS. Melanoma SK-MEL28 cells are grown in MEM supplemented with 1 mM Na-pyruvate, 100 U/ml penicillin-streptomycin, 1.5 g/L Na-bicarbonate and 10% FBS.

BIAcore Analysis p97, PAI-1 and plasminogen are covalently coupled to a CM5 sensor chip via primary amine groups using the N-hydroxysuccinimide (NHS)/N-ethyl-N'-(dimethylaminopropyl)carbodiimide (EDC) coupling agents. Briefly, the carboxymethylated dextran is first activated with 50 μl of NHS/EDC (50 mM/200 mM) at a flow rate of 5 μl/min. p97, PAI-1 or plasminogen (5 μg) in 20 mM acetate buffer, pH 4.0 are then injected and the unreacted NHS-esters are deactivated With 35 μl of 1 M ethanolamine hydrochloride, pH 8.5. Approximately 8000 to 10000 relative units of p97, PAI-1 or plasminogen are immobilized on the sensor chip surface. Ringer solution or a 50 mM Tris/HCl buffer (pH 7.5) containing 150 mM NaCl and 50 mM $CaCl_2$ is used as the eluent buffer. Proteins are diluted in the corresponding eluent buffer and injected onto the sensor chip surface. Protein interactions are analyzed using both the Langmuir binding model, which is the simplest model for 1:1 interaction between analyte and immobilized ligand, and a two-state conformational change model which describes a 1:1 binding of analyte to immobilized ligand followed by a conformational change.

Enzymatic Assay and Cell Treatment with Soluble p97

The enzymatic activity of pro-uPA is measured using a colorimetric assay. The reaction is performed in a final volume of 200 µl in an incubation medium consisting of 50 mM Tris/HCl buffer (pH 7.5), 150 mM NaCl, and 50 mM $CaCl_2$. This incubation medium also contains 15 µg/ml VLK-pNA with or without plasminogen. Enzymatic activity is assessed in the absence or presence of p97. The reaction is started by the addition of pro-uPA. In this assay, the cleavage of VLK-pNA results in a p-nitraniline molecule that absorbs at 405 nm. The reaction product is monitored at 405 nm using a Microplate Thermomax Autoreader (Molecular Devices, CA).

HMEC-1 are grown to 85% confluency in 6-well plates and are incubated 18 hrs under 5% $CO_2$/95% air atmosphere in cell culture medium with or without p97 (100 nM). Endothelial cells are washed twice with Ringer solution and mechanically scraped from the wells. Cells are counted and frozen at −80° C. until used. A volume corresponding to 100,000 cells is incubated in the plasmin assay as above and plasmin activity is monitored at 405 nm for 60 min. HMEC-1 are also individualized by PBS citrate solution (138 mM NaCl, 2.7 mM KCl, 1.47 mM $KH_2PO_4$, 8.1 mM $Na_2HPO_4$-$7H_2O$, 15 mM Na citrate pH 6.8) for 15 min. Cells are washed twice in Ringer-Hepes solution (150 nM NaCl, 5.2 mM KCl, 2.2 mM $CaCl_2$, 0.2 mM $MgCl_2$-$6H_2O$, 6 mM $NaHCO_3$, 5 mM Hepes, 2.8 mM Glucose, pH 7.4) and counted. A volume corresponding to 100,000 cells is incubated in the plasmin assay with mAb L235 (325 nM) or IgG control. Plasmin activity is monitored at 405 nm for 480 min.

Cell Migration Assay

HMEC-1, HUVEC and SK-MEL28 cell migration is performed using Transwell filters (Costar; 8 µm pore size) precoated with 0.15% gelatin for 2 hrs at 37° C. The transwells are assembled in 24-well plates (Falcon 3097) and the lower chambers filled with 500 µl of cell culture medium. To study the effect of p97, mAb L235 or mouse IgG on cell migration, HMEC-1, HUVEC and SK-MEL28 cells are harvested by trypsinization and centrifuged. Approximately 10,000 cells are resuspended in 100 µl fresh DMEM medium with or without p97 (native or boiled for 30 minutes at 100° C.), mAb L235 or mouse IgG and added into the upper chamber of each transwell (lower chamber of the transwell also contains p97, mAb L235 or non-specific mouse IgG). The plates are then placed at 37° C. in 5% $CO_2$/95% air for 18 hrs. Cells that had migrated to the lower surface of the filters are fixed with 3.7% formaldehyde in PBS ($Ca^{2+}$/$Mg^{2+}$ free), stained with 0.1% crystal violet 20% MeOH, and counted (4 random fields per filter). Photomicrographs at 100× magnification are taken using a Polaroid Microcam or Nikon Coolpix™ 500 digital camera attached to a Nikon TMS-F microscope.

Cell Adhesion Assay

HMEC-1 cell adhesion was performed using 96-well plate precoated with 0.15% gelatin for 2 hrs at 37° C. To study the effect of soluble p97 on cell adhesion, HMEC-1 cells were harvested by trypsinization. $1\times10^4$ cells were resuspended in 100 µL of fresh medium with or without soluble p97 and added into each well. Cells were then incubated for 2 hrs at 37° C. After incubation, adherent cells were washed twice in PBS ($Ca^{+2}$/$Mg^{+2}$ free) and stained with 0.1% crystal violet/20% MeOH. Then, cells were lysed in 1% sodium dodecyl sulfate (SDS) and cell lysates were measured at 595 nm using a Microplate Thermomax Autoreader™ (Molecular Devices, Sunnyvale, Calif.). After cell staining, adherent cells were visualized at a 100× magnification using a digital Nikon Coolpix™ 5000 camera attached to a Nikon TMS-F microscope.

Capillary Tube Formation on Matrigel

Matrigel (BD Bioscience, Mississauga, ON) was thawed on ice and 50 µL were added to a 96-well plate and incubated for 10 min at 37 C. HMEC-1 or HUVEC cells were harvested by trypsinization. $2.5\times10^4$ cells were resuspended in 100 µL fresh medium and added to Matrigel-coated wells for 30 min at 37 C. After cell adhesion, the medium was removed and 100 µL of fresh cell culture medium with or without soluble p97 was added. Cells were then incubated for 18 hrs at 37° C. After incubation, tubular structures were visualized at a 40× magnification using a digital Nikon Coolpix™ 5000 camera attached to a Nikon TMS-F microscope. The length of the total capillary network was quantified using a map scale calculator by measuring and summing the length of all tubular structures observed in a chosen field.

Western Blot Analysis

HMEC-1 ($3\times10^6$ cells) were plated into a 75 $cm^2$ culture flask and exposed to complete medium containing 0, 10 or 100 nM soluble p97. After 18 hours treatment, the cells were washed twice with PBS ($Ca^{+2}$/$Mg^{+2}$ free) and solubilized in lysis buffer (1% Triton-X-100™, 0.5% NP-40, 150 mM NaCl, 1 mM ethylenediaminetetraacetic acid (EDTA), 10 mM Tris, 2% N-octylglucoside, 1 mM orthovanadate, pH 7.5) for 30 minutes on ice. Supernatant proteins were measured using a micro-BCA (bicinchoninic acid) kit from Pierce (Rockford, Ill.). Conditioned media and cell lysates of HMEC-1 were subjected to SDS-polyacrylamide gel electrophoresis (SDS-PAGE), using 5% acrylamide gels for the detection of LRP α-subunit, 10% acrylamide gels for the detection of u-PAR and eNOS, 12% acrylamide gels for the detection of GAPDH, Cav-1, pCav-1, ERK 1/2 and pERK 1/2. Separated proteins were transferred from polyacrylamide gels to polyvinylidene difluoride membranes (PerkinElmer Life Sciences, Boston, Mass.) using a Minitrans-Blot™ cell from Bio-Rad (Mississauga, ON) for 90 minutes at 80 mA per gel. Following transfer, Western blot analysis was performed. All immunodetection steps were carried out in Tris-buffered saline/0.3% Tween, pH 8.0 (TBS-Tw (0.3%)). The primary antibody was diluted 1:250 for u-PAR, α-LRP, GAPDH; 1:1000 for eNOS; 1:5000 for Cav-1, pCav-1, ERK 1/2 and pERK 1/2. The secondary antibody, used for u-PAR, α-LRP, GAPDH, Cav-1, pCav-1 and eNOS immunodetection, was a horseradish peroxidase-conjugated anti-mouse IgG from Jackson Immunoresearch Laboratories (West Grove, Pa.) diluted 1:2500 in 5% powdered skimmed milk in TBS-Tw (0.3%). Whereas, the secondary antibody, used for ERK 1/2 and pERK 1/2 immunodetection, was a horseradish peroxidase-conjugated anti-rabbit IgG from Jackson Immunoresearch Laboratories diluted 1:2500 in 5% powdered skimmed milk in TBS-Tw (0.3%). Incubation with enhanced luminol reagent (PerkinElmer Life Sciences, Boston, Mass.) and exposure to x-ray film was used for protein detection. Protein levels were quantified by laser densitometry using ChemiImager™ 5500 from Alpha Innotech Corporation (San Leandro, Calif.). In addition, fibronectin and plasminogen were immunodetected by Western blot analysis in the cell media following HMEC-1 detachment.

Total RNA Isolation and Reverse Transcription Polymerase Chain Reaction (RT-PCR)

Total RNA was extracted from cultured HMEC-1 using TRIzol™ reagent from Invitrogen (Burlington, ON). RT-PCR reactions were performed using SuperScript™ One-Step RT-PCR with Platinum® Taq Kit from Invitrogen (Burlington, ON). RT-PCR reactions were performed using specific oligonucleotide primers, derived from human cDNA sequences for the low-density lipoprotein receptor (LDL-R) gene family (that includes LDL-R, LRP, LRP 1B, LRP 2, LRP 8), u-PAR, VEGFR-2, VEGF-A and GAPDH (see Table 1 for primer sequences). Gene product amplification was performed for 40 cycles of PCR (94° C. for 15 sec. 60° C. for 30 sec (55° C. for LRP 2), 72° C. for 1 min.). RT-PCR conditions have been optimized so that the gene products were at the exponential phase of amplification. Amplification products were fractionated on 2% (w/v) agarose gels and visualized by ethidium bromide.

TABLE 1

Polymerase chain reaction (PCR) primer sequences and estimated product sizes for u-PAR, LDL-R family gene, GAPDH, VEGFR-2 and VEGF-A

| Gene | Primer sequences | Product size (bp) |
|---|---|---|
| LRP | S 5'-AGAAGTAGCAGGACCAGAGGG-3' (SEQ ID NO: 2) | 301 |
| | AS 5'-TCAGTACCCAGGCAGTTATGC-3' (SEQ ID NO: 3) | |
| LRP 1B | S 5'-TCTCTCCCTTCTCCAAAGACCC-3' (SEQ ID NO: 4) | 403 |
| | AS 5'-TCAATGAGTCCAGCCAGTCAGC-3' (SEQ ID NO: 5) | |
| LRP 2 | S 5'-CGGAGCAGTGTGGCTTATTTTC-3' (SEQ ID NO: 6) | 280 |
| | AS 5'-CAGGTGTATTGGGTGTCAAGGC-3 (SEQ ID NO: 7) | |
| LDL-R | S 5'-GGACCCAACAAGTTCAAGTGTCAC-3' (SEQ ID NO: 8) | 377 |
| | AS 5'-AAGAAGAGGTAGGCGATGGAGC-3' (SEQ ID NO: 9) | |
| LRP 8 | S 5'-CCTTGAAGATGATGGACTACCCTCG-3' (SEQ ID NO: 10) | 415 |
| | AS 5'-AAAACCCAAAAAAGCCCCCCAGC-3' (SEQ ID NO: 11) | |
| u-PAR | S 5'-ACCGAGGTTGTGTGTGGGTTAGAC-3' (SEQ ID NO: 12) | 306 |
| | AS 5'-CAGGAAGTGGAAGGTGTCGTTG-3' (SEQ ID NO: 13) | |
| GAPDH | S 5'-CCATCACCATCTTCCAGGAG-3' (SEQ ID NO: 14) | 540 |
| | AS 5'-CCTGCTTCACCACCTTCTTG-3' (SEQ ID NO: 15) | |
| VEGFR-2 | S 5'-AAAGACATTGCGTGGTCAGGCAGC-3' (SEQ ID NO: 16) | 521 |
| | AS 5'-GGCATCATAAGGCAGTCGTTCAC-3' (SEQ ID NO: 17) | 466 |
| VEGF-A | S 5'-CCAGCACATAGGAGAGATGAGCTT-3' (SEQ ID NO: 18) | 394 |
| | AS 5'-GGTGTGGTGGTGACATGGTTAATC-3' (SEQ ID NO: 19) | 262 |

S = sense strand; AS = antisense strand.

Binding of $^{125}$I-uPA·PAI-1 Complex to HMEC-1 Soluble p97-Treated Cells

First, u-PA was radioiodinated using standard procedures with Na-$^{125}$I (Amersham Pharmacia Biotech, Baie D'Urfé, QC) and an iodo-beads kit from Pierce (Rockford, Ill.). $^{125}$I-uPA·PAI-1 complex was formed by incubating PAI-1 (277 nM) with two-chain $^{125}$I-uPA (277 nM) at a molar ration of 1:1 for 1 hour at 37° C. HMEC-1 (6×10$^5$ cells) were plated onto multiwell (6 wells/plate) disposable plastic tissue culture plate using fresh media. When confluence was reach, the medium was removed and completed cell culture medium with or without soluble p97 (100 nM) was added for 18 hours. Binding experiments were performed at 4° C. to limit possible concomitant internalization during the binding interval. Briefly, after cell treatment, cell monolayers were washed and the binding was initiated by adding 10 nM of $^{125}$I-uPA·PAI-1 complex in 1 mL of Ringer/HEPES containing 0.05% ovalbumine. After 1 hour incubation, cells were washed three times and lysed with 1 mL NaOH (0.3 M). Cell associated radioactivity was quantitated in 800 μL after trichloroacetic acid (TCA) precipitation. The protein content of control and soluble p97-treated HMEC-1 cells was measured by using Coomassie® Plus Protein Assay Reagent kit (Pierce, Rockford, Ill.).

Fluorescence-Activated Cell Sorting (FACS) Analysis of Cell Surface u-PAR

HMEC-1 (3×10$^6$ cells) were plated onto 75 cm$^2$ dishes using fresh media with or without soluble p97 (100 nM). After 18 hours incubation, HMEC-1 cells were detached by incubation with PBS-citrate buffer (138 mM NaCl, 2.8 mM KCl, 1.47 mM KH$_2$PO$_4$, 8.1 mM Na$_2$HPO$_4$, 15 mM sodium citrate, pH 7.4). HMEC-1 (1×10$^6$ cells) were counted and resuspended in the binding buffer (10 mM Hepes, 140 mM NaCl, 2.5 mM CaCl$_2$, pH 7.4). Cell suspension was then incubated at 4° C. for 15 minutes with anti-u-PAR antibody #3937 (1 μg/mL), anti-α-LRP antibody (8G1 clone) (1 μg/mL) or with a non-specific IgG1 (1 μg/mL). The cells were then washed with binding buffer and incubated in the dark at 4° C. for 15 minutes with goat anti-mouse Ig-Alexa488 (1 μg/mL) (Molecular Probes, Eugene, Oreg.). After two washes with binding buffer, the cells were analyzed by flow cytometry on a Becton Dickinson FACscan™ with a 488 nM Argon laser using predetermined instrument settings. Cell surface levels of u-PAR and α-LRP, corrected for the background fluorescence intensity measured in the presence of a non-specific IgG1, were expressed as mean fluorescence intensities.

Cell Detachment Assay

HMEC-1 were plated into a 6-wells plate and placed at 37° C. in 5% CO$_2$/95% air until confluence. Cells were then exposed to serum free medium containing 150 nM plasminogen and 4 nM tPA, with or without 100 nM of melanotransferrin in the presence or absence of 150 nM alpha2-antiplasmin, 1 μM EGCG or 10 μM Ilomastat. After 24 hours treatment HMEC-1 detachment was visualized at a 100× magnification using a digital Nikon Coolpix™ 5000 camera (Nikon Canada, Mississauga, ON) attached to a Nikon TMS-F microscope (Nikon Canada).

Human Plasma

Human blood samples were collected into a citrated Vacutainer® (Becton Dickinson, Franklin Lakes, N.J.) and centrifuged at 300×g for 5 minutes at 4° C. Plasma were aliquoted in eppendorfs and used fresh or frozen at 80° C. until used.

Thromboelastography Analysis

Thromboelastography analysis was performed with citrated plasma or artificial clot model using a computerized dual-channel thromboelastograph (TEG) analyzer (model 5000; Haemoscope Corp. Niles, Ill.). For the artificial clot model fibrinogen (8.2 μM), glu-plasminogen (3.3 μM) and tPA (4.5 nM) diluted in buffer A were transferred into the analyzer cups. Artificial clots were polymerized with thrombin (0.4 U/ml). For the plasma clot model, 350 µl of citrated plasma were transferred into the analyzer cups with tPA (4.5 nM). $CaCl_2$ (0.2 M) was added to initiate the polymerisation of plasma clot. The thromboelastograph analysis for both artificial and plasma clots were performed in the presence or absence of 1 µM p97.

Radial Clot Lysis Assay

Radial clot lysis assay was performed. Briefly, fibrin-clots were obtained by incubating fibrinogen (8.2 µM), glu-plasminogen (2 µM) and 0.4 U/ml of thrombin in buffer A at 37° C. for 60 min in a 6-wells plate. Clot lysis was initiated by dropping 2 µl of tPA (2 nM) with or without p97. Clots were incubated for 30 min at 37° C. and dyed with chinese ink. Photomicrographs at 40× magnification were taken using a digital camera Nikon Coolpix 5000 camera (Nikon Canada, Mississauga, ON) attached to a Nikon TMS-F microscope (Nikon Canada).

Data Analysis

Statistical analyses are made with the Student's paired t-test using GraphPad Prism (San Diego, USA). Significant difference is accepted for p values less than 0.05.

The present invention will be more readily understood by referring to the following examples which are given to illustrate the invention rather than to limit its scope.

Example I

Transcytosis of p97 Through BBCEC Monolayers

Transcytosis experiments are performed at 37° C. for 2 hrs. $[^{125}I]$-p97 (25 nM) is added to the upper side of the cell-covered filter in the absence or presence of RAP (650 nM) or BSA (5 µM). At the end of the experiment, radiolabelled proteins are measured in the lower chamber of each well by TCA precipitation. Results represent means±SE (n=6) (FIG. 1A). In the second part of the experiment (FIG. 1B), p97 is immobilized on a sensor chip surface (CM5) as described in the Materials and Methods section above and p97, RAP and BSA (5 µg/100 µl) are injected over the immobilized p97.

Figure 1B:
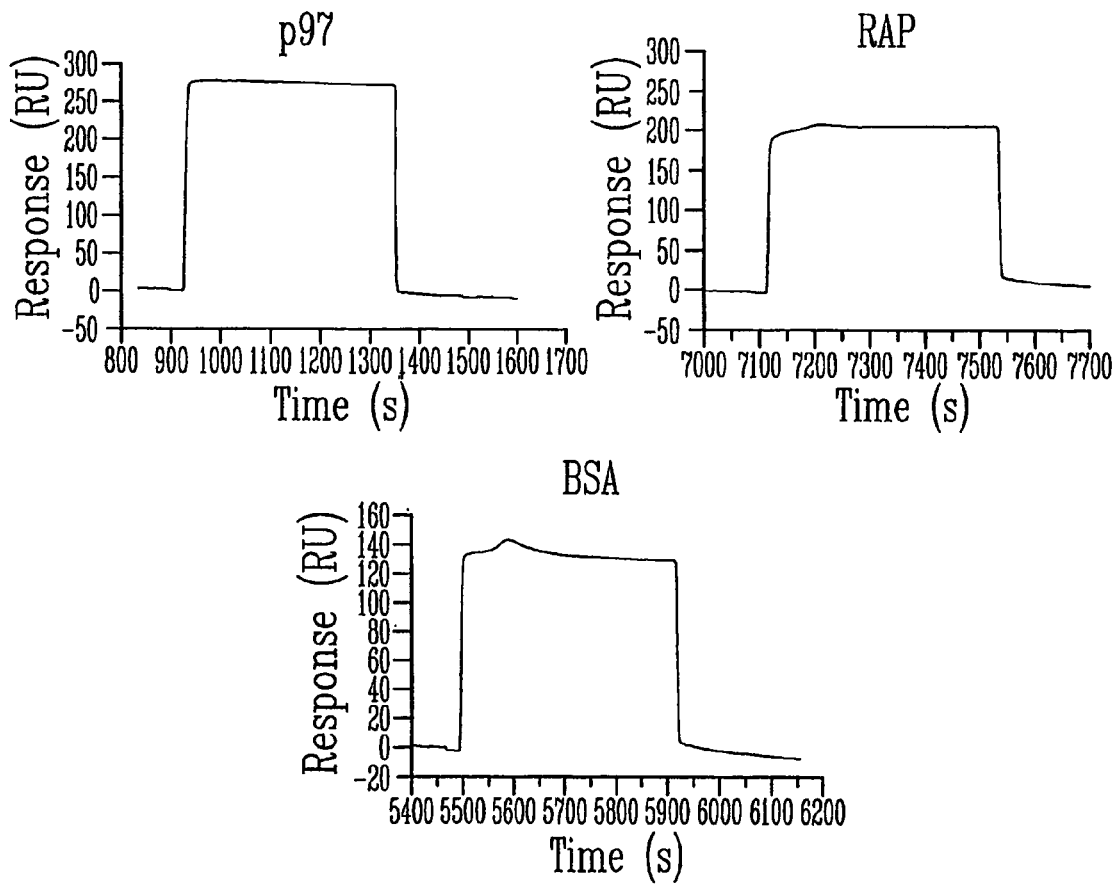

The first evaluation was the transcytosis of p97 across an in vitro model of the BBB at 37° C. (FIG. 1A). A significant (>50%) reduction in the transport of $[^{125}I]$-p97 (25 nM) from the apical (blood side) to the basolateral side (brain side) of BBCEC monolayers was observed in the presence of 640 nM RAP. Transcytosis of $[^{125}I]$-p97 was unaffected by a 200-fold molar excess of BSA. The permeability coefficient for sucrose is similar in the absence or presence of RAP indicating that the integrity of the BBCEC monolayers was unaffected by this protein. The results with RAP also indicate that LRP is involved in p97 transcytosis since it has been reported to be an LRP ligand, whereas BSA was shown to bind to megalin, another member of the LDL receptor family, probably via cubilin (Kozyraki R et al., 2001 Proc Natl Acad Sci USA 98:12491-12496). To determine whether protein interaction could occur between p97 and RAP, leading to a reduction in p97 transcytosis, protein interactions were investigated by using biological interaction analysis in real-time (FIG. 1B). For this analytical approach, p97 was first immobilized on the surface of a sensor chip. Using standard NHS/EDC coupling procedures about 8 to 10 $ng/mm^2$ of p97 were immobilized. RAP or BSA (0.05 µg/µl) were then injected over immobilized p97. No interactions could be observed between these proteins and p97, indicating that the inhibition of $[^{125}I]$-p97 transcytosis is not related to protein interactions between p97 and RAP.

Example II

Pro-uPA and p97 Interaction

Biospecific Interaction Analysis Between p97 and anti-p97 mAbs

Biospecific interaction analysis in real-time between p97 and various anti-p97 mAbs is performed as follows. p97 is immobilized on a sensor chip (CM5) using standard coupling procedures incorporating NHS, EDC and ethanolamine. Different mAbs directed against p97 (HybC, HybE, HybF, L235, 2C7, 9B6), diluted to 0.05 µg/µl in Ringer/Hepes, are injected into the BIAcore at a flow rate of 5 µl/min. The surface plasmon resonance response obtained for these mAbs is plotted (in relative units (RU)) as a function of time. After each injection immobilized p97 is regenerated with 0.2M glycine at pH 2 for 2 min (n=4).

Figure 2:
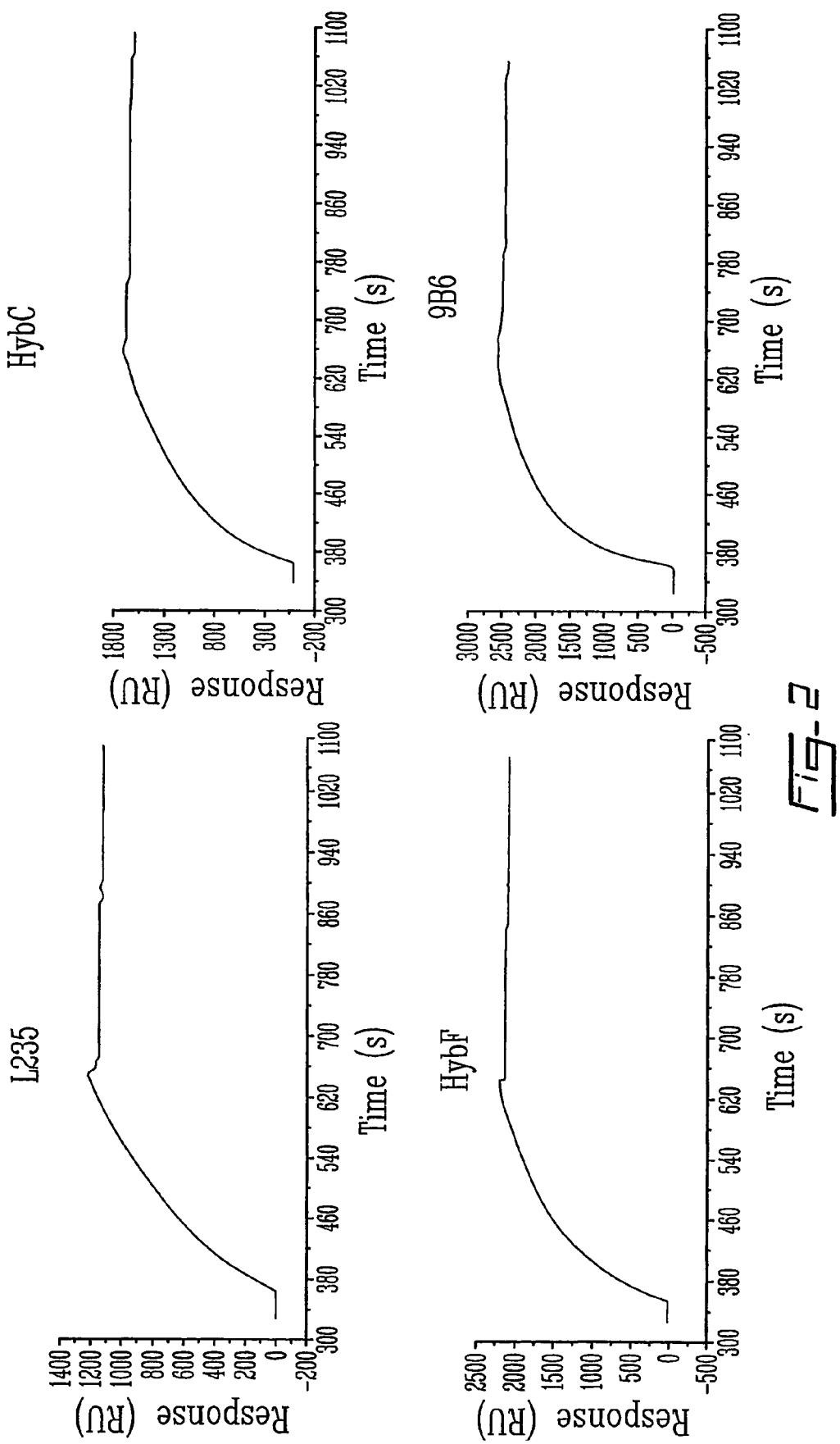
FIG. 2 illustrates that various monoclonal antibodies to p97 are still able to recognize p97 following their immobilization to a sensor chip surface, indicating that the p97 protein remains intact following immobilization.
Figure 2:
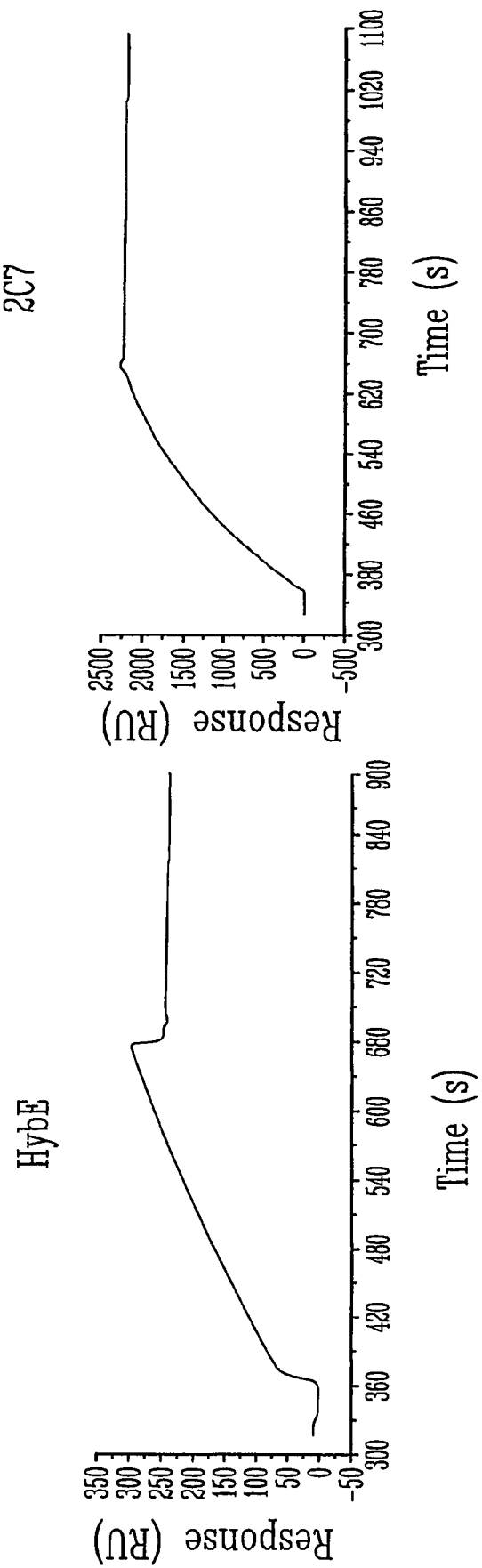

To evaluate the impact of immobilization procedures on the structural integrity of p97, different mAbs directed against various conformational epitopes of p97 were injected over p97 (FIG. 2). The surface plasmon resonance (SPR) signal generated by the interaction between p97 and various mAbs varied from 250 relative units (RU) to 2500 RU. These data show that the mAbs could still recognize p97, indicating that the protein is intact following its immobilization on the sensor chip surface. Table 2 shows the kinetic parameters estimated by the BIAevaluation software for antibody interactions with p97. From these values, the affinity constant $(K_A=k_a/K_d)$ of these mAbs for immobilized p97 ranged from 0.08 to 1.6 $nM^{-1}$ and for the relative affinities are HybE<L235<9B6<2C7, HybC<HybF.

TABLE 2

Kinetics of interaction between immobilized p97 and mAbs.

| Antibodies | ΔRU | $K_a$ ($M^{-1}s^{-1}$) | $K_d$ ($s^{-1}$) | $K_A = K_a/K_d$ ($M^{-1}$) | $K_D = K_d/K_a$ (M) |
|---|---|---|---|---|---|
| L235 | 1055 ± 82 | $4.4 \times 10^4$ | $5.3 \times 10^{-5}$ | $0.9 \times 10^9$ | $0.1 \times 10^{-10}$ |
| HybC | 1509 ± 184 | $7.2 \times 10^4$ | $4.5 \times 10^{-5}$ | $1.6 \times 10^9$ | $6.4 \times 10^{-10}$ |
| HybE | 232 ± 52 | $0.9 \times 10^4$ | $9.8 \times 10^{-5}$ | $0.08 \times 10^9$ | $0.01 \times 10^{-10}$ |
| HybF | 2199 ± 150 | $8.0 \times 10^4$ | $3.0 \times 10^{-5}$ | $2.7 \times 10^9$ | $3.8 \times 10^{-10}$ |
| 9B6 | 2440 ± 13 | $1.2 \times 10^4$ | $9.1 \times 10^{-5}$ | $1.3 \times 10^9$ | $7.9 \times 10^{-10}$ |
| 2C7 | 2290 ± 87 | $5.9 \times 10^4$ | $3.8 \times 10^{-5}$ | $1.6 \times 10^9$ | $6.5 \times 10^{-10}$ |

The difference between the relative units measured after and before injection of mAbs directed against p97 are presented (ΔRU) as well as the apparent association ($K_a$) and dissociation ($K_d$) constants. The affinity ($K_A$) and dissociation ($K_D$) constants were calculated from the $K_a$ and $K_d$.

Molecular Interactions of p97 and Various Components of the PA:plasmin System

Determining the molecular interactions between p97 and various components of the PA:plasmin system was as follows. Pro-uPA and tPA (0.05 µg/µl), diluted in Ringer/Hepes, are injected onto immobilized p97 on a sensor chip at a flow rate of 5 μl/min. The SPR response for these proteins is plotted in RU as a function of time. p97 (0.05 μg/μl) is also injected over immobilized PAI-1 (p97/PAI-1). Plasminogen, plasmin or angiostatin (0.05 μg/μl) are also injected onto immobilized p97. The SPR response for these proteins is plotted in RU as a function of time. The results indicate that pro-uPA and plasminogen interact with p97. After each injection the sensor chip surface with immobilized p97 is regenerated by injecting 10 mM glycine, pH 2.2 for 2 min.

Figure 3A:
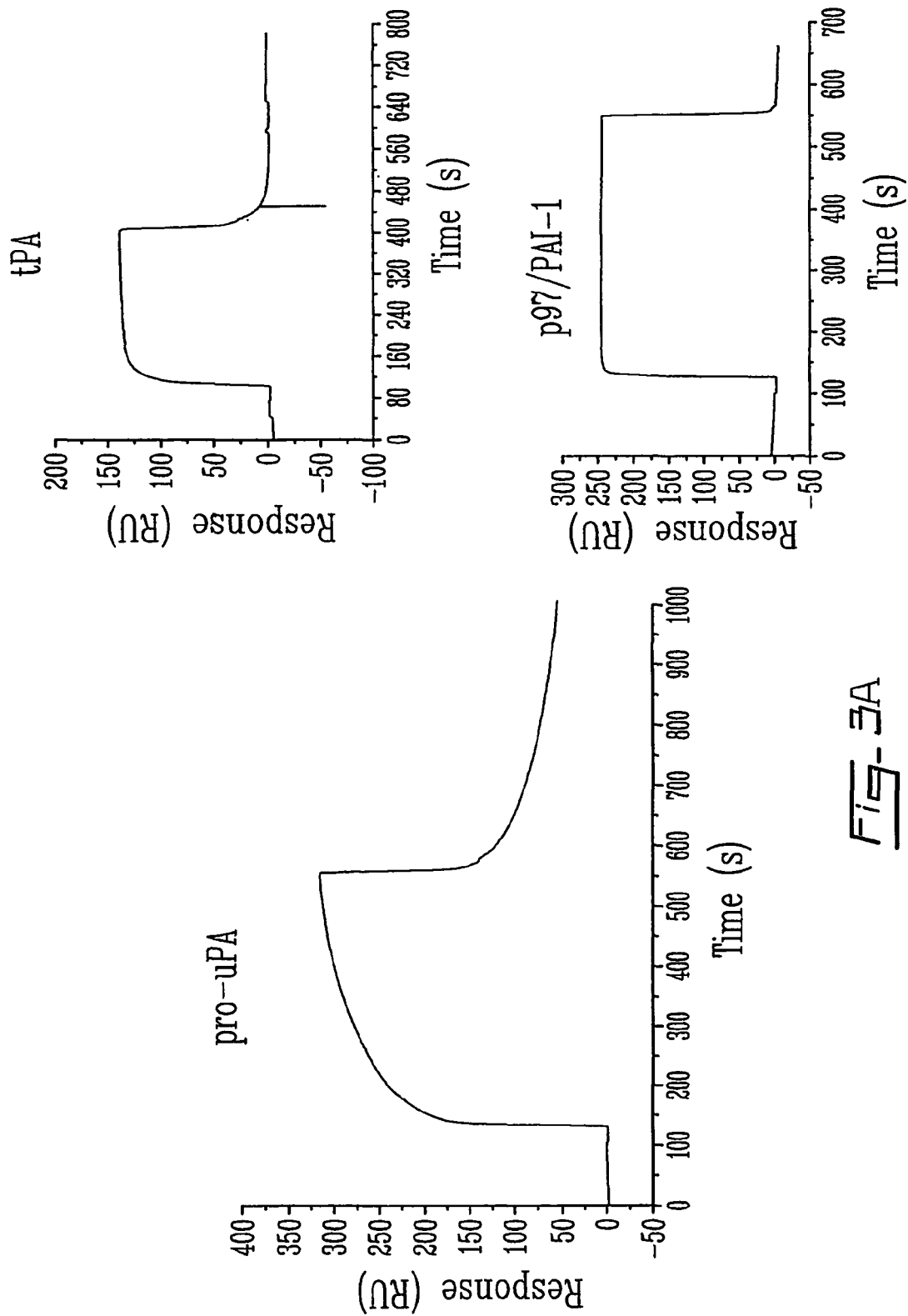
FIG. 3A-3B illustrates that (3A) sensor chip surface immobilized p97 can interact with pro-uPA but no interaction can be detected between p97 and PAI-1 or between p97 and tPA and that (3B) plasminogen also interacts with immobilized p97 whereas plasmin and angiostatin, two plasminogen fragments do not.
Figure 3B:
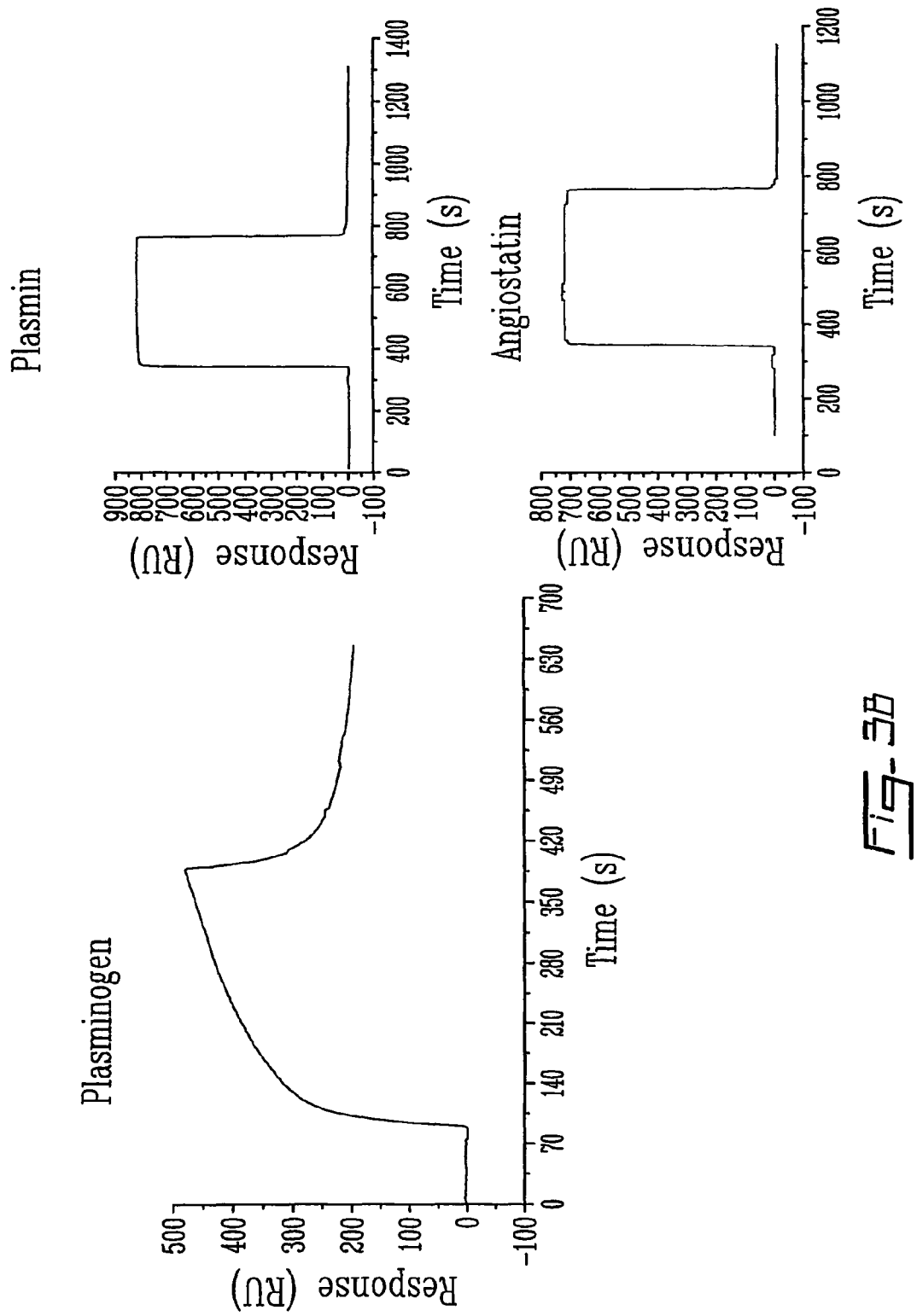

When pro-uPA and tPA (0.05 μg/μl) were injected over immobilized p97, protein interaction occurred between pro-uPA and p97 but not between tPA and p97 (FIG. 3A). About 8-10 ng/mm$^2$ of PAI-1 was also immobilized onto another well of a sensor chip surface using NHS/EDC coupling conditions. No interaction between p97 and immobilized PAI-1 could be detected (FIG. 3A). However a strong interaction could be observed when tPA was injected over PAI-1, indicating that PAI-1 can still interact with tPA following immobilization. In addition, plasminogen, plasmin and angiostatin (0.05 μg/μl) were injected over immobilized p97 (FIG. 3B). According to the SPR, plasminogen also interacts with immobilized p97 whereas plasmin and angiostatin, two plasminogen fragments, do not. The kinetic data obtained from binding of pro-uPA or plasminogen to immobilized p97 biosensor surface were evaluated using both the 1:1 Langmuir binding model and the two state conformational change model. Interestingly, the two state conformational change model was a better fit than the 1:1 Langmuir binding model when comparing a single concentration of either pro-uPA and plasminogen over p97 biosensor surface. Kinetic data obtained with the two state conformational model are presented in Table 3. Kinetic data for the interaction between pro-uPA and p97 shows an association constant ($k_{a1}$) of $6.6 \times 10^3$ M$^{-1}$s$^{-1}$ and a dissociation rate constant ($k_{d1}$) of $1.7 \times 10^{-3}$ s$^{-1}$. Furthermore, the forward rate constant ($k_{a2}$=$3.2 \times 10^{-3}$ s$^{-1}$) and backward rate constant ($k_{d2}$=$7.1 \times 10^{-4}$ s$^{-1}$) for the conformational change provide an apparent equilibrium dissociation constant (($K_D$=$k_{d1}/k_{a1}$)/($k_{d2}/k_{a2}$)) of 65 nM. The kinetic analysis of plasminogen interaction with p97 shows an association constant ($k_{a1}$) of $2.1 \times 10^4$ M$^{-1}$s$^{-1}$. The dissociation rate constant ($k_{d1}$=$4.3 \times 10^{-2}$ s$^{-1}$), as well as the forward rate constant ($k_{a2}$) of $6.0 \times 10^{-2}$ s$^{-1}$ and backward rate constant ($k_{d2}$) of $1.1 \times 10^{-3}$ s$^{-1}$, are different from those seen for the pro-uPA interaction with p97. However, the apparent equilibrium dissociation constant ($K_D$) between p97 and plasminogen is 350 nM, which is different from that observed for the interaction of pro-uPA with immobilized p97.

parameters are: $k_{a1}$, association rate constant for A+B1=AB1 (M$^{-1}$s$^{-1}$); $k_{d1}$, dissociation rate constant for AB1=A+B1 (s$^{-1}$); $k_{a2}$, forward rate constant for AB=ABX (s$^{-1}$); $k_{d2}$, backward rate constant for AB=ABX (s$^{-1}$). The mean Chi$^2$ values for the sensorgram fits were less than 0.4.

Effect of p97 on Pro-uPA, tPA and Plasminogen

To evaluate the effect of p97 interaction on pro-uPA, tPA and plasminogen, the serine activity (VLK-pNA hydrolysis) of 90 nM pro-uPA and 75 nM tPA were measured in the absence (○) or presence (●) of 70 nM p97 without plasminogen using a colorimetric assay, both with and without p97 (FIGS. 4A and 4B). The reaction was performed in a final volume of 200 μl as described in the Materials and Methods section above. In both FIGS. 4A and 4B, controls were also performed with p97 (■) but without pro-uPA or tPA (n=9, for pro-uPA; n=6, for tPA). In the absence of p97, only a slight activity was measured for both pro-uPA and tPA. However, the VLK-pNA hydrolysis by pro-uPA goes from less than 50 AU/min in the absence of p97 to more than 450 AU/min when p97 is added into the incubation (FIG. 4A). Addition of p97 to tPA elicits no observable effect and p97 alone had no proteolytic activity (FIG. 4B). The results from both SPR and enzymatic activity indicate that the change in pro-uPA conformation induced by p97 increased its ability to degrade the plasmin substrate.

To determine whether interaction with p97 leads to a cleavage of pro-uPA, the proteins were co-incubated for 5 min. at 37° C. in the presence or absence of plasminogen. They were then separated by SDS-PAGE under reducing conditions using a 12.5% acrylamide gel and stained with standard Coomassie Blue. The results are shown in FIG. 4C. The lanes of the gel are as follows (FIG. 4C): 2 μg of p97 (lane 1), 1 μg pro-uPA (lane 2) and 2 μg plasminogen (lane 3) were incubated for 5 min. at 37° C. alone as controls. Pro-uPA (2 μg) was incubated at 37° C. for 5 min. with 2 μg of p97 (lane 4). Plasminogen and Pro-uPA were added without incubation (lane 5) and with 5 min. incubation at 37° C. (lane 6). Pro-uPA with 2 μg of both p97 and plasminogen were added without incubation (lane 7) or with 5 min. incubation at 37° C. (lane 8). Tc-uPA (2 μg) was also loaded as a control (lane 9). Under these conditions p97 and uPA migrated as 97 kDa and 33 kDa bands, respectively, whereas pro-uPA migrated as a single band at 55 kDa. No major degradation of either protein could be detected, indicating that the incubation of pro-uPA with p97 under the conditions used to perform the VLK-pNA hydrolysis did not cleave either protein. Even after 6 hours incubation at 37° C., both proteins were stable. In the pres-

TABLE 3

Kinetics of interaction between immobilized p97 and pro-uPA or plasminogen using the two state conformational model

| Immobilized proteins | Ligands | $k_{a1}$ ($\times 10^4$ M$^{-1}$s$^{-1}$) | $k_{a2}$ ($\times 10^{-3}$ s$^{-1}$) | $k_{d1}$ ($\times 10^{-3}$ s$^{-1}$) | $k_{d2}$ ($\times 10^{-4}$ s$^{-1}$) | KD ($\times 10^{-9}$ M) |
|---|---|---|---|---|---|---|
| p97 | pro-uPA | 66.2 | 3.2 | 6.0 | 7.1 | 65 |
|  | plasminogen | 2.1 | 6.0 | 3.1 | 11.2 | 350 |

Kinetic parameters of Table 3 were based on a two state conformational change binding model using the biosensorgram shown in FIG. 3. This model describes a 1:1 binding of analyte to immobilized ligand followed by a conformational change in the complex. It is assumed that the conformationally changed complex can only dissociate through the reverse of the conformational change: A+B=AB=ABx. The dissociation constants ($K_D$) were derived using both association (ka) and dissociation ($k_d$) rates ($K_D$=($k_{d1}/k_{a1}$)×($k_{d2}/k_{a2}$)). The ence of plasminogen, pro-uPA was cleaved after an incubation of 5 min. at 37° C. and two major fragments of 33 kDa and 29 kDa could be observed. When p97 was added to the incubation medium, the generation of these fragments did not change.

The impact of p97 on plasminogen fragmentation by pro-uPA was further estimated using 6 hours incubation at 37° C. and the results are shown in FIG. 4D. The lanes of the gel are as follows: 3 μg of p97 (lane 1), glu-plasminogen (lane 2) and lys-plasminogen (lane 3) were incubated alone for 6 hours at 37° C. as controls. In lane 4, 3 μg of both glu-plasminogen and p97 were also incubated for 6 hours at 37° C. Pro-uPA (20 ng) was added to plasminogen for the same period of incubation at 37° C. (lane 5). p97 was added to pro-uPA and plasminogen for 6 hours at 37° C. (lane 6) or 4° C. (lane 7). In lane 8, 3 μg of angiostatin (lane 8) was also added as a control. Proteins were separated on a 7.5% acrylamide gel under non-reducing conditions and stained with Coomassie blue. When p97 is added to glu-plasminogen no apparent fragment was generated. In contrast, the addition of a low amount (10 ng) of pro-uPA, which could not be detected using standard Coomassie blue staining, induced degradation of Glu-plasminogen with the appearance of fragments which migrated at the same molecular weight as Lys-plasminogen. Moreover, when p97 is added to glu-plasminogen and pro-uPA, the degradation profile of glu-plasminogen is changed. In the presence of p97 with glu-plasminogen and pro-uPA, higher levels of bands migrating at the same molecular weight as lys-plasminogen were observed and two other fragments appeared at 50 and 30 kDa. These fragments do not seem to be related to angiostatin since they migrated at a different molecular weight than did the control angiostatin at 42 kDa. These results indicate that p97 alters the cleavage of glu-plasminogen by pro-uPA.

Example III

Plasminogen Activation by p97

The interaction of p97 with pro-uPA was further characterized by measuring the activation of plasminogen by pro-uPA in the presence of p97 (FIG. 5). The plasminolytic activity of 1 nM uPA was measured without (○) or with (●) 70 nM p97 in the presence of 30 nM plasminogen. The reaction was performed in a final volume of 200 μl as described in the Materials and Methods section above. As a control, the enzymatic activity in the presence of p97 alone was also measured (■). When p97 is added to pro-uPA and plasminogen, the VLK-pNA hydrolysis is 4-fold higher after 180 min (FIG. 5A). Control experiments performed with p97 indicated that this protein alone does not generate plasmin when it is added to plasminogen.

The plasmin activity in the presence of various concentrations of p97 was also measured (FIG. 5B). Plasmin activity induced by pro-uPA was measured in the presence of various p97 concentrations. Since the generation of plasmin proceeds at a constant rate under the assay conditions used, plotting the experimental data as a function of time $(t)^2$ allowed for the determination of the initial rate of plasmin formation. From these linear curves, the initial plasmin activity measured in the absence of p97 was subtracted from the activities obtained in the presence of various p97 concentrations. Thus, the data represent the initial rates of plasmin-activity (corresponding to the slopes) in the presence of various p97 concentrations. p97 stimulates the plasminogen cleavage by pro-uPA in a dose-dependent manner with half-maximal stimulation occurring at 25±6 nM.

The effect of p97 on plasmin activity in the presence of various concentrations of plasminogen was also measured (FIG. 5C). Plasmin activity induced by pro-uPA was measured without (○) or with (●) 250 nM p97 and various concentrations of plasminogen. Initial rates of plasmin activity calculated at several plasminogen concentrations were plotted as a function of plasminogen concentrations. The resulting experimental data were fitted using nonlinear regression analysis. p97 decreased the apparent Km of pro-uPA for plasminogen from 188±22 to 102±17 nM and increased the $V_{max}$ from 6.9±0.4 to 8.9±0.6 AU/min. These results indicate that p97 positively affects the activation of plasminogen by pro-uPA by increasing the catalytic efficiency by a factor of 2.4-fold.

To determine whether the induction of plasmin formation by p97 was specific, the formation of plasmin by pro-uPA in the presence of either the mAb L235 (directed against p97) or a non-specific IgG was measured (FIG. 5D). The plasminolytic activity of pro-uPA was measured in the presence of 70 nM p97 and 65 nM of either mAb L235 (○) or non-specific mouse IgG (●). One representative experiment is shown and data represent the means±SD of values obtained from triplicates (n=3). MAb L235 (50 nM) inhibited the pro-uPA activation induced by p97 by 50%. These results indicate that the effect of p97 upon pro-uPA's activation of plasminogen is specific and involves the epitope recognized by the mAb L235.

Example IV

Inhibition of Cell Migration by mAb L235

Since p97 affects the activation of plasminogen in vitro and since the uPA/uPAR system is important in cell migration, it was further investigated whether endogenous p97 might be associated with this process. Cell migration of HMEC-1, SK-MEL28 cells or HUVEC was measured using modified Boyden chambers as described in the Materials and Methods section above. Because p97 was first identified in melanoma cells (Brown J P et al., 1981 *Proc Natl Acad Sci USA* 78:539-543), the impact of the mAb L235 on the migration of human melanoma (SK-MEL28) cells was also measured (FIG. 6A). Cells that had migrated to the lower surface of the filters were fixed and stained with crystal violet. Images obtained from a representative experiment are shown. Cells that had migrated in the presence of 50 nM mAb L235 or a non-specific mouse IgG were also counted. The results were expressed as the percentage of the control measured in the presence of a non-specific mouse IgG and represent the means±SD (n=5 for HMEC-1; n=4 for SK-MEL28; n=3 for HUVEC). Statistically significant differences are indicated by ***p<0.001 (Student's t-test). In the presence of mAb L235 (50 nM), the migration of HMEC-1 and SK-MEL28 cells was inhibited by 54% and 48%, respectively. However, cell migration of HUVEC was unaffected by this concentration of mAb L235.

Endogenous p97 was immunodetected in lysates or serum-deprived culture media (18 hours) from HMEC-1, SK-MEL28 and HUVEC cells. FIG. 6B shows the detection of endogenous p97 by Western blot analysis. Proteins were separated by SDS-PAGE and were electrophoretically transferred to PVDF membranes. p97 was detected by Western blotting using mAb L235 and a secondary anti-mouse IgG linked to peroxidase. p97 migrated under unreduced conditions at 73 and 60 kDa, as previously observed. It was highly expressed in lysates from HMEC-1 and SK-MEL28 cells and at lower levels in their respective conditioned culture media. In HUVEC cells, p97 was however almost undetectable. In fact, the exposure time was at least 30 times greater to detect a much lower level of p97 in HUVEC compared to HMEC-1 and SK-MEL28 cells. These results indicate that mAb L235, by interacting with endogenous p97, inhibits the migration of HMEC-1 and SK-MEL28 cells. This also indicates that the endogenous p97 in these cells is involved in cell migration.

Example V

Effect of Exogenous p97 on Cell Migration

It was also estimated whether exogenous p97 could affect the migration of HMEC-1 and SK-MEL28 cells. HMEC-1 and SK-MEL28 cell migration was performed using modified Boyden chambers as described in the Materials and Methods section above. Cells that had migrated in the presence or absence of p97 (100 nM) to the lower surface of the filters were fixed and stained with crystal violet. The results are shown in FIGS. 7A and 7B. Cells that had migrated were also counted and expressed as a percentage of the control cells, measured in the absence of p97 (n=4, for HMEC-1; n=3, for SK-MEL28). Exogenous p97, at 10 nM and 100 nM, inhibited the migration of HMEC-1 cells by 34% and 50% (FIG. 7C). The migration of SK-MEL28 cells was inhibited by 44% and 70% in the presence of 10 and 100 nM p97. Migration of HUVEC cells was unaffected by these concentrations of p97. Moreover, this inhibition of cell migration is not related to a reduction of endothelial or melanoma cell adhesion since the same concentrations of p97 did not affect adhesion on gelatin of either HMEC-1 or SK-MEL28 cells.

Example VI

Inhibition of Plasminolytic Activity at the Cell Surface by Soluble p97 and mAb L235

Figure 8A:
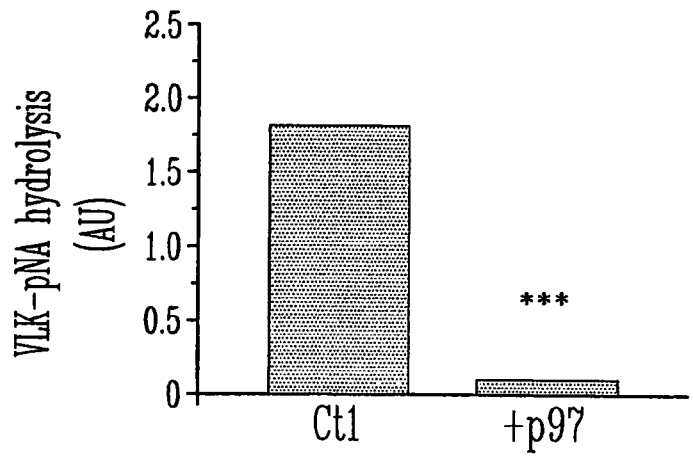
FIG. 8 illustrates the inhibition of plasminolytic activity at the cell surface by soluble p97 and mAb L235 and shows that (A) 100 nM p97 results in 95% inhibition of plasminogen activation in HMEC-1 cells; and (B) mAb L235 results in more than 50% inhibition of plasminolytic activity.
Figure 8B:
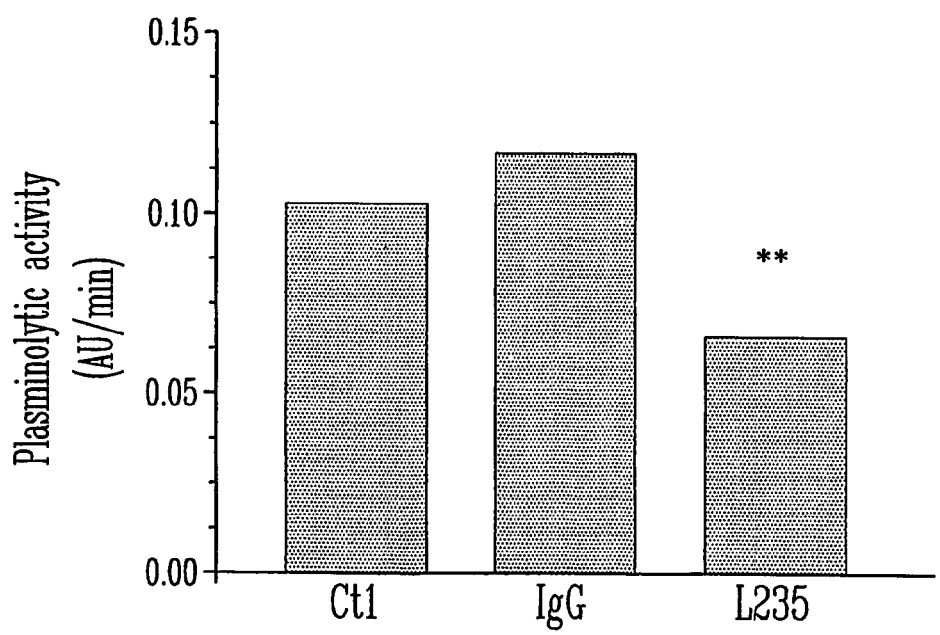

The effect of p97 on plasminolytic activity was determined as follows. HMEC-1 cells were treated for 18 hours with 100 nM p97 (+p97) or Ringer solution (Control). Following this treatment the plasminolytic activity was measured using standard conditions, as described in the Materials and Methods section above. When cells were treated with p97 (100 nM), plasminogen activation was inhibited by 95% (FIG. 8A). This marked reduction in the plasminolytic capacity of these cells by soluble p97 could explain the inhibition of HMEC-1 migration. The effect of mAb L235 on plasminolytic activity of HMEC-1 was also determined. HMEC-1 cells ($1 \times 10^5$ cells) were pre-incubated 1 hr. at 37° C. with Ringer solution (Ctl) or with 250 nM of either mAb L235 or non-specific mouse IgG. Following this pre-incubation, the plasminolytic activity was measured for 6 hrs by adding pro-uPA (1 nM) and plasminogen (50 nM) using standard conditions, as described in the Materials and Methods section. The plasminolytic activity of HUVEC was also measured using $1 \times 10^5$ cells under the same conditions. Data represent the means±SD of three independent experiments performed in triplicate. Statistically significant differences are indicated by *** where p<0.001 (Student's t-test). When HMEC-1 cells were treated with the mAb L235, the plasminolytic activity was inhibited by more than 50% compared to non-specific mouse IgG (FIG. 8B). This inhibition by the mAb L235 indicates that endogenous, membrane-bound p97 participates in plasminogen activation in HMEC-1.

Example VII

Anti-Angiogenic Properties of p97

Angiogenesis, a complex multistep process that leads to the outgrowth of new capillaries from pre-existing vessels, is an essential mechanism in wound healing, embryonic development, tissue remodeling, and in tumor growth and metastasis. This process involves EC proliferation, migration and morphogenic differentiation into capillary-like structures. One of the key elements in cell migration is the urokinase-type plasminogen activator receptor (u-PAR). The plasminogen activator (PA) family is composed of urokinase-type plasminogen activator (u-PA) and tissue-type plasminogen activator (t-PA); their inhibitors are the plasminogen activator inhibitor type 1 and 2 (PAI-1; PAI-2). u-PAR mediates the internalization and degradation of u-PA/inhibitor complexes via the low-density lipoprotein receptor-related protein (LRP), whereas LRP mediates the internalization and degradation of t-PA/inhibitor complexes. Thus, the u-PAR/LRP system controls cell migration by regulating plasminogen activation by PAs at the cell surface. PAs are therefore involved in angiogenesis by enhancing cell migration, invasion and fibrinolysis. Moreover, plasminogen needs to be first converted to the two-chain serine protease plasmin. When Glu-plasminogen, the native circulating form of the zymogen, is bound to the cell surface, plasmin generation by PAs is markely stimulated compared with the reaction in solution. Optimal stimulation of plasminogen activation at the EC surface requires the conversion of Glu-plasminogen to Lys-plasminogen.

Since soluble p97 interacts with plasminogen and single-chain u-PA (scu-PA), the potential role of soluble p97 on angiogenesis was further investigated. Herein, it is shown that soluble p97 inhibits EC migration and tubulogenesis by affecting both u-PAR and LRP expression as well as the binding of the u-PA·PAI-1 complex at the cell surface of human microvessel EC (HMEC-1). To further understand the impact of soluble p97 on morphogenic differentiation of EC into capillary-like structures, the expression of key players associated with angiogenesis was also determined.

Cell Culture

Cells were cultured under 5% $CO_2$/95% air atmosphere. Human dermal microvessel endothelial cells (HMEC-1) were from the Center for Disease Control and Prevention (Atlanta, Ga.) and were cultured in MCDB 131 supplemented with 10 mM L-glutamine, 10 ng/ml EGF, 1 µg/ml hydrocortisone and 10% inactivated foetal bovine serum (FBS). HUVECs was obtained from ATCC (Manasas, Va.). HUVECs were cultured in EGM-2 medium (bullet kit, Clonetics #CC-3162) and 20% inactivated FBS.

Enzymatic Assay

Figure 9:
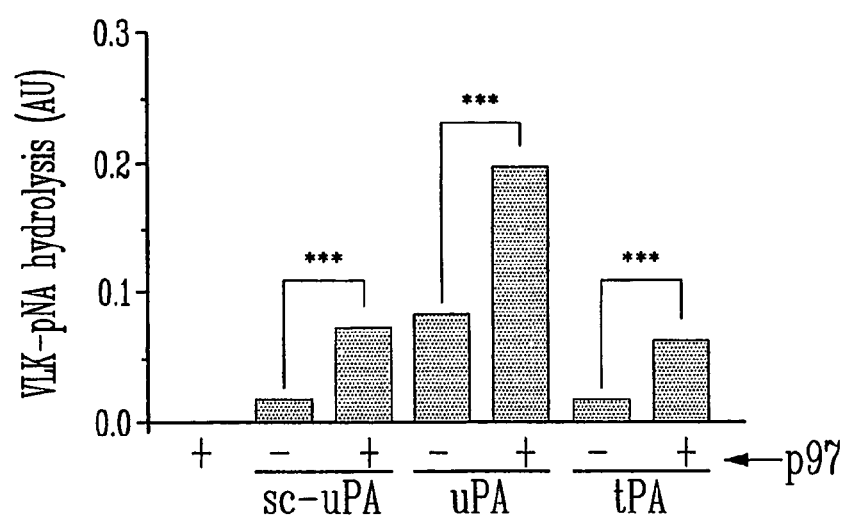
FIG. 9 illustrates the stimulatory effect of p97 on plasminogenolytic activity of single chain urokinase plasminogen activator (sc-uPA), uPA and tissue plasminogen activator (tPA) in vitro.

The enzymatic activity of p97, sc-uPA, uPA and tPA was measured using a colorimetric assay (FIG. 9). The reaction was performed in a final volume of 200 µL in an incubation medium consisting of 50 nM Tris/HCl buffer (pH 7.5), 150 mM NaCl and 50 mM $CaCl_2$. This incubation medium also contained 15 µg/mL L-var-leu-lys-p-nitraniline (VLK-pNA) and 25 nM glu-plasminogen. The enzymatic activity was assessed with or without 100 nM soluble p97. The reaction was started by the addition of 1 nM sc-uPA, uPA or tPA. In this assay, the cleavage of VLK-pNA results in a p-nitraniline molecule that absorbs at 405 nm. The reaction product was monitored at 405 nm using a Microplate Thermomax Autoreader™ (Molecular Device, CA).

Western Blot Analysis

Figure 10A:
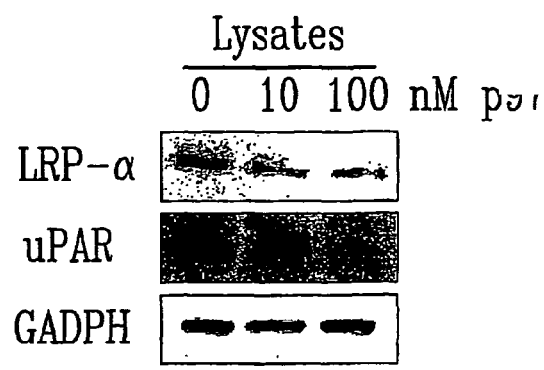
FIG. 10 illustrates that low density lipoprotein related protein (LRP) and the urokinase activator receptor (uPAR) are down regulated in p97 treated HMEC-1 cells.
Figure 10B:
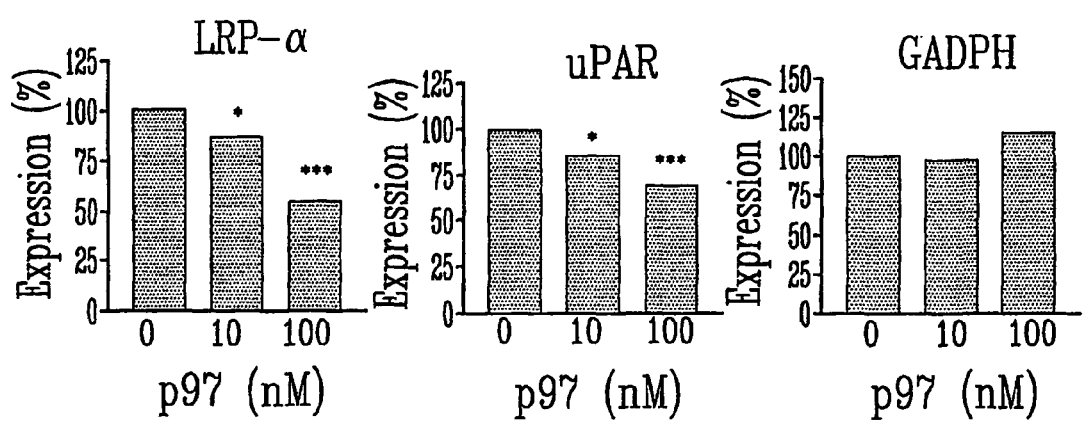

In FIG. 10, HMEC-1 ($3 \times 10^6$ cells) were plated into a 75 $cm^2$ culture flask with fresh medium with or without 10 and 100 nM of p97. After 18 hours treatment, HMEC-1 were washed twice PBS $Ca^{+2}/Mg^{+2}$ free and solubilized in lysis buffer (1% Triton-X-100™, 0.5% NP-40, 150 mM NaCl, 1 mM EDTA, 10 mM Tris, 2% N-octylglucoside, 1 mM orthovanadate, pH 7.5) for 30 minutes on ice. Supernatant proteins were measured using a micro-BCA (bicinchonic acid) kit (Pierce). Conditioned media and cell lysates of HMEC-1 were subjected to SDS-PAGE using 5% acrylamide gel for the detection of α-LRP, 10% acrylamide gel for the detection of uPAR. Separated protein were transferred electrophoretically from polyacrylamide gel to PVDF transfer membrane (PerkinElmer Life Sciences) in a Minitrans-Blot™ cell (Bio-Rad) for 90 minutes at 80 mA per gel. Following transfert, western blot analysis were performed. All immunodetection steps were carried out in Tris-buffered saline/0.1% Tween, pH 8.0 [TBS-Tw (0.1%)]. The primary antibody was diluted 1:250 for LRP and uPAR. The secondary antibody, horseradish peroxidase-conjugated anti-mouse IgG (Jackson), was diluted 1:2500 in 1% powdered skimmed milk in TBS-Tw. Incubation with enhanced luminol reagent (PerkinElmer Life Sciences) and exposure to x-ray film were used to determined protein levels Capillary Tube Formation on Matrigel In FIG. 11, Matrigel was thawed on ice and added (50 μl) to a 96-well plate for 10 min at 37° C. HUVEC or HMEC-1 were harvested by trypsinization and spun down. About 25 000 cells were resuspended and added to Matrigel-coated wells for 30 min at 37° C. After cell adhesion, the medium was removed and 100 μl of fresh cell culture medium with or without p97 was added. Wells were then incubated for 18 hours at 37° C. After incubation, tubular structures were visualized using a Nikon TMS-F microscope (at a magnification of ×40). The length of the capillary network was quantified using a map scale calculator.

In conclusion, as shown in FIG. 9, p97 stimulates the plasminolytic activity of single chain urokinase plasminogen activator (sc-uPA or pro-uPA), uPA and tissue plasminogen activator (tPA) in vitro. In addition, as shown in FIG. 10, low density lipoprotein related protein (LRP) and the urokinase activator receptor (uPAR) are down regulated in p97 treated MHEC-1 cells. Furthermore, as shown in FIG. 11, HMEC-1 and HUVEC capillary tube formation is inhibited by low concentration of soluble p97.

Figure 11A:
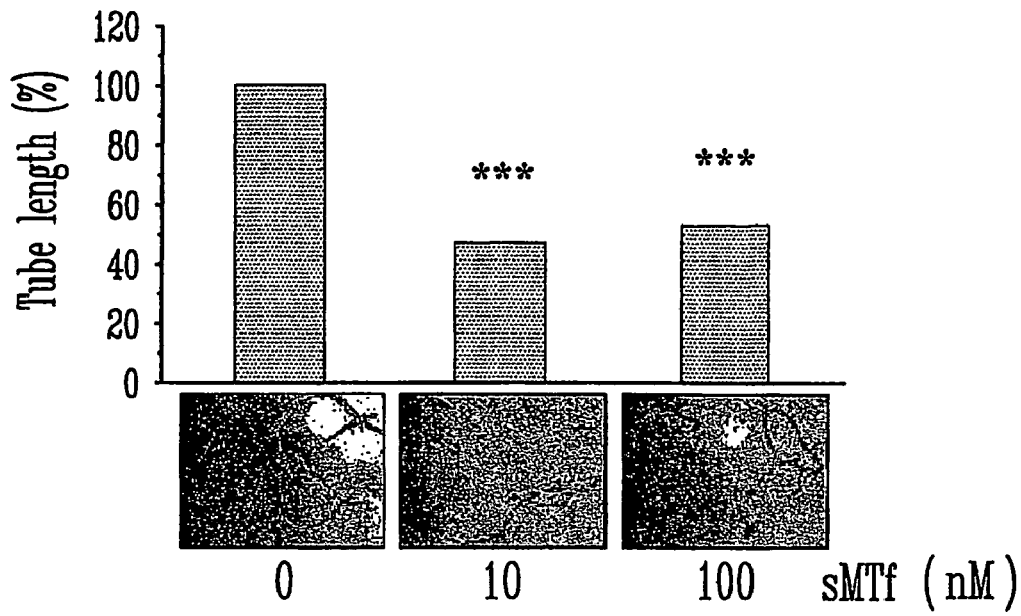
FIG. 11 illustrates that soluble p97 inhibits the morphogenic differentiation of HMEC-1 (11A) and HUVEC (11B) into capillary-like structures, when grown onto Matrigel-coated wells in the presence or absence of soluble p97 (10 nM or 100 nM) as described in the Materials and Methods sections hereinafter, the length of the total capillary network being quantified after 18 hours using a map scale calculator by measuring and summing the length of all tubular structures observed in a chosen field. The results were expressed as the percentage of capillary-like tubes in soluble p97-treated cells compared to untreated HMEC-1 and HUVEC cells (11C)
Figure 11B:
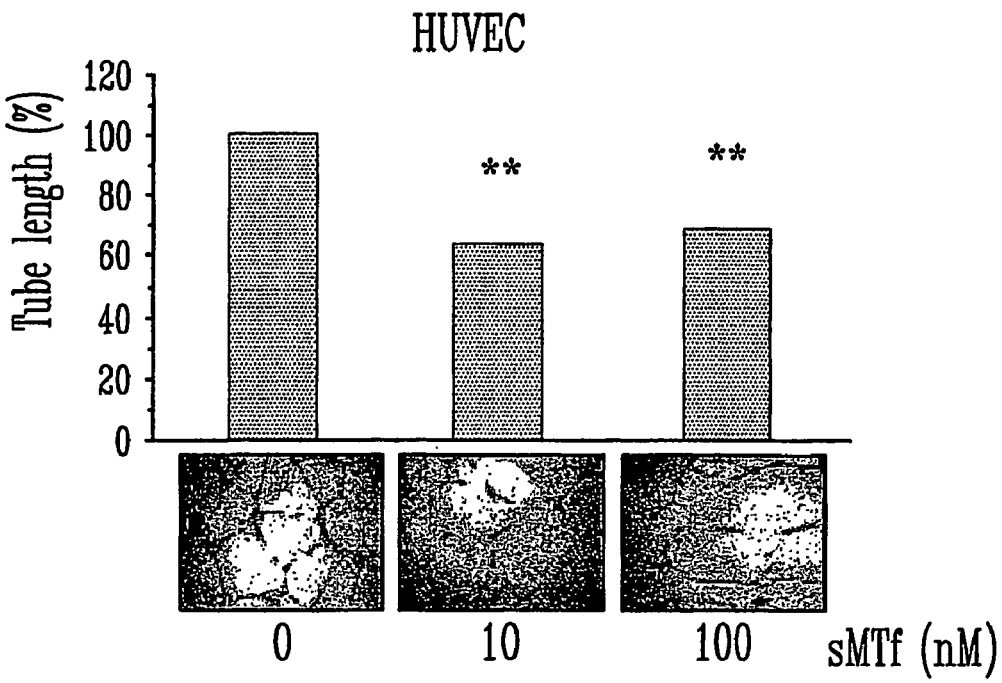

Soluble p97 Inhibits the Morphogenic Differentiation of EC Into Capillary-like Structures The process of angiogenesis is associated with the morphogenic differentiation of EC into microvascular capillary-like structures. To investigate this crucial step of angiogenesis, many studies have used an in vitro assay for tube formation on Matrigel. In the present invention, HMEC-1 and HUVEC cells growth on Matrigel generated a stabilized network of capillary-like structures. This is shown by the complexity of the tubular network per field in control cells observed after 18 hours. The effects of exogenous soluble p97 on HMEC-1 and HUVEC morphogenic differentiation was therefore determined into capillary-like structures (FIG. 11). The generation of capillary-like tubular structure was strongly reduced when soluble p97 was added during the experiments. Indeed, soluble p97 at 10 and 100 nM reduced, by 53% and 47%, the capillary-like tube formation of HMEC-1 (FIG. 11A) and reduced, by 38% and 35%, the capillary-like tube formation of HUVECs (FIG. 11B). These results indicate that soluble p97 inhibits the initiation of capillary-like tube formation. In FIGS. 11A to 11C, data represent the means±SD of results obtained from three different experiments performed in triplicates. Statistically significant differences are indicated by $p<0.01$, *$p<0.001$ (Student's t-test). Photos (original magnification, ×40) obtained from a representative experiment are shown.

Soluble p97 Modulates HMEC-1 Cell Migration

Figure 12A:
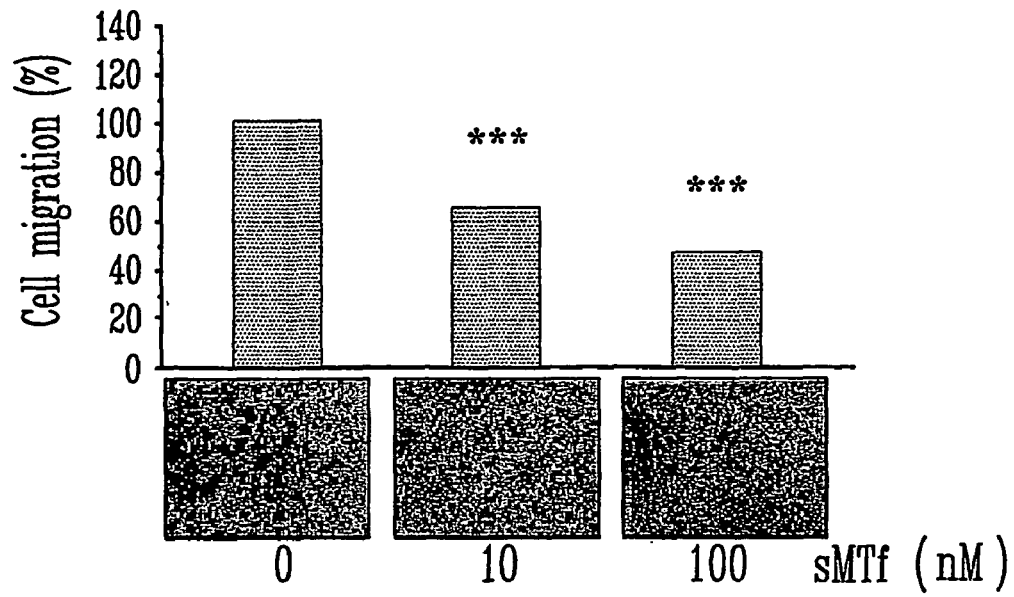
FIG. 12 illustrates that soluble p97 inhibits HMEC-1 cell migration (12A and 12B) without affecting cell adhesion (12C)
Figure 12B:
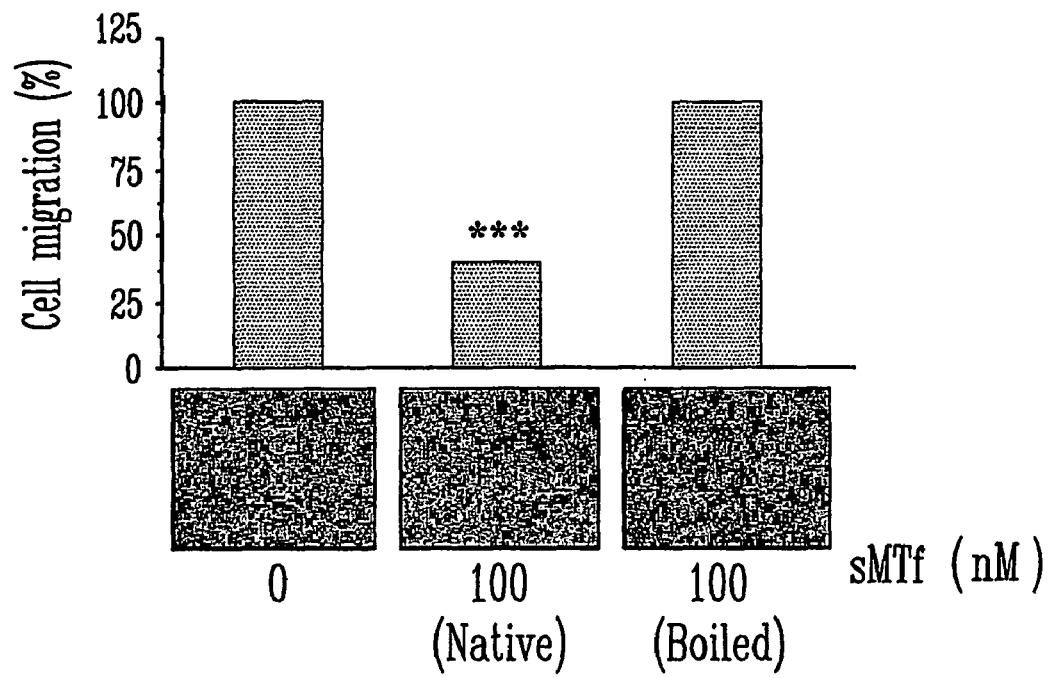
Figure 12C:
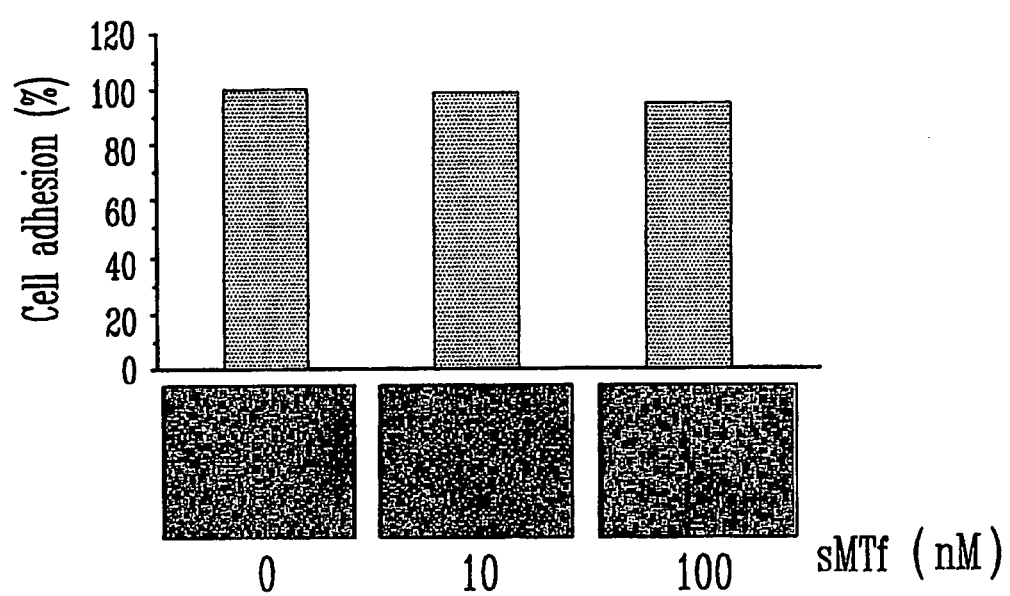

Since soluble p97 affected plasminogen activation, it first investigated whether soluble p97 might modulate cell migration. Using modified Boyden chamber, HMEC-1 cell migration was examined in the presence of soluble p97 (FIG. 12A) soluble p97, at 10 and 100 nM, inhibited the migration of HMEC-1 by 34% and 50%, respectively. The inhibition of HMEC-1 cell migration is completely lost when soluble p97 was boiled for 30 minutes at 100° C. prior to the migration assay (FIG. 12B). This result indicates that a native conformation of soluble p97 is required to inhibit HMEC-1 cell migration. The adhesion of HMEC-1 on gelatin was found unaffected by soluble p97 (FIG. 12C), indicating that the inhibition of cell migration is unrelated to a reduction of adhesive properties. In FIG. 12A), HMEC-1 cell migration was performed using modified Boyden chambers as described in the Materials and Methods sections. Cells that had migrated in the presence or absence of soluble p97 to the lower surface of the filters were fixed, stained with crystal violet and counted. Results are expressed as a percentage of migration in soluble p97-treated cells compared to untreated cells. Data represent the means±SD of four independent experiments performed in triplicates. (B) HMEC-1 cell migration was performed as indicated previously with native or boiled soluble p97. Data represent the means±SD of two independent experiments performed in triplicates. (C) HMEC-1 cell adhesion was performed on gelatin as described in the Materials and Methods sections. Cells that had adhered to the gelatin in the presence or absence of soluble p97 were stained with crystal violet. Results are expressed as a percentage of adhesion in soluble p97-treated cells compared to untreated cells. Data represent the means±SD of three independent experiments performed in triplicates. In all experiments, statistically significant differences are indicated by ***$p<0.001$ (Student's t-test)(original magnification, ×100).

Soluble p97 Up-regulates u-PAR and LRP Protein Expression

Figure 13A:
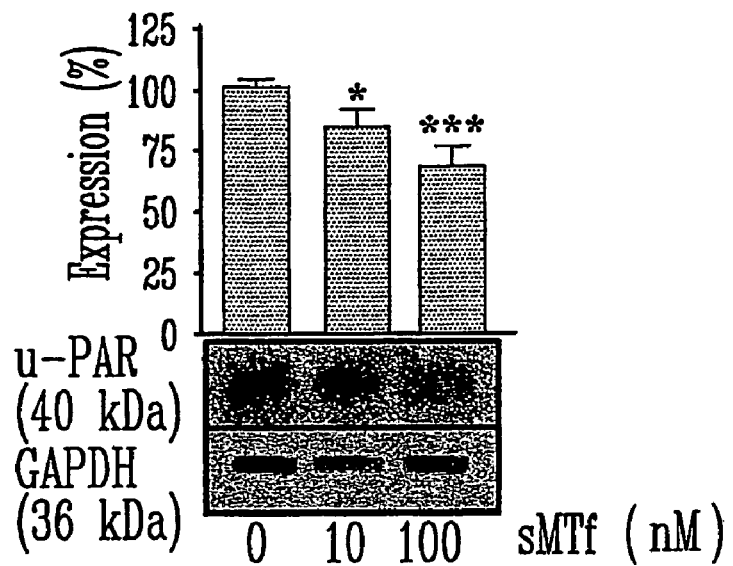
FIG. 13 illustrates that soluble p97 down-regulates u-PAR (13A) and LRP protein (13B) expression.
Figure 13B:
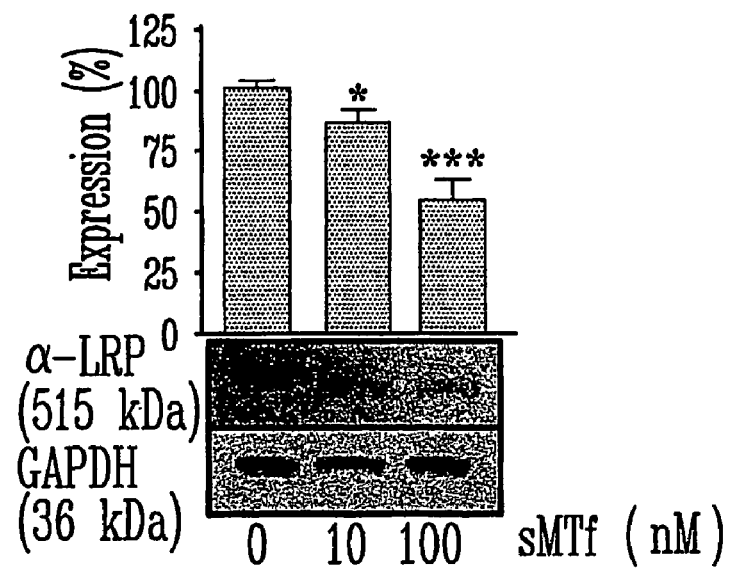

To identify a potential mechanism by which soluble p97 inhibited in vitro EC migration and tubulogenesis, the effect of soluble p97 on the protein expression of both the u-PAR system and LRP was measured by Western blot (FIG. 13). HMEC-1 cells were incubated for 18 hours with or without soluble p97. GAPDH was immunodetected to ensure that the protein content between samples was equivalent. Soluble p97 treatment significantly down-regulated u-PAR and LRP expression. In fact, exposure of HMEC-1 to soluble p97 at 10 and 100 nM reduced u-PAR expression in cell lysates by 20% and 40%, respectively (FIG. 13A). The same concentrations decreased LRP expression by 20% and 50%, respectively (FIG. 13B). In FIGS. 13A and 13B, HMEC-1 were treated for 18 hours with or without soluble p97. Following this treatment, proteins from cell lysates were resolved by SDS-PAGE. Immunodetections of u-PAR (13A) and LRP (13B) were performed as described in the Materials and Methods section. Results were expressed as a percentage of protein expression detected in soluble p97-treated cells compared to untreated cells. Data represent the means±SD of results obtained from three different experiments. Statistically significant differences are indicated by *$p<0.05$, ***$p<0.001$ (Student's t-test).

Soluble p97 Unaffects the u-PAR/LRP System mRNA Expression

Figure 14:
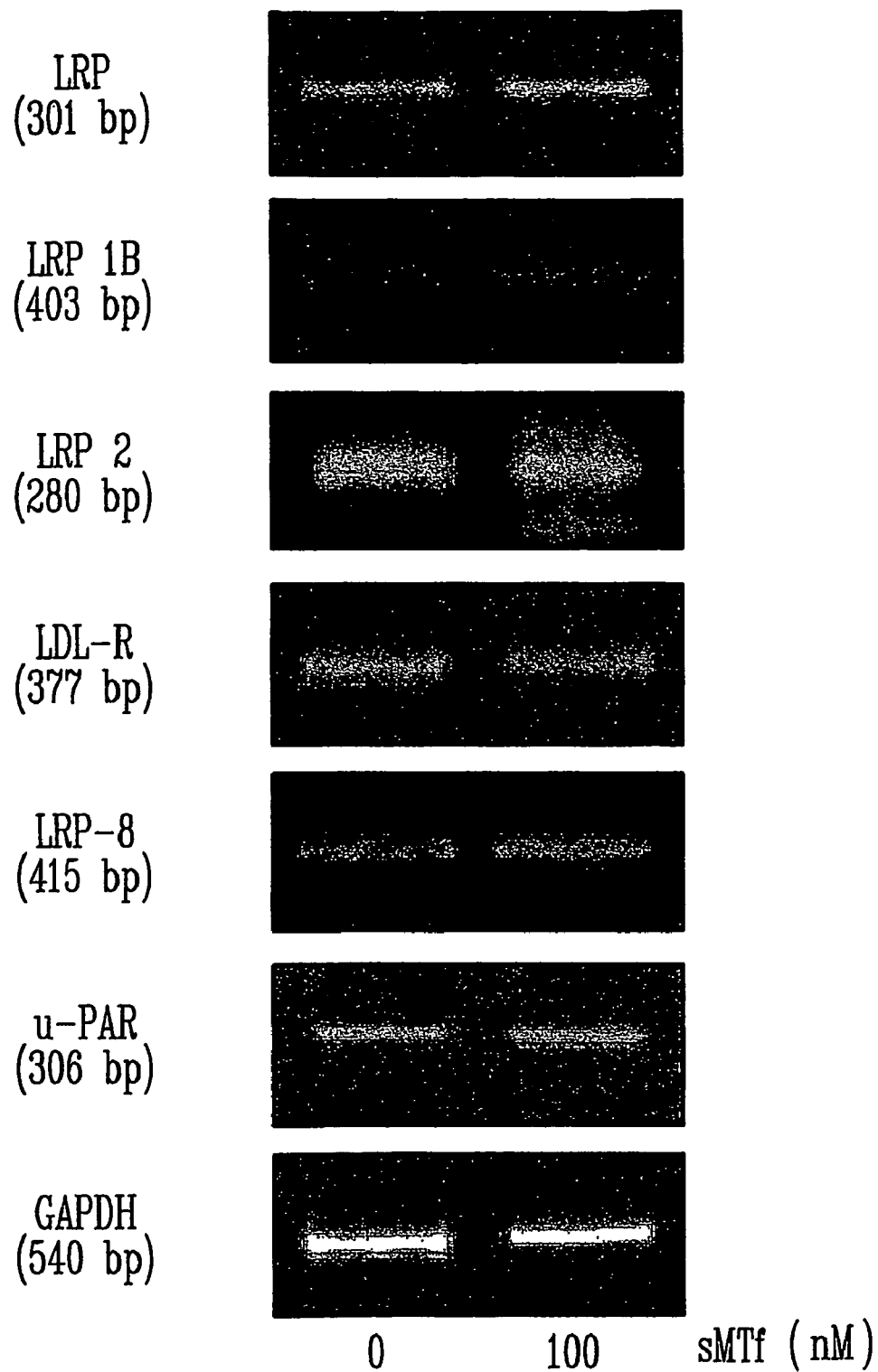
FIG. 14 illustrates that soluble p97 unaffects the u-PAR/LRP system mRNA expression.

Since soluble p97 modulated u-PAR and LRP protein expression, the mRNA expression of LDL-R family gene and u-PAR were estimated by RT-PCR in HMEC-1 treated or not with soluble p97 (FIG. 14). In FIG. 14, HMEC-1 were treated for 18 hours with or without soluble p97. Total RNA was isolated from HMEC-1 and gene products were amplified by RT-PCR as described in the Materials and Methods section. Table 4 shows the primer sequences used for specific cDNA amplification. Expression of the different members of the LDL-receptor family was first investigated in untreated HMEC-1 cells. Under the conditions used for RT-PCR analysis, LRP, LRP 1B, LDL-R and LRP 8 were clearly amplified (35 cycles) whereas LRP 2 and LRP 5 products were almost undetectable. Following soluble p97 treatment, the mRNA levels of LRP, LRP 1B, LRP 2, LDL-R, LRP 8 or u-PAR was unchanged in treated cells as compared to control cells (FIG. 14). An internal control, GAPDH mRNA, was also unaffected by soluble p97. Since u-PAR and LRP gene expression were unaffected by soluble p97, these results indicate that soluble p97 effects on u-PAR and LRP expression takes place at the protein level.

Soluble p97 Modulates the Cell Surface Levels of u-PAR and LRP

Figure 15A:
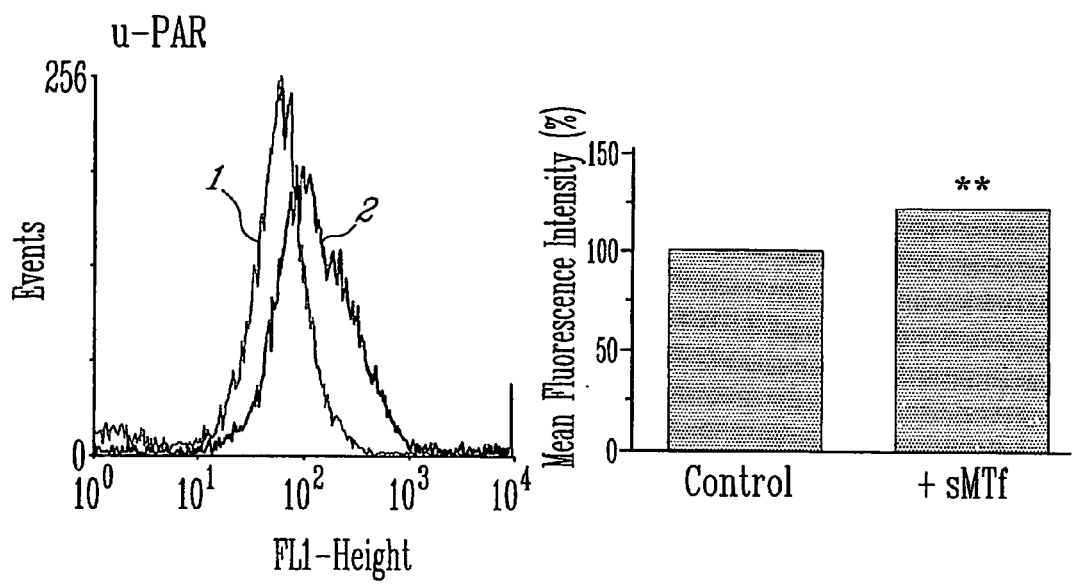
FIG. 15 illustrates that soluble p97 modulates the cell surface levels of u-PAR (15A) and LRP (15B) and binding of 1251-uPA·PAI-1 (15C) complex on the HMEC-1 cell surface.
Figure 15B:
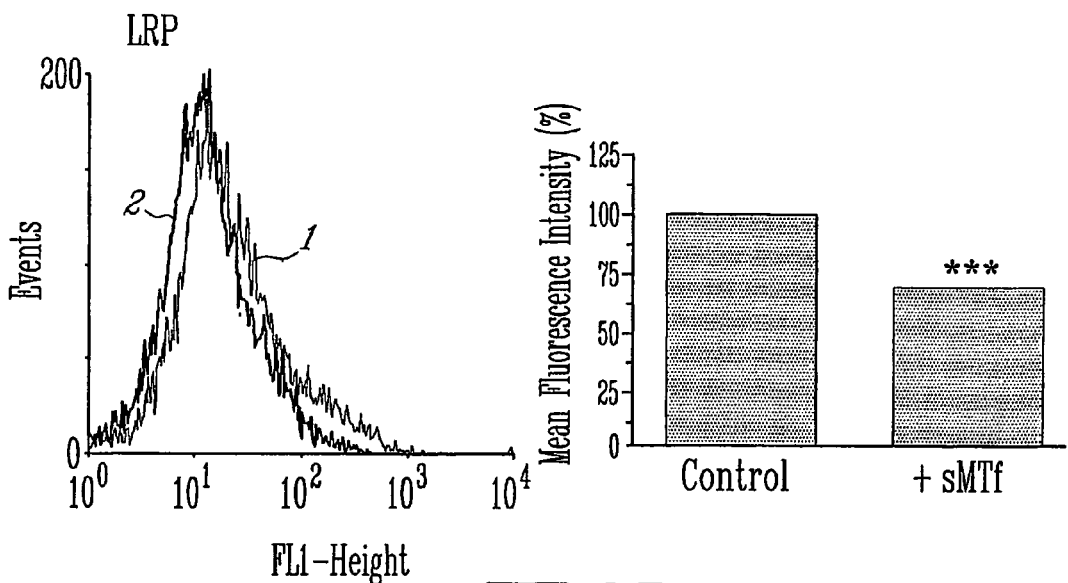

In view of the fact that u-PAR and LRP expression is affected by exogenous soluble p97 and that the amount of u-PAR and LRP at the membrane surface is a key element in plasmin formation, the u-PAR and LRP levels at the cell surface was determined by FACS analysis following soluble p97 treatment (FIGS. 15A and 15B). HMEC-1 cells were incubated for 18 hours with or without 100 nM of soluble p97. Flow cytometric analysis of cell surface u-PAR (15A) and LRP (15B) levels was performed as described in the Materials and Methods section. Control (grey line: 1) or treated HMEC-1 (bold line: 2) were labeled with anti-u-PAR antibody (#3937) or with anti-α-LRP antibody (clone 8G1) and detected with goat anti-mouse IgG-Alexa488. These results are representative of three different experiments. Results were corrected for the background fluorescence intensity measured with a non-specific IgG1 and expressed as mean fluorescence intensities. Data represent the means±SD of three different experiments. Statistically significant differences are indicated by p<0.001, *p<0.001 (Student's t-test). The mean fluorescence intensity associated with the detection of cell surface u-PAR is significantly higher by 25% following soluble p97 treatment. Cell surface LRP expression was also assessed by FACS analysis as in control (grey line: 1) and treated cells (bold line: 2) (FIG. 15B).

Figure 15C:
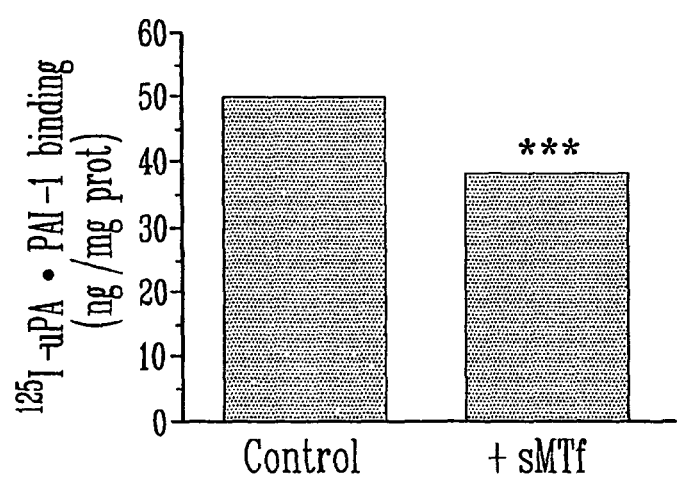

In FIG. 15C, following cell treatment with soluble p97, binding of $^{125}$I-uPA·PAI-1 complex was performed as described in the Materials and Methods section. Data represent the means±SD of three different experiments. Statistically significant differences are indicated by ***p<0.001 (Student's t-test).

The mean fluorescence intensity associated with the detection of cell surface LRP is significantly lower by 30% following soluble p97 treatment. These results-suggest that soluble p97 treatment significantly increased u-PAR levels and decreased LRP levels at the cell surface of HMEC-1. To find out whether u-PAR at the cell membrane of HMEC-1 soluble p97-treated cell is free or occupied by u-PA and/or uPA·PAI-1 complex, a binding assay of $^{125}$I-uPA·PAI-1 complex on HMEC-1 following soluble p97 treatment (FIG. 15C) was next performed. HMEC-1 were incubated for 18 hours with or without soluble p97 and the binding of $^{125}$I-uPA·PAI-1 complex was then measured at 4° C. in control and treated cells. The cell associated radioactivity after the binding of $^{125}$I-uPA·PAI-1 complex was reduced by about 23% following soluble p97 treatment. This result suggest that the free u-PAR at the cell membrane was decreased after soluble p97 treatment.

Soluble p97 Up-Regulates Cav-1 and Down-Regulates pERK 1/2 Protein Expression.

Figure 16A:
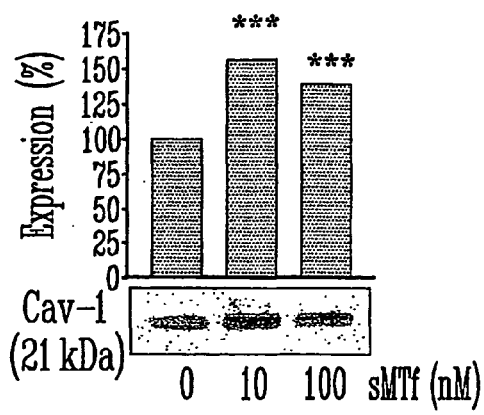
FIG. 16 illustrates that soluble p97 up-regulates Cav-1 (16A) and down-regulates pERK 1/2 (16D) protein expression and wherein the level in control cells (16B) and ERK 1/2 (16C) was unchanged.
Figure 16B:
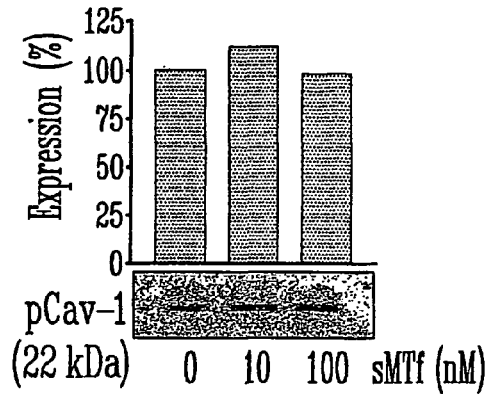
Figure 16C:
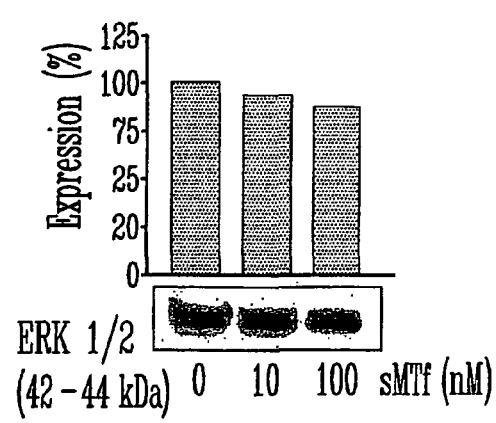
Figure 16D:
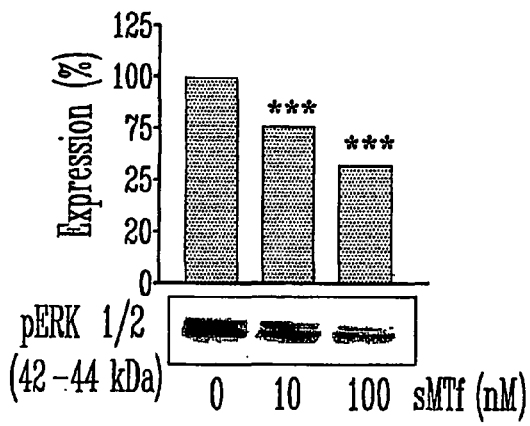

To further understand the effects of soluble p97 on in vitro EC migration and tubulogenesis, the expression and phosphorylation levels of proteins associated with angiogenesis (FIGS. 16 and 17) was next measured. In this invention, HMEC-1 were incubated for 18 hours with or without soluble p97 (10 or 100 nM). Following this treatment, proteins from cell lysates were solubilized and resolved by SDS-PAGE. Immunodetection of Cav-1 (16A) and pCav-1 (16B) as well as ERK 1/2 (16C) and pERK 1/2 (16D) was performed as described in the Materials and Methods section. Results were expressed as a percentage of protein expression detected in soluble p97-treated cells compared to untreated cells. Data represent the means±SD of results obtained from three different experiments. Statistically significant differences are indicated by ***p<0.001 (Student's t-test). Since Cav-1 play an important positive role in the regulation of EC differentiation, a prerequisite step in the process of angiogenesis, the effects of soluble p97 on the structural protein Cav-1 and its tyrosine phosphorylated state (pCav-1) was examined by Western blot analysis (FIGS. 16A and 16B). The Cav-1 level was increased by 50% and 37% following soluble p97 treatment in HMEC-1 at 10 and 100 nM, respectively (FIG. 16A). The pCav-1 levels remained however unchanged in soluble p97-treated HMEC-1 as compared to control cells (FIG. 16B). Because Cav-1 has been previously implicated as a tonic inhibitor of the ERK 1/2 MAP kinase cascade involved in angiogenesis, the effects of soluble p97 on ERK 1/2 protein expression and phosphorylation levels was evaluated by Western blot analysis (FIGS. 16C and 16D). The ERK 1/2 level was unchanged following soluble p97 treatment in HMEC-1 (FIG. 16C). In contrast, the pERK 1/2 level was significantly decreased by 25% and 40% following soluble p97 treatment in HMEC-1 at 10 and 100 nM (FIG. 16D), respectively. Thus, these results show that soluble p97 affects differently the expression of Cav-1 and ERK 1/2, two proteins involved in the setting of angiogenesis.

Soluble p97 Down-regulated eNOS Protein Expression as Well as VEGFR-2 and VEGF-A mRNA Expression.

Figure 17A:
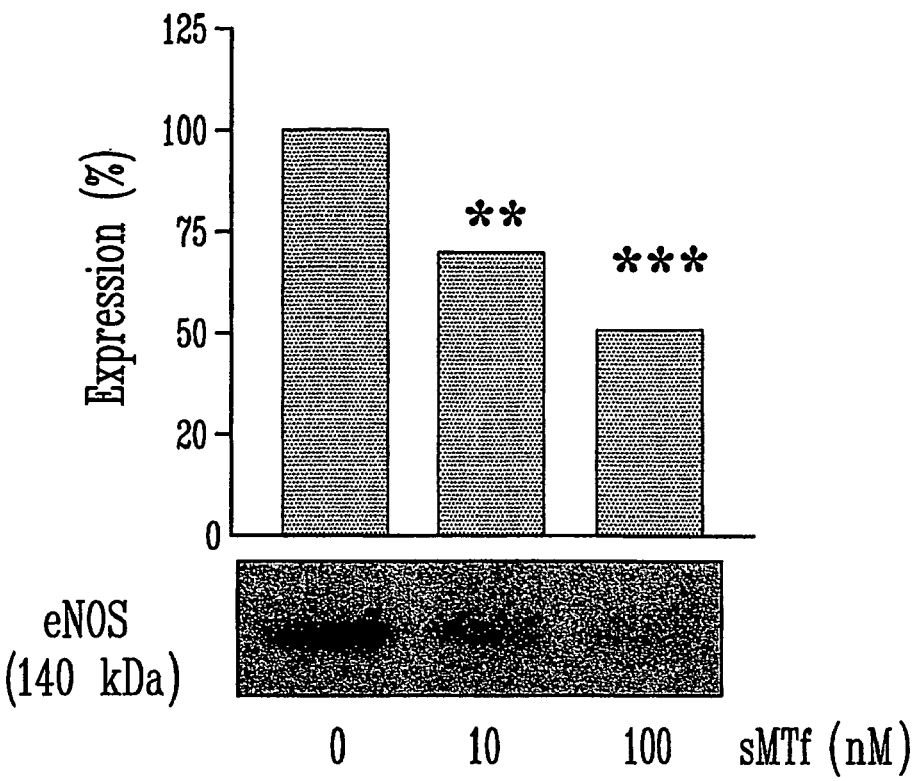
FIG. 17 illustrates that soluble p97 down-regulates eNOS protein expression (17A) as well as VEGFR-2 and VEGF-A mRNA levels (17B)
Figure 17B:
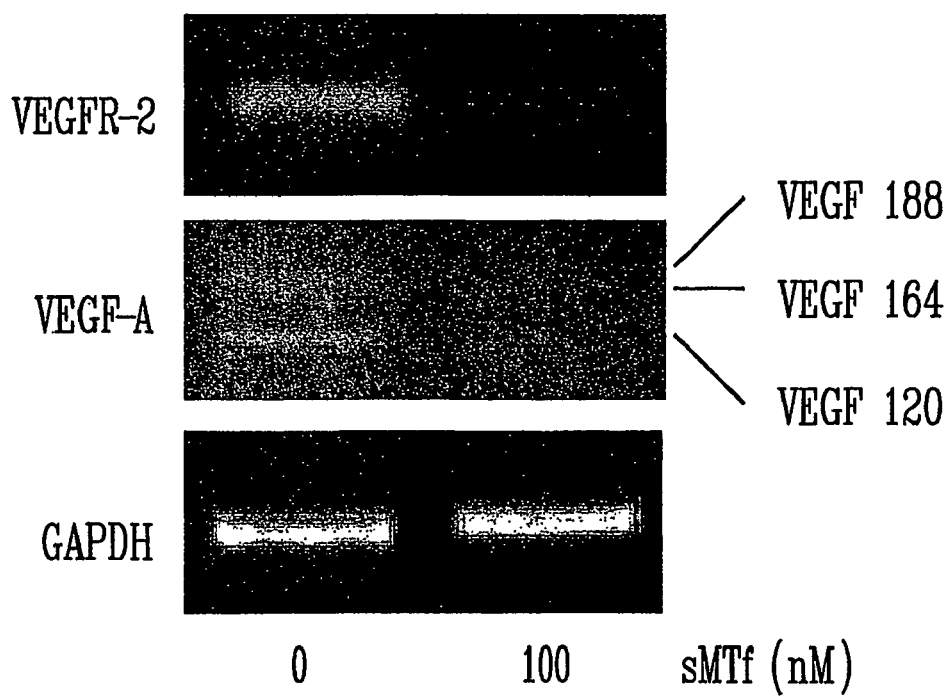

Cav-1 is also known to be an endogenous inhibitor of eNOS, a protein related to many physiological and pathological functions, including angiogenesis. Since soluble p97 modulates Cav-1 expression, the effect of soluble p97 on eNOS protein expression was assessed by Western-blot analysis (FIG. 17A). Soluble p97, at 10 and 100 nM, reduced eNOS levels by about 30% and 50%, respectively. In FIGS. 17A and 17B, HMEC-1 were treated for 18 hrs with or without soluble p97. Following treatment, proteins from cell lysates were solubilized and resolved by SDS-PAGE. Immunodetection of eNOS (17A) was performed as described in the Materials and Methods section. Results were expressed as a percentage of protein expression detected in soluble p97-treated cells compared to untreated cells. Data represent the means±SD of results obtained from three different experiments. Statistically significant differences are indicated by p<0.01, *p<0.001 (Student's t-test).

Furthermore, eNOS has been suggest to play a predominant role in VEGF-induced angiogenesis. Because immunodetected levels of eNOS are reduced in soluble p97-treated HMEC-1 cells, the effect of soluble p97 on the mRNA levels of VEGF-A and its receptor, the VEGFR-2 (FIG. 17B) was estimated by RT-PCR. Following an incubation of 18 hours with or without 100 nM soluble p97, soluble p97 reduced VEGFR-2 and VEGF-A mRNA levels in HMEC-1 cells. In FIG. 17B, following treatment, total RNA was isolated from HMEC-1 and gene products were amplified by RT-PCR as described in the Materials and Methods section. Results obtained from a representative experiments are shown (N=3). These results indicate that soluble p97 affects the expression of key players associated with angiogenesis, including the protein expression levels of eNOS as well as the mRNA levels of VEGFR-2 and VEGF-A.

Figure 18:
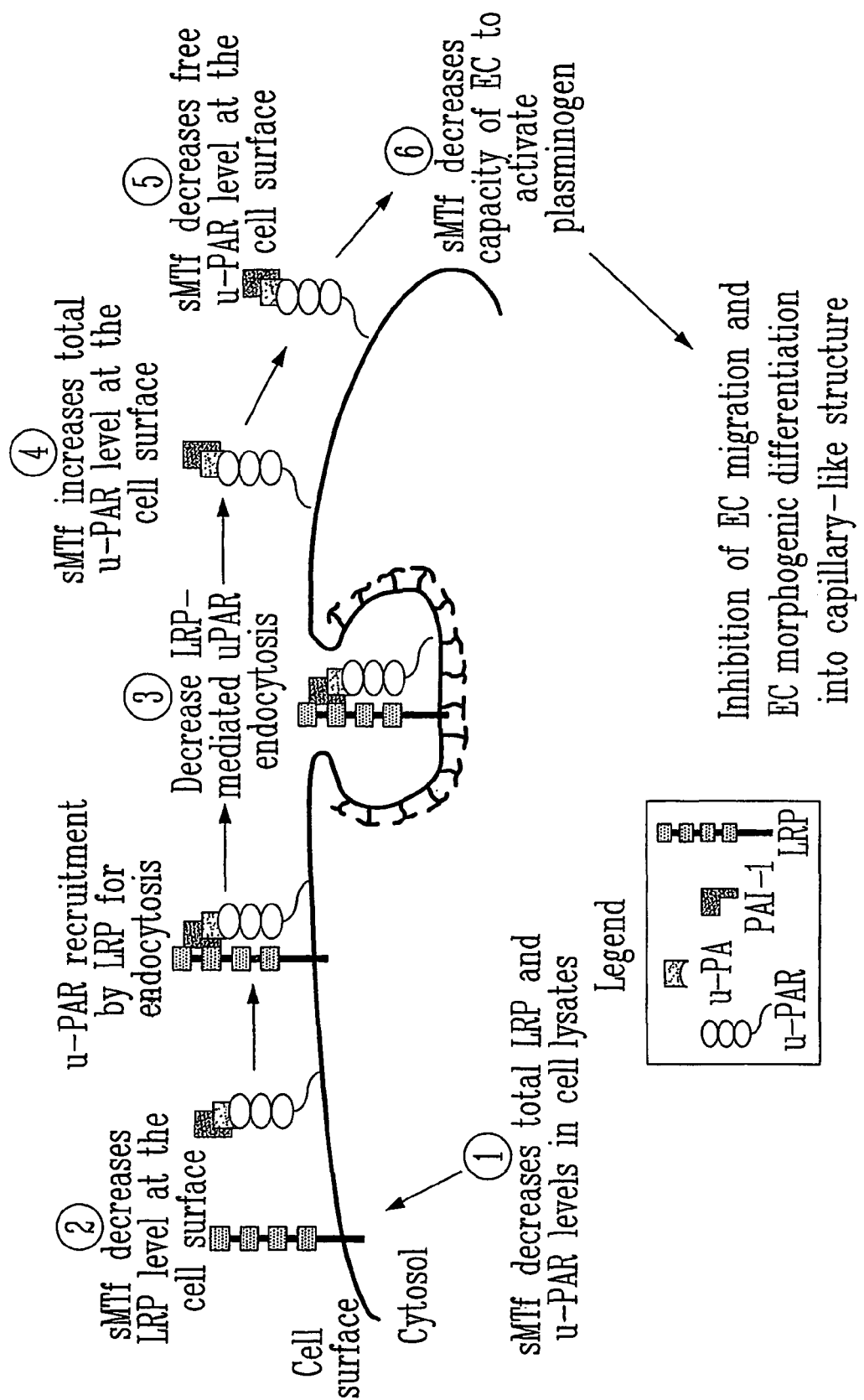
FIG. 18 is a schematic representation of soluble p97 treatment effects on the u-PAR/LRP system.

The results presented herein suggest a mechanism by which soluble p97 inhibits HMEC-1 cell migration as well as HMEC-1 and HUVEC capillary-like tube formation. Soluble p97 could affect the turn-over of LRP and u-PAR leading to a decreased capacity of plasminogen activation at the cell surface (FIG. 18). In addition, soluble p97 treatment affects EC phenotype by affecting Cav-1, pERK 1/2, eNOS, VEGF-A and VEGFR-2.

In FIG. 18, the schematic representation summarizes the results obtained in the present study after soluble p97 treatment. ① soluble p97 treatment decreases the total u-PAR and LRP expression levels in cell lysates, as assessed by Western-blotting. ② Since the total LRP levels decreased, the cell surface level of LRP also decrease. It is well established that LRP mediates the internalization of u-PAR. ③ Since cell surface LRP levels decreased, it was postulated that the LRP-mediated endocysosis of u-PAR also decreased. ④ The diminished rates of u-PAR endocytosis increased the total u-PAR level at the cell surface, as assessed by FACS analysis. ⑤ Since u-PAR is not internalized by LRP, soluble p97 decreased the free u-PAR level at the cell surface. ⑥ The decreases free u-PAR level at the cell surface lead to a decreased capacity of EC to activate plasminogen. The net effect of soluble p97 treatment on the u-PAR/LRP system lead to an inhibition of EC migration and morphogenic differentiation of EC into capillary-like structure.

Figure 19A:
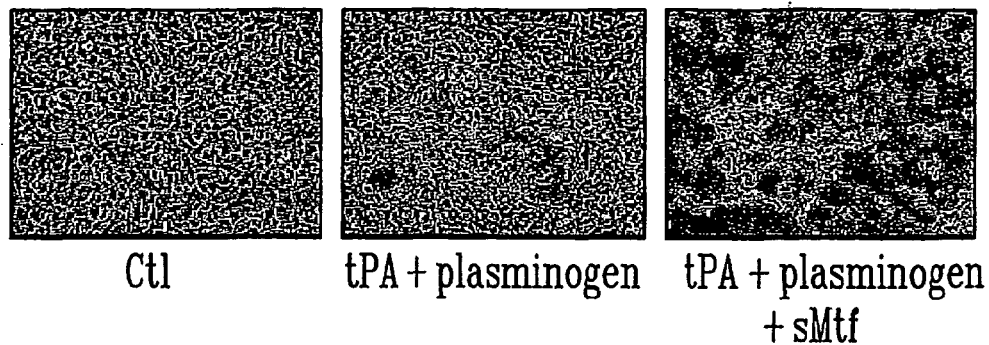
FIG. 19 illustrates that soluble p97 enhance cell detachment (19A), plasminolytic activity (19B) and plasmin formation in HEMEC-1 (19C)
Figure 19B:
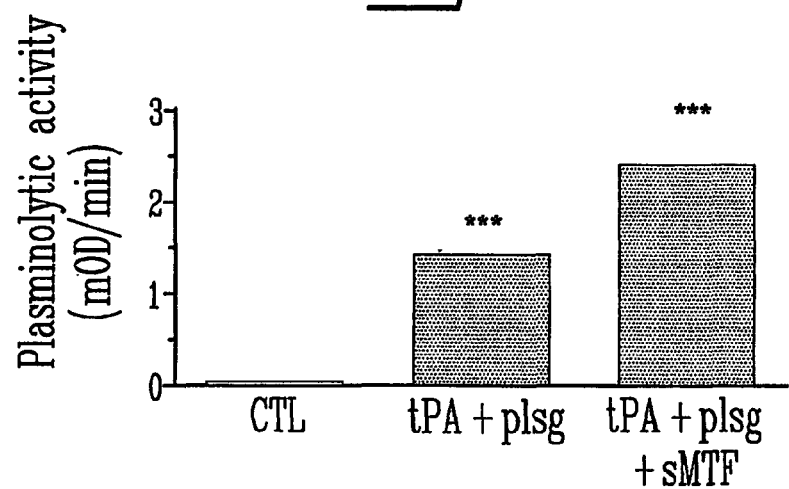
Figure 19C:
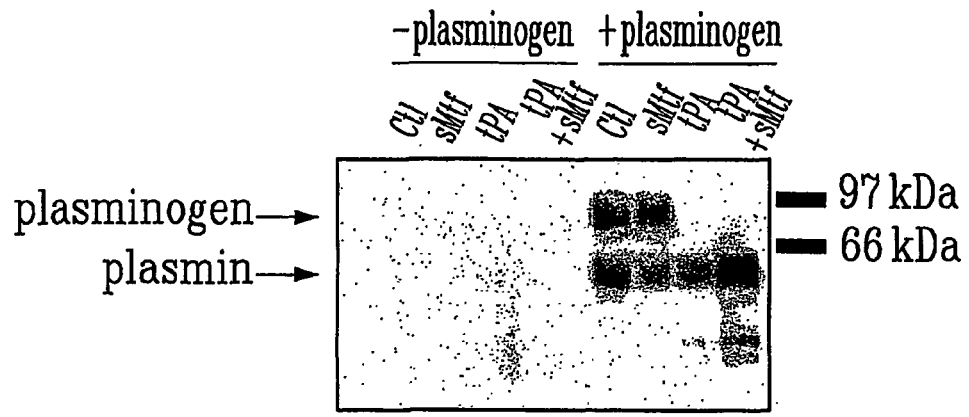

Soluble p97 Causes Endothelial Cell Detachment and Extracellular Matrix Degradation So far, It has been shown herein that soluble p97 stimulates plasminogen activation both in vitro and on endothelial cells. Increased plasmin formation has been implicated in endothelial cell detachment. Therefore, the effects of soluble p97 on endothelial cell adhesion in the absence and presence of plasminogen (FIG. 19) was studied. While soluble p97 or plasminogen alone did not induce cell detachment, co-treatment of the endothelial cells with plasminogen, tPA and soluble p97 resulted in an increase cell detachment compared to control or tPA and plasminogen combination (FIG. 19A). The plasminolytic activity measured in FIG. 19B, showed that it is strongly increased when soluble p97 is added to tPA and plasminogen. Immuodetections of plasminogen and plasmin (FIG. 19C) indicate that the addition of soluble p97 increases the generation of plasmin which lead to matrix degradation and cell detachment. In FIG. 19, addition of soluble p97 stimulates HMEC-1 detachment (19A) and plasminolytic activity in cell media (19B) in presence of plasminogen and tPA. Photos (original magnification, ×100) obtained from a representative experiment are shown. In FIG. 19C, following the treatment with or without soluble p97, proteins from cell media were resolved by SDS-PAGE and immunodetection of plasminogen and plasmin was performed as described in the Materials and Methods section. Immunodetections obtained from a representative experiment are shown. Results were expressed as a percentage of protein expression detected. Data represent the means±SD of results obtained from three different experiments. Statistically significant differences are indicated by $*p<0.05$, $***p<0.001$ (Student's t-test).

Figure 20A:
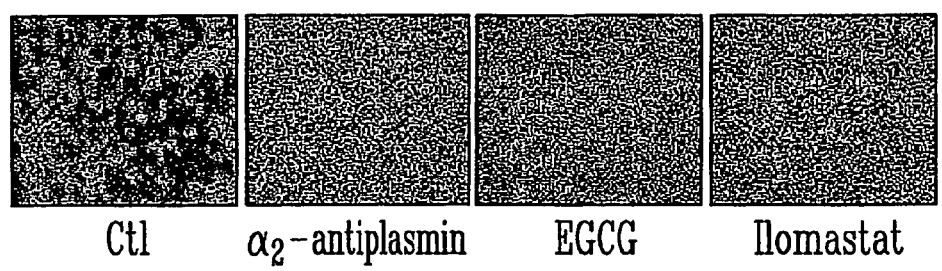
FIG. 20 illustrates inhibition of cell detachment (20A) and plasmin formation (20B) by inhibitors.
Figure 20B:
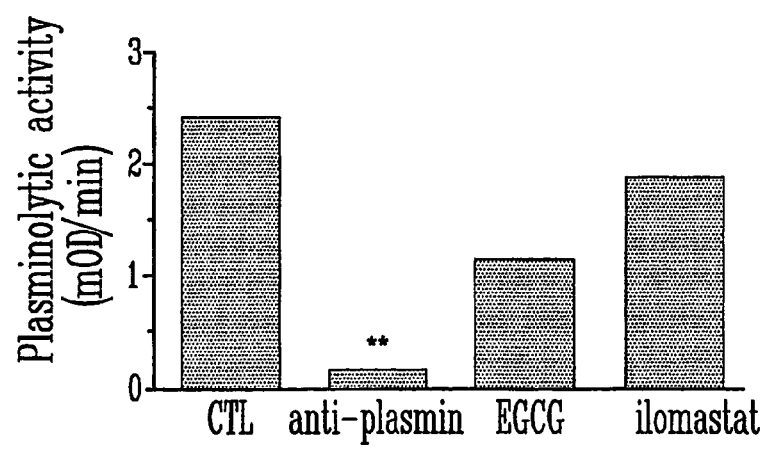

Inhibitors of plasmin (alpha2-antiplasmin) and MMPs (EGCG and Ilomastat) block the effects of soluble p97 on endothelial cell detachment (FIG. 20A). In FIG. 20A, HMEC-1 detachment was performed in presence of three different inhibitors, namely, α2-antiplasmin, EGCG, and ilomastat. Photos (original magnification, ×100) obtained from a representative experiment are shown. In FIG. 20B, following the treatments, plasminolytic activity in cell media was measured as described in the Materials and Methods section. Data represent the means±SD of results obtained from three different experiments. Statistically significant differences are indicated by $*p<0.05$, $***p<0.001$ (Student's t-test). The observed detachment of endothelial cells is mediated by extracellular matrix degradation. As an important component of the extracellular matrix involved in cell attachment, fibronectin is degraded by MMPs.

Figure 21:
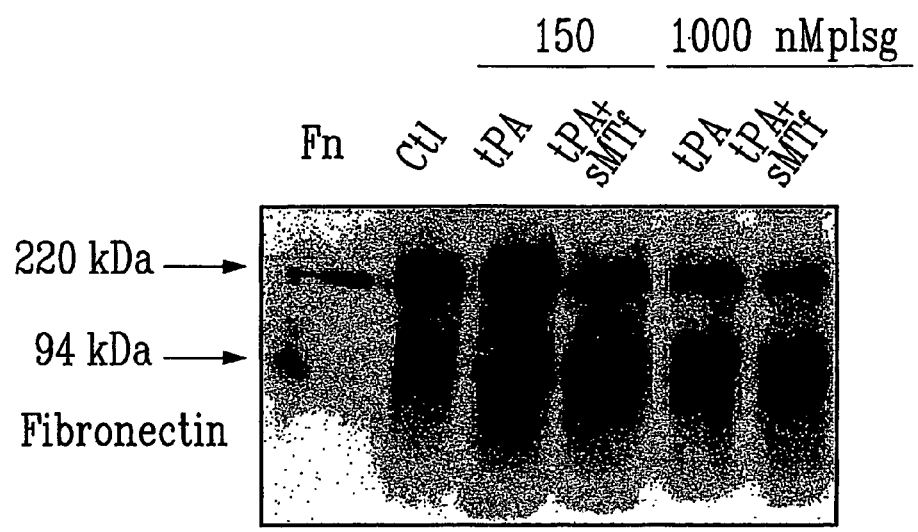
FIG. 21 illustrates that cell detachment stimulated by soluble p97 induces degradation of fibronectin in HMEC-1.

Fibronectin degradation was studied in lysates of soluble p97-treated endothelial cells by Western blotting. Whereas only small amounts of fibronectin degradation products were generated in the presence of plasminogen alone, co-treatment with tPA and soluble p97 potently increased fibronectin degradation (FIG. 21). In FIG. 21, HMEC-1 lysate from soluble p97 stimulated detachment were resolved by SDS-PAGE and immunodetection of fibronectin was performed as described in the Materials and Methods section. Immunodetections obtained from a representative experiment are shown. Results were expressed as a percentage of protein expression detected.

Overall, these results (FIGS. 20 and 21) indicate that soluble p97 stimulates plasmin- and MMP-dependent endothelial cell detachment.

Consequently, these are the first data indicating that exogenous human recombinant soluble p97 have anti-angiogenic properties, by affecting the morphogenic differentiation of EC into capillary-like structures, by interfering with key proteins involved in angiogenesis and by inducing EC detachment.

Example VIII

Melanotransferrin Increases Human Blood Clot tPA-Fibrinolysis

Figure 22:
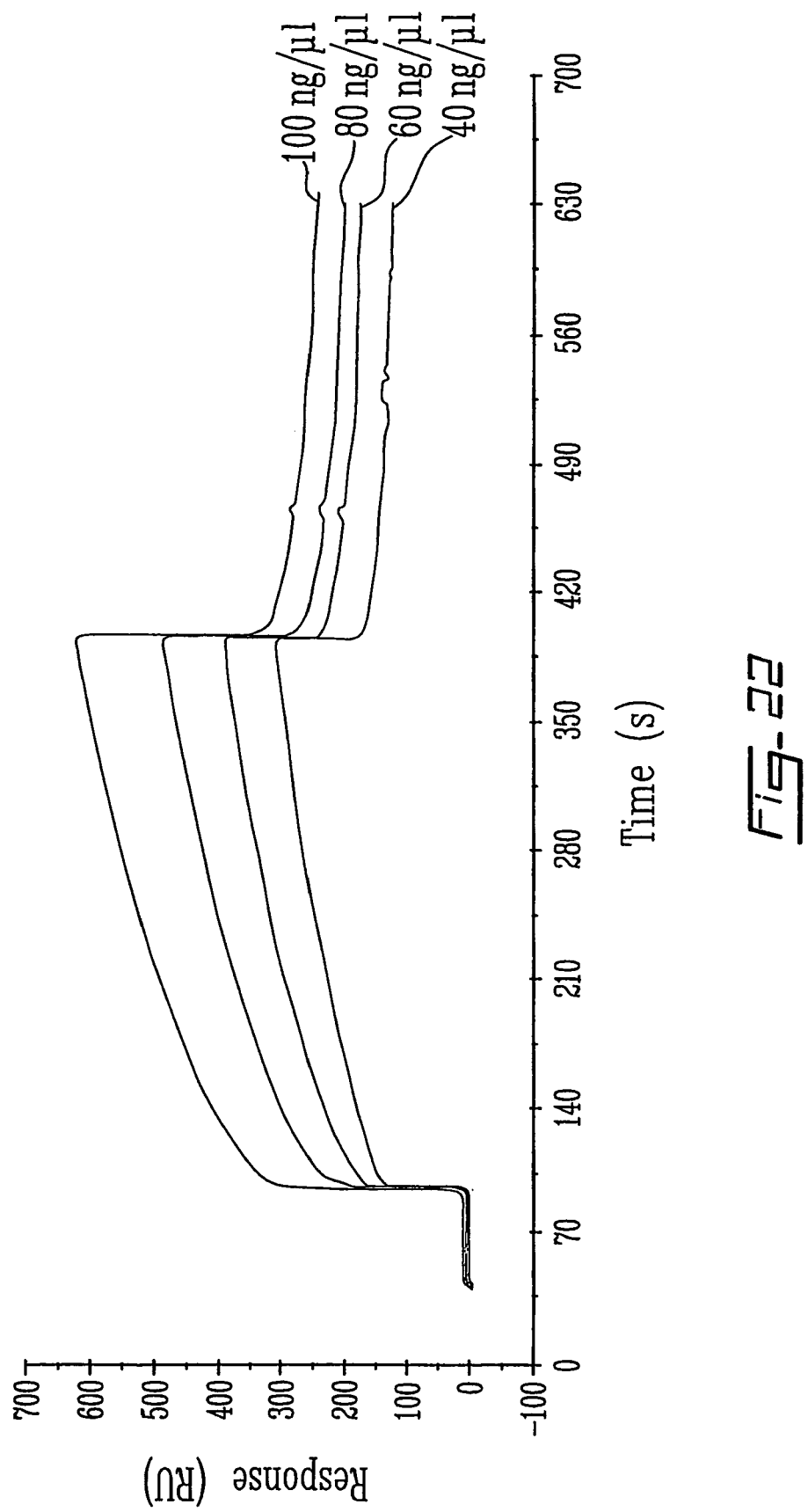
FIG. 22 illustrates the interaction between p97 and plasminogen using biospecific interaction analysis in real-time.

Regulation of plasminogen is a key element in blood clot fibrinolysis. In the present invention, potential interactions between human recombinant p97 with components of the plasminogen activator system in relation with fibrinolysis were investigated. By using biospecific interaction analysis, it is demonstrated herein that p97 interacts with immobilized plasminogen. Kinetics analysis of the biosensorgrams using two state conformation change model shows an apparent equilibrium dissociation constant $K_D$ of $2.6 \times 10^{-7}$ M for this interaction (FIG. 22). Moreover, soluble p97 increased the tPA-dependent plasminogen activation. This induction by p97 is inhibited by the monoclonal antibody L235 directed against p97 indicating that the increase in the plasminolytic activity is specific to p97 (FIGS. 23A, 23B and 23C). p97 also enhanced the tPA fibrinolysis of plasma and fibrin clots (FIG. 26). The thromboelastography of fibrinolysis and clot strength were evaluated with or without p97 (FIG. 26). Complete lysis time (CLT) was reduced in the IVM (in vitro model) and plasma by 50% and 20% respectively when p97 was added to tPA. There was also a difference in the fibrinolysis by tPA at 30 min (LY30) in both models when p97 was added. The LY30 was enhanced by 5- and 2-fold in both artificial and blood clots, respectively. These results indicates that p97, by interacting with plasminogen, enhanced plasminogen activity by tPA reduced time of thrombolysis. In conclusion, these results demonstrate the potential of the present invention in new treatments of arterial disease and thrombosis and to reduce the damages to occluded hearth tissues.

Interaction Between p97 and Plasminogen Using Biospecific Interaction Analysis in Real-Time Plasminogen was immobilized on BIAcore with standard coupling procedures. Various concentrations of p97 were injected over immobilized plasminogen. The estimated constant of dissociation ($K_D$) estimated from these curves for the interaction between p97 and immobilized plasminogen is 275 nM. The results of this experiment are shown in FIG. 22.

Melanotransferrin (p97) Increases the Plasminogen Activation by Tissue Plasminogen Activator (tPA)

Hydrolysis of the peptide VKL was measured in the presence of p97 alone, tPA and tPA+p97. As shown in FIG. 23A, in the presence of p97 the plasminogen activation by tPA was increased by 4-fold. As shown in FIG. 23C, the plasminogen activation by tPA was increased in a dose-dependent manner by p97 with half-maximal stimulation occurring at 12±3 nM.

Inhibition of the p97 Effect by the Monoclonal Antibody L235

The plasmin activity was measured in the presence of tPA and p97 with the monoclonal antibody directed against p97 (mAb L235) or a non-specific mouse IgG (mouse IgG). As shown in FIG. 23B, the induction caused p97 of the plasminogen activation by tPA is inhibited by the monoclonal antibody directed against p97 indicating that this induction is specific to p97.

p97 Increases Clot Fibrinolysis Induced by tPA

Figure 26A:
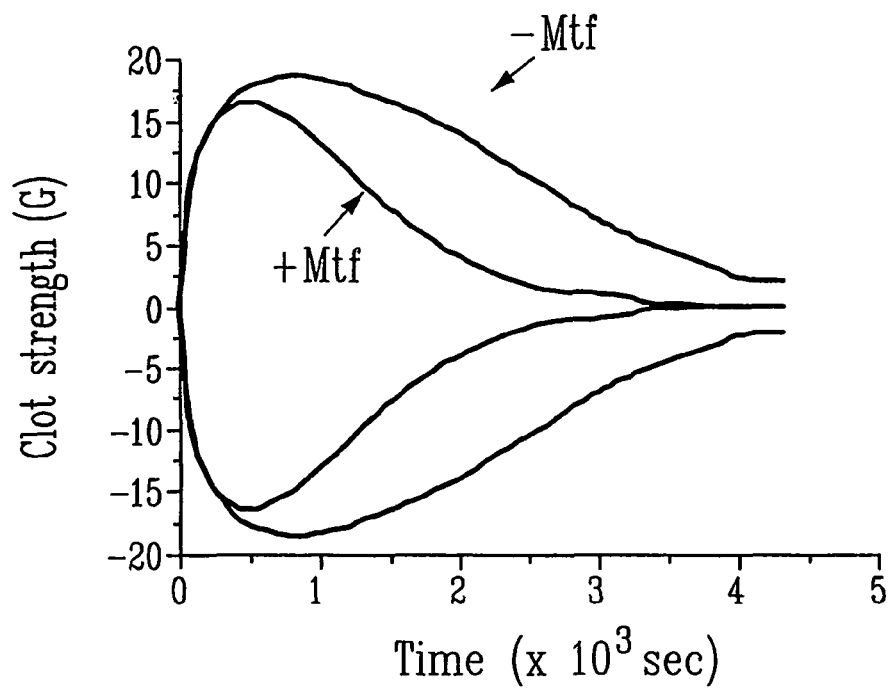
FIG. 26 illustrates the effect of p97 on clot strength and fibrinolysis, and more specifically of a thromboelastogram of a fibrin clot model (26A) and of a plasma recalcified after addition of 2 nM $CaCl_2$ (26B)
Figure 26B:
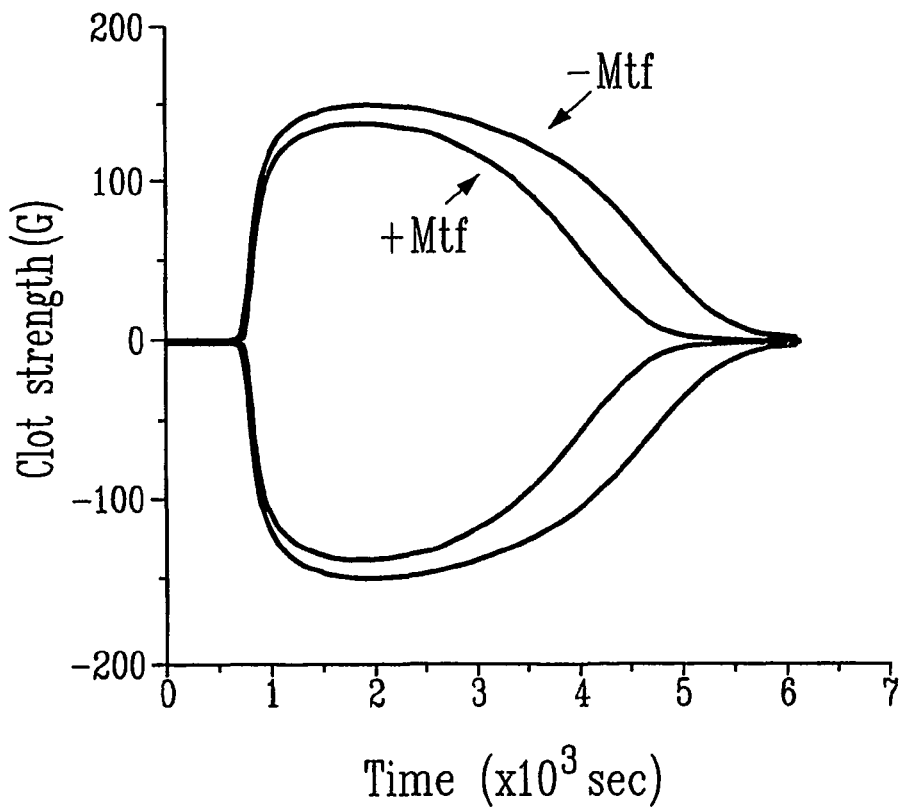

The effect of p97 on fibrinolysis was measured using a thromboelastograph. In the thromboelastography analysis (TEG), 320 µl of citrated plasma or artificial clot model (8.2 µM fibrinogen, 2 µM glu-plasmingen and 0.4 U/ml thrombin) was transferred into analyser cups with tPA (4.5 nM) and in the presence or absence of p97 (1 µM). The cups were placed in computerized dual-channel TEG analyzer (model 5000; Haemoscope Corp., Niles, Ill.). In one of the cups (channel 1), tPA was added, in another cup (channel 2) p97 and tPA were added. All cups containing 20 µl 0.2M $CaCl_2$ were prewarmed to 37° C. and analyzed simultaneously. The TEG variables collected from each sample included: CLT (clot lysis time), G (clot strength or Shear elastic modulus in $dyn/s^2$, defined as G=(5000 A)/(100−A)), LY30 and LY 60 (percent of clot lysis at 30 and 60 min after maximum clot strength is achieved). As shown in FIG. 26A, when p97 was added to the artificial clot, the clot lysis at 30 min was increased by 5-fold. As shown in FIG. 26B, in the presence of p97, the lysis at 30 min of human blood clot by tPA was increased by 2-fold.

Because soluble p97 interacts with glu-plasminogen, the inventors have investigated whether human recombinant p97 might affect fibrinolysis and clot permeation. To show that soluble p97 could modulate fibrinolysis, the impact of human recombinant soluble p97 on plasminogen activation by tPA (FIG. 23A) was first determined. After 180 minutes, the addition of soluble p97 increased by 6-fold the plasminogen activation by tPA measured by the hydrolysis of the VLK-peptide. Soluble p97 alone has no proteolytic or plasmin-like activity. The induction of tPA-dependent plasminogen activation by soluble p97 was also measured in the presence of the mAb L235 directed against soluble p97 or a non-specific IgG (FIG. 23B). The mAb L235, at 50 nM, inhibited by 80% the effect of soluble p97 on plasminogen activation by tPA. These results suggest that the effect of soluble p97 on plasminogen activation is rather specific and involves the conformational epitope recognizes by the mAb L235. In addition, plasmin activities measured as a function of time allowed us to extract initial rates. These rates were plotted as a function of soluble p97 concentrations (FIG. 23C). Soluble p97 stimulated the tPA-dependent conversion of plasminogen to plasmin in a dose-dependent manner with half-maximal stimulation occurring at 53±22 nM. The effect of soluble p97 on plasmin formation by tPA in the presence of various concentrations of plasminogen (FIG. 23D) was further evaluated. Initial rates of plasmin activity plotted as a function of plasminogen concentrations indicate that soluble p97 decreases the apparent $K_m$ of tPA for plasminogen by 5-fold from 280 to 52 nM. In FIG. 23A, the plasminolytic activity of tPA (60 ng) was measured without (○) or with 1 µg/ml p97 (●) in the presence of Plg (0.5 µg). The reaction was performed in a final volume of 200 µl as described in the Materials and Methods section. The plasminolytic activity in the presence of p97 alone was also measured (■). In FIG. 23B, the plasminolytic activity of tPA was measured in the presence of p97 (5 µg/ml) and either the mAb L235 (○) or a non-specific mouse IgG (●). The reaction was performed in a final volume of 200 µl as described in the Materials and Methods section. In FIG. 23C. plasmin activity induced by tPA was determined by measuring VLK-hydrolysis in the presence of various p97 concentrations. In FIG. 23D initial rates of VLK-hydrolysis during Plg activation by tPA were measured without (○) or with 50 nM p97 (●) in the presence of various concentrations of Plg. Data are shown as means of 3 experiments.

To further characterize the soluble p97 effects on the action of tPA in fibrinolysis, the effect of soluble p97 on a radial tPA-fibrinolysis assay (FIG. 24) was evaluated.

Figure 24A:
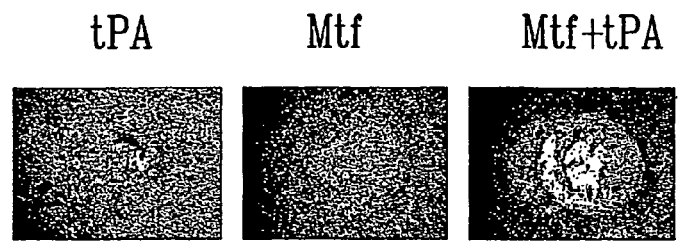
FIG. 24 illustrates fibrin clot permeation in the presence of p97 (24A), the size increase of the perforation as a function of soluble p97 concentration (24B), and the intrinsic fibrinolytic activity of soluble p97 (24C)
Figure 24B:
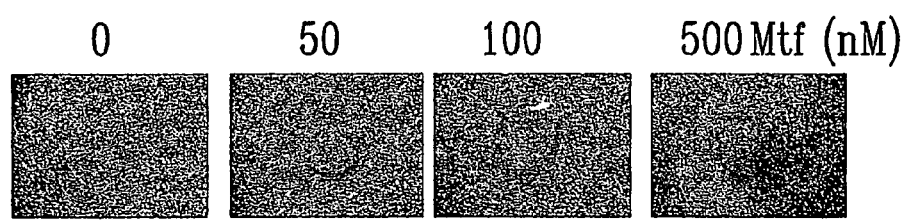
Figure 24C:
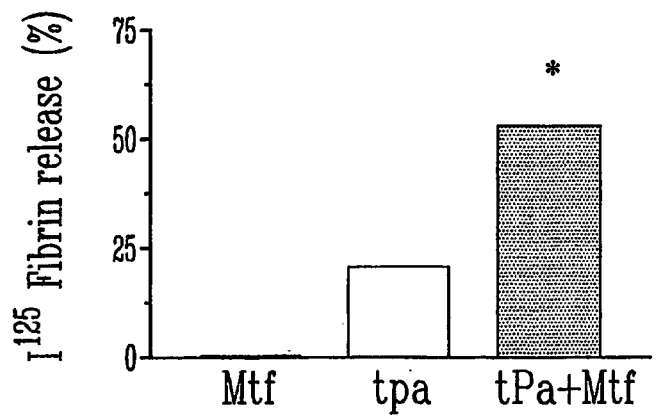

The addition of soluble p97 to tPA enhances its action and leads to an increase perforation of the fibrin-clot (FIG. 24A). Surprisingly, in this experiment performed without tPA, soluble p97 in the presence of plasminogen creates a perforation of the fibrin-clot. Moreover, the size of the perforation increases as a function of soluble p97 concentration (FIG. 24B). In absence of plasminogen and tPA, the fibrin-clot is unaffected by soluble p97 alone. To determine whether soluble p97 has an intrinsic fibrinolytic activity, the release of fibrin fragments from clots labeled with [$^{125}$I]-fibrin (FIG. 24C) was measured. In spite of its ability to perforate the clot, soluble p97 alone does not generate [$^{125}$I]-fibrin fragments. However, soluble p97 in the presence of plasminogen increases the release of [$^{125}$I]-fibrin fragments by 2.5 fold following plasminogen activation by tPA.

Figure 25:
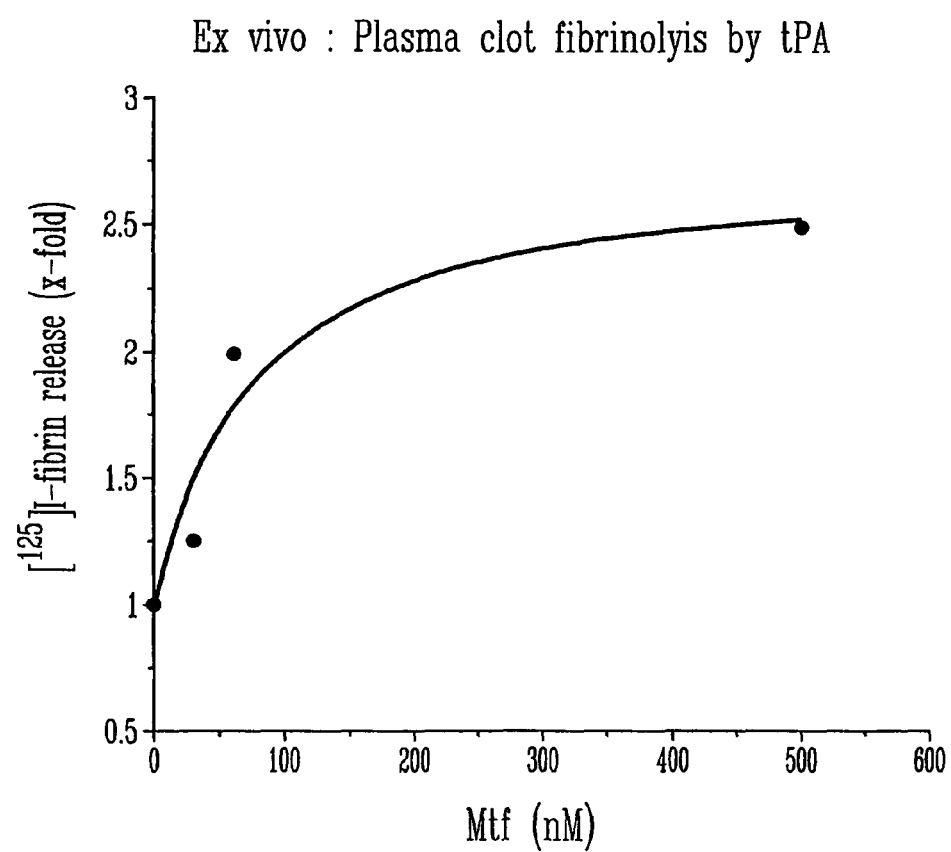
FIG. 25 illustrates the effects of p97 on plasma clot fibrinolysis by tPA.

The impact of soluble p97 on clot fibrinolysis by tPA was also measured ex vivo (FIG. 25). The addition of soluble p97 increases by 2.5-fold the action of tPA. In FIG. 25, the fibrinolytic activity of tPA (1 nM) on plasma clot fibrinolysis was measured ex vivo in the presence of increasing concentrations of p97.

In the blood coagulation system, the tissue-type plasminogen activator (tPA) is associated with fibrinolysis. tPA, mainly express by endothelial cells, cleaves the circulating plasminogen to the active proteinase plasmin which is the major enzyme responsible for the proteolytic degradation of the fibrin fiber. Currently, tPA is a stroke therapy which efficacy may be limited by neurotoxic side effects. Since soluble p97 potentialize plasminogen activation by tPA, the impact of soluble p97 on clot formation and lysis by thromboelastography analysis (TEG) has been evaluated using first an artificial fibrin-clot model (FIG. 26A). This model allowed to monitor the effect of soluble p97 on tPA-fibrinolysis in the absence of plasmin inhibitor. The fibrin clot is formed by the action of thrombin on fibrinogen and this clot also contains glu-plasminogen (2 µM). In FIG. 26, representative tracing showing effects of p97 (1 uM) on the fibrinolysis of clot formation under shear by TEG. In FIG. 26A illustrates a thrombelastogram of the fibrin clot model and FIG. 26B illustrates a Thromboelastogram of plasma recalcified after addition of 2 mM $CaCl_2$. The results shown here are representative of 3 experiments. The monitoring of the TEG parameters indicates that the addition of soluble p97 increases the thrombolytic activity of tPA (Table 4). In particular, when soluble p97 (1 µM) is added to tPA, the lysis of the clot after 30 min (LY30) after its complete formation is 5 times higher whereas the complete lysis time (CLT) is 50% shorter. The impact of soluble p97 on fibrin-clot dissolution using human citrated plasma (FIG. 26B) was further evaluated. For these analysis, $CaCl_2$ is added to initiate the polymerisation of plasma clot. The TEG parameters obtained for these experiments (Table 4) indicate that the addition of soluble p97 to tPA causes a 30% decrease in the clot strength (G), increases twice the fibrinolysis rate and reduces the CLT by 20%.

TABLE 4

Effects of p97 on thromboelastograph parameters

| Parameters | | Conditions | |
|---|---|---|---|
| | | tPA | tPA+ |
| a. Artificial fibrin-clot | | | |
| 1. G | d/sc | 498 ± 7 | 446 ± 17 |
| 2. Lys (30) | % | 6.5 | 31.9 |
| 3. CLT | min | 54.7 | 30.3 |
| b. Fibrin-clot with citrate-treated serum | | | |
| 1. G | d/sc | 13465 ± 1586 | 9560 ± 1626 |
| 2. Lys (30) | % | 4.3 ± 0.7 | 11.8 ± 4.0 |
| 3. CLT | min | 68.3 ± 1.6 | 49.1 ± 6.3 |

G (d/sc) is the maximum strength of the clot at maximum amplitude of the TEG trace.

The present findings are significant for several reasons. First, it was discovered that soluble p97, by interacting with plasminogen, enhances its activation by tPA. Furthermore, it is established that protein-protein interaction could positively regulate the activity of an enzyme by inducing a conformational change which lead to the exposure of active cryptic site. In addition, the data presented here in the radial clot lysis assay and the TEG analysis provide further evidence that soluble p97 positively regulates the tPA-dependent fibrinolysis by mainly decreasing the clot strength and time of lysis. Overall, the data indicate that soluble p97 increases the efficacy of the anti-thrombolysis agent tPA.

Second, perforation of the clot by soluble p97 without any release of fibrin fragments indicates that soluble p97 interaction with plasminogen induces a change in the fibrin-clot structure. Soluble p97 greatly facilitates the tPA action, leading to a localized and accelerated fibrinolysis.

In conclusion, the data presented herein indicates that human recombinant soluble p97 is as a switch activator of plasminogen since its interaction with plasminogen leads to an increase in the clot permeation and fibrinolysis by tPA. Thrombolysis with blood clot dissolving agent like tPA can reduced mortality in acute myocardial infraction.

Example IX

Inhibition of Angiogenesis by Melanotransferrin

During angiogenesis, cells must proliferate and migrate to finally invade the surrounding extracellular matrix (ECM). Moreover, metastasis is associated with tissue remodeling and invasion. In fact, when processing from migration to invasion, an additional complexity is added, as invasion comprises not only cell locomotion, but also the active penetration of cells into ECM.

Cell Culture

Cells were cultured under 5% $CO_2$/95% air atmosphere. Ovary hamster cells expressing or not the membrane type melanotransferrin (respectively mMTf-CHO and mock-CHO cells) were cultured with Ham F12 supplemented with 1 mM HEPES and 10% of calf serum (CS).

Cell Invasion Assay

Invasion was performed with CHO transfected with membrane bound Mtf (p97) (mMtf-CHO) or with the vector only (MOCK-CHO) using Transwell filters (Costar, Corning, N.Y.: 8 µm pore size) precoated with 50 µg Matrigel (BD Bioscience). The transwell filters were assembled in 24-well plates (Falcon 3097, Fisher Scientific, Montreal, Quebec, Canada) and the lower chambers filled with 600 µL cell culture medium containing 10% calf serum with or without 100 nM soluble p97 as well as 50 nM IgG1 or L235. To study the effect of soluble p97 and L235 on cell invasion, CHO cells were harvested by trypsinization and centrifuged. $1 \times 10^5$ cells were resuspended in 200 µL cell culture medium without serum and containing or not 100 nM soluble p97 as well as 50 nM IgG1 or L235 and added into the upper chamber of each Transwell. The plates were than placed at 37° C. in 5% $CO_2$/95% air for 48 hours. Cells that have invaded to the lower surface of the filters were fixed with 3.7% formaldehyde in PBS, stained with 0.1% crystal violet/20% MeOH, and count (4 random fields per filter) with Norten Eclipse digital software.

Transendothelial Invasion Assay

Mock-CHO and mMTf-CHO cells were seeded onto the <<blood brain barrier in vitro model>> at 100 000 cells/mL in presence of 5 mM Hoescht in supplemented Ham F12 medium with or without 50 nM of L235 (antibody directed against melanotranferrin). Cells were then incubated for 48 hours at 37° C. 5% $CO_2$. After the incubation, cells were fixed in 3.7% formaldehyde in phosphate-buffered saline (PBS, $Ca^{+2}/Mg^{+2}$ free) for 30 min and the plate were kept in the dark. The formaldehyde was then removed and cells that had migrated on the lower surface of the filter were then visualized with a Nikon Eclipse TE2000-U™ microscope-stage automatic thermocontrol system (Shizuoka-ken, Japan) at a 100× magnification using a Q IMAGING RETIGA™ camera, and counted with the program Northern Eclipse (Mississauga, Ontario).

Figure 27A:
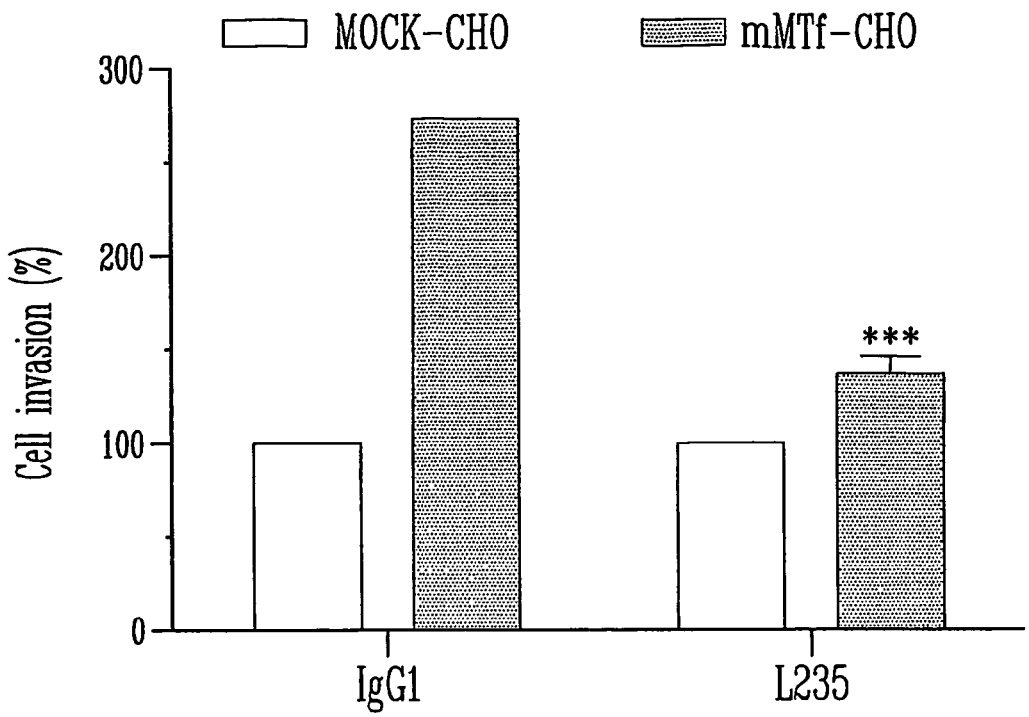
FIG. 27 illustrates that L235 (27A) and soluble p97 (27B) inhibited membrane bound p97-induced CHO cell invasion.
Figure 27B:
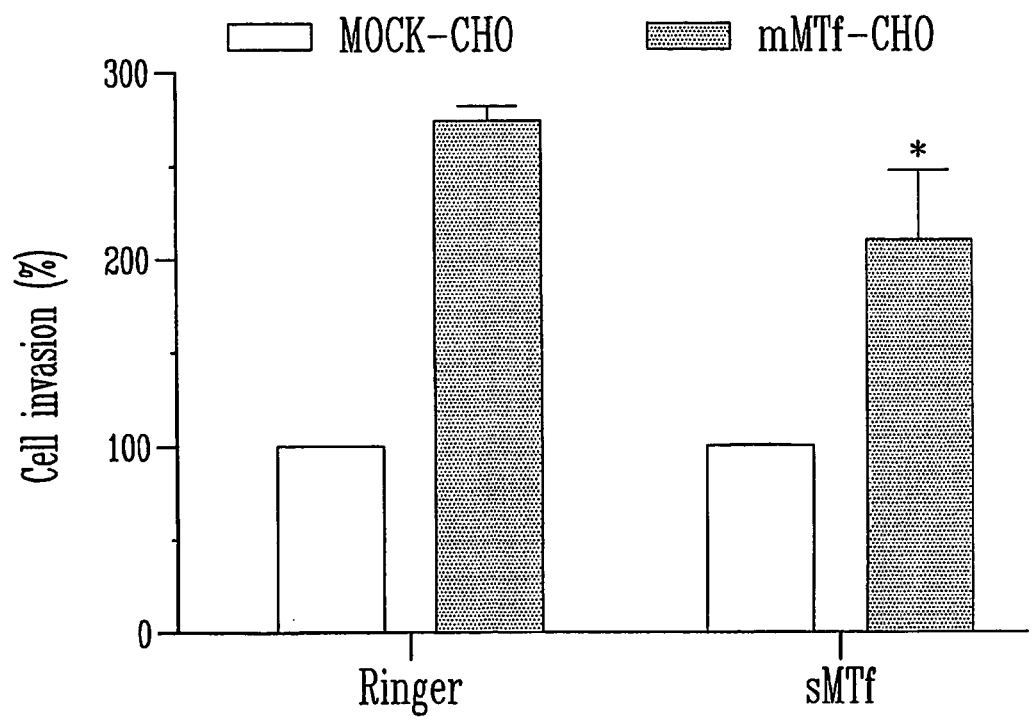

As can be seen on FIG. 27, these results suggest that endogenous membrane bound p97 stimulates CHO cell invasion. The invasion is inhibited by L235, indicating that membrane p97 participates directly in cell invasion. Moreover, recombinant soluble p97 could inhibit the invasion of these cells by competing with endogenous membrane bound p97.

In FIG. 27, cell invasion assay were performed as described in Material and Methods. Cell invasion assay was performed in presence of 50 nM L235 (27A) and 100 nM soluble p97 (27B). Data represents means±SDs. ***P <0.001, *P<0.05 (Student t test).

Transendothelial Invasion on the BBB In Vitro Model

Since soluble p97 affected plasminogen activation, the inventors investigated whether soluble p97 might modulate brain invasion. Using the blood-brain barrier (BBB) in vitro model, CHO cell invasion was examined. Following a 48 hours incubation, mMTf-CHO cells expressing the membrane associated melanotransferrin show a higher invasive character through the BBB model, comparatively to control cells (mock-CHO cells). Following the addition of L235, an antibody raised against the melanotransferrin, the invasive potential of membrane bound p97 transfected cells seem to be stopped, demonstrating a important role for endogenous membrane bound melanotransferrin in mechanisms leading to cell invasion. The results are illustrated in FIG. 28 In FIG. 28, cells that migrated were visualized by fluorescent microscopy and counted (4 random fields per filter) with Norten Eclipse digital software as described hereinabove.

Discussion

The data clearly show that both pro-uPA and plasminogen interact with p97 and that these interactions are specific since no interaction between p97 and other proteins including tPA, PAI-1, plasmin, angiostatin, BSA, or ovalbumin could be measured. These results are the first to describe potential interactions between p97 and proteins of the uPA system.

In addition to its interaction with pro-uPA and plasminogen, p97 stimulates plasminogen activation by decreasing the $K_m$ of pro-uPA for plasminogen and by increasing the $V_{max}$ of the reaction. The conversion of pro-uPA to two-chain uPA occurs by proteolytic cleavage of a single peptide bond (Lys158-Ile159 in human uPA). This conversion can be catalyzed by plasmin or several other proteases such as plasma kallikrein, blood coagulation factor XIIa, cathepsin B, cathepsin L and prostate-specific antigen. In the present invention the SPR assay, the enzymatic assay and electrophoresis experiments all indicate that p97 induces a conformational change that increases pro-uPA activity without any apparent cleavage of pro-uPA. The two-state conformational model gave the best fits for the interactions of both pro-uPA and plasminogen with immobilized p97 on the BIAcore. Such good fits of experimental data to a multi-state model of interaction are an indication that a conformational change is taking place. Interestingly, the fragments of plasminogen generated by adding p97 were different from the plasminogen degradation by pro-uPA alone. These biochemical analyses further suggest that p97 could also be seen as a cofactor in uPA-dependent plasminogen activation.

The uPA/uPAR system has been involved in several pathological and physiological processes which require cell migration, such as tumor cell invasion and metastasis. Several reports showed that the uPA/uPAR system plays a key role in signal transduction as well as in regulation of melanoma cell migration and angiogenesis. As shown in the present invention, when p97 is added to both compartments of the Boyden chamber migration of HMEC-1 is inhibited by more than 50%. Thus, given the important role of plasmin, a protein like p97 which targets the formation of plasmin and acts on the migration of endothelial cells as well as of SK-MEL28 cells will thus affect angiogenesis and cancer progression. It was also observed in the present invention that the basal capacity for plasminogen activation by HMEC-1 decreased following p97 treatment. A recent study demonstrated that the expression of LDL receptor-related protein 1B (LRP1B), a new member of the LDL receptor family, lead to an accumulation of uPAR on the cell surface which event inhibits the migration of CHO cells. From these results, it was proposed that LRP1B negatively regulates uPAR regeneration and function whereas the net results of uPAR regeneration, seems to depend on the relative expression of the two receptors.

Figure 29A:
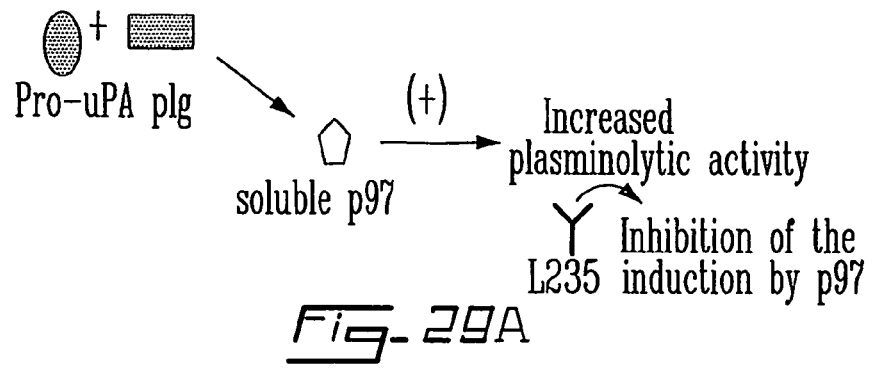
FIG. 29 illustrates that (29A) the interaction of pro-uPA and plasminogen with soluble p97 increases the activation of plasminogen; this induction can be inhibited by the mAb L235 which recognizes a conformational epitope on p97; (29B) the addition of mAb L235 reduces the plasminolytic activity on HMEC-1 cell surfaces and results in an inhibition of cell migration and (29C) the interaction of plasminogen and pro-uPA with membrane-bound p97 is diminished when exogenous, competing human recombinant p97 is added, which also results in a decrease in the activation of plasminogen and leads to an inhibition of cell migration.
Figure 29B:
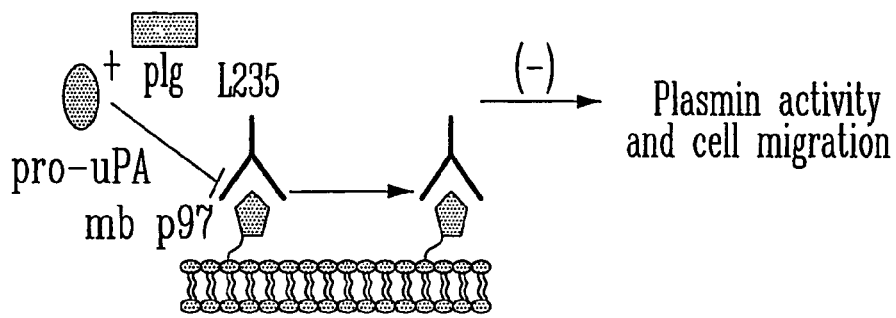
Figure 29C:
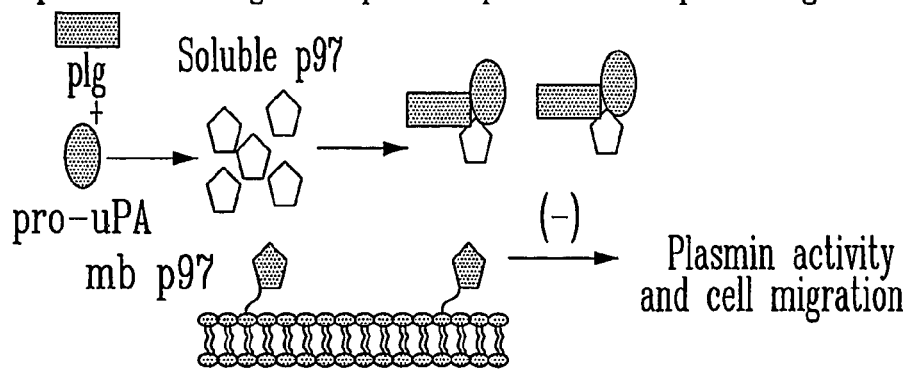

Recently, it was shown that when glu-plasminogen is bound to cell surfaces, plasmin generation by plasminogen activators is markedly stimulated compared to the reaction in solution. This is a key element for cell migration where the process of "grip and go" would play an important role. The process of plasminogen activation system is regulated by two different mechanisms: 1) cell surface-binding sites which facilitate the productive catalytic interactions with plasminogen and thereby increases plasmin generation, and 2) protein inhibitors such as serpin inhibitors which restrict the activities of the proteases. In light of this, soluble p97 participates in the activation of plasminogen without being in the pericellular environment (FIG. 29A). The present invention also indicates that the migration and the plasminolytic activity of cells expressing p97, are inhibited by mAb L235, indicating that eridogenous, membrane-bound p97 are involved in these processes which are associated with cancer and angiogenesis (FIG. 29B). Moreover, both the migration of HMEC-1 and the plasminolytic activity are diminished when exogenous p97 is added, indicating that soluble p97 affects the regulation of plasminogen activation at the cell surface (FIG. 29C). Thus, by breaking the equilibrium between soluble p97 and membrane bound p97, it is possible to affect cell migration of HMEC-1 and SK-MEL28 cells.

In conclusion, these are the first results indicating that p97 interacts with pro-uPA as well as with plasminogen and regulates the activation of plasminogen by pro-uPA. As shown in the present invention migration of HMEC-1 and SK-MEL28 cells is inhibited by mAb L235 and soluble p97, indicating that active and functional p97 participates in this process. Collectively, the results thus indicate that the balance between membrane-bound and soluble p97 could affect cell migration.

As mentioned above, these are the first data indicating that exogenous human recombinant soluble p97 have anti-angiogenic properties, by affecting the morphogenic differentiation of EC into capillary-like structures, by interfering with key proteins involved in angiogenesis and by inducing EC detachment.

Also as mentioned previously, the data presented herein indicates that human recombinant soluble p97 can be seen as a switch activator of plasminogen since its interaction with plasminogen leads to an increase in the clot permeation and fibrinolysis by tPA. Thrombolysis with blood clot dissolving agent like tPA can reduced mortality in acute myocardial infraction. However, damage can occur since the blow flow is restored by only 60% after 90 min. The results presented herein suggest that soluble p97 could increase the efficiency of the thrombolytic agent (tPA) when co-administrated, Furthermore, since the reoccluded clots are usually more resistant to tPA, soluble p97 administration could counter this adverse effect by increasing the therapeutic window of tPA. According to the American Heart Association, two million Americans suffer from atrial fibrillation, in which the two small upper chambers of the heart quiver instead of beating effectively. Blood in these quivering chambers can clot, travel and obstruct blood circulation. This phenomenon can also happen in the vein, where the clot would obstruct as well. Soluble p97 would enhance tPA effectiveness and broaden its therapeutic window. P97 has also the power to modify clot structure. Moreover, p97-containing gel could also be used to control new blood vessel growth and to reduce the need for coronary bypass surgery and provide effective treatment for a debilitating cardiovascular disease.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for treating cancer caused by cells expressing melanotransferrin (p97) at their surface, said method comprising the step of administering to a patient in need thereof exogenous soluble p97 or active fragment thereof, said soluble p97 or active fragment thereof being unconjugated to any moiety and competing with the p97 expressed on the cell surface, activating plasminogen in solution instead of membrane-bound plasminogen, thus preventing cell migration and preventing cancer cells from spreading.

2. The method of claim 1, wherein said cell is a tumor cell.

3. The method of claim 1, wherein said cell is selected from the group consisting of human vascular or microvascular endothelial cells and human melanoma cells.

4. A method of treating cancer, comprising administering to an individual a therapeutically effective amount of a pharmaceutical composition comprising one of melanotransferrin (p97) or an active fragment thereof, said melanotransferrin or fragment thereof being unconjugated to any moiety, in association with a pharmaceutically acceptable carrier.

5. The method according to claim 4, wherein said administering is carried out orally, parenterally, subcutaneously, intravenously, intramuscularly, intraperitoneally, intraarterially, transdermally or via a mucus membrane.

6. The method according to claim 4, wherein said cancer is selected from the group consisting of melanoma, prostate cancer, leukemia, hormone dependent cancer, breast cancer, colon cancer, lung cancer, skin cancer, ovarian cancer, pancreatic cancer, bone cancer, liver cancer, biliary cancer, urinary organ cancer (for example, bladder, testis), lymphoma, retinoblastoma, sarcoma, epidermal cancer, esophageal cancer, stomach cancer, cancer of the brain, cancer of the kidney, and metastasis thereof.

7. A method for inhibiting metastasis caused by cells expressing melanotransferrin (p97) at their surface, said method comprising the step of administering to a patient in need thereof exogenous soluble p97 or active fragment thereof, said soluble p97 or active fragment thereof being unconjugated to any moiety and competing with the p97 expressed on the cell surface, activating plasminogen in solution instead of membrane-bound plasminogen, thus preventing cell migration and preventing cancer cells from spreading.

* * * * *

SEQUENCE LISTING

<160> NUMBER OF SEQ ID NOS: 19

<210> SEQ ID NO 1
<211> LENGTH: 738
<212> TYPE: PRT
<213> ORGANISM: Homo Sapiens

<400> SEQUENCE: 1

```
Met Arg Gly Pro Ser Gly Ala Leu Trp Leu Leu Ala Leu Arg Thr
  1               5                  10                  15

Val Leu Gly Gly Met Glu Val Arg Trp Cys Ala Thr Ser Asp Pro Glu
                 20                  25                  30

Gln His Lys Cys Gly Asn Met Ser Glu Ala Phe Arg Glu Ala Gly Ile
             35                  40                  45

Gln Pro Ser Leu Leu Cys Val Arg Gly Thr Ser Ala Asp His Cys Val
         50                  55                  60

Gln Leu Ile Ala Ala Gln Glu Ala Asp Ala Ile Thr Leu Asp Gly Gly
 65                  70                  75                  80

Ala Ile Tyr Glu Ala Gly Lys Glu His Gly Leu Lys Pro Val Val Gly
                 85                  90                  95

Glu Val Tyr Asp Gln Glu Val Gly Thr Ser Tyr Tyr Ala Val Ala Val
                100                 105                 110

Val Arg Arg Ser Ser His Val Thr Ile Asp Thr Leu Lys Gly Val Lys
            115                 120                 125

Ser Cys His Thr Gly Ile Asn Arg Thr Val Gly Trp Asn Val Pro Val
130                 135                 140

Gly Tyr Leu Val Glu Ser Gly Arg Leu Ser Val Met Gly Cys Asp Val
145                 150                 155                 160

Leu Lys Ala Val Ser Asp Tyr Phe Gly Gly Ser Cys Val Pro Gly Ala
                165                 170                 175

Gly Glu Thr Ser Tyr Ser Glu Ser Leu Cys Arg Leu Cys Arg Gly Asp
                180                 185                 190

Ser Ser Gly Glu Gly Val Cys Asp Lys Ser Pro Leu Glu Arg Tyr Tyr
            195                 200                 205

Asp Tyr Ser Gly Ala Phe Arg Cys Leu Ala Glu Gly Ala Gly Asp Val
    210                 215                 220

Ala Phe Val Lys His Ser Thr Val Leu Glu Asn Thr Asp Gly Lys Thr
225                 230                 235                 240

Leu Pro Ser Trp Gly Gln Ala Leu Leu Ser Gln Asp Phe Glu Leu Leu
                245                 250                 255

Cys Arg Asp Gly Ser Arg Ala Asp Val Thr Glu Trp Arg Gln Cys His
                260                 265                 270

Leu Ala Arg Val Pro Ala His Ala Val Val Arg Ala Asp Thr Asp
            275                 280                 285

Gly Gly Leu Ile Phe Arg Leu Leu Asn Glu Gly Gln Arg Leu Phe Ser
    290                 295                 300

His Glu Gly Ser Ser Phe Gln Met Phe Ser Ser Glu Ala Tyr Gly Gln
305                 310                 315                 320

Lys Asp Leu Leu Phe Lys Asp Ser Thr Ser Glu Leu Val Pro Ile Ala
                325                 330                 335

Thr Gln Thr Tyr Glu Ala Trp Leu Gly His Glu Tyr Leu His Ala Met
            340                 345                 350

Lys Gly Leu Leu Cys Asp Pro Asn Arg Leu Pro Pro Tyr Leu Arg Trp
        355                 360                 365
```

Cys Val Leu Ser Thr Pro Glu Ile Gln Lys Cys Gly Asp Met Ala Val
        370                 375                 380

Ala Phe Arg Arg Gln Arg Leu Lys Pro Glu Ile Gln Cys Val Ser Ala
385                 390                 395                 400

Lys Ser Pro Gln His Cys Met Glu Arg Ile Gln Ala Glu Gln Val Asp
                405                 410                 415

Ala Val Thr Leu Ser Gly Glu Asp Ile Tyr Thr Ala Gly Lys Lys Tyr
            420                 425                 430

Gly Leu Val Pro Ala Ala Gly Glu His Tyr Ala Pro Glu Asp Ser Ser
        435                 440                 445

Asn Ser Tyr Tyr Val Val Ala Val Val Arg Arg Asp Ser Ser His Ala
    450                 455                 460

Phe Thr Leu Asp Glu Leu Arg Gly Lys Arg Ser Cys His Ala Gly Phe
465                 470                 475                 480

Gly Ser Pro Ala Gly Trp Asp Val Pro Val Gly Ala Leu Ile Gln Arg
                485                 490                 495

Gly Phe Ile Arg Pro Lys Asp Cys Asp Val Leu Thr Ala Val Ser Glu
            500                 505                 510

Phe Phe Asn Ala Ser Cys Val Pro Val Asn Asn Pro Lys Asn Tyr Pro
        515                 520                 525

Ser Ser Leu Cys Ala Leu Cys Val Gly Asp Glu Gln Gly Arg Asn Lys
    530                 535                 540

Cys Val Gly Asn Ser Gln Glu Arg Tyr Gly Tyr Arg Gly Ala Phe
545                 550                 555                 560

Arg Cys Leu Val Glu Asn Ala Gly Asp Val Ala Phe Val Arg His Thr
                565                 570                 575

Thr Val Phe Asp Asn Thr Asn Gly His Asn Ser Glu Pro Trp Ala Ala
            580                 585                 590

Glu Leu Arg Ser Glu Asp Tyr Glu Leu Leu Cys Pro Asn Gly Ala Arg
        595                 600                 605

Ala Glu Val Ser Gln Phe Ala Ala Cys Asn Leu Ala Gln Ile Pro Pro
    610                 615                 620

His Ala Val Met Val Arg Pro Asp Thr Asn Ile Phe Thr Val Tyr Gly
625                 630                 635                 640

Leu Leu Asp Lys Ala Gln Asp Leu Phe Gly Asp Asp His Asn Lys Asn
                645                 650                 655

Gly Phe Lys Met Phe Asp Ser Ser Asn Tyr His Gly Gln Asp Leu Leu
            660                 665                 670

Phe Lys Asp Ala Thr Val Arg Ala Val Pro Val Gly Glu Lys Thr Thr
        675                 680                 685

Tyr Arg Gly Trp Leu Gly Leu Asp Tyr Val Ala Ala Leu Glu Gly Met
    690                 695                 700

Ser Ser Gln Gln Cys Ser Gly Ala Ala Ala Pro Ala Pro Gly Ala Pro
705                 710                 715                 720

Leu Leu Pro Leu Leu Leu Pro Ala Leu Ala Ala Arg Leu Leu Pro Pro
                725                 730                 735

Ala Leu

<210> SEQ ID NO 2
<211> LENGTH: 21
<212> TYPE: DNA
<213> ORGANISM: Artificial Sequence
<220> FEATURE:
<223> OTHER INFORMATION: primer sequence -continued

```
<400> SEQUENCE: 2
agaagtagca ggaccagagg g                                        21

<210> SEQ ID NO 3
<211> LENGTH: 21
<212> TYPE: DNA
<213> ORGANISM: Artificial Sequence
<220> FEATURE:
<223> OTHER INFORMATION: antisense primer sequence

<400> SEQUENCE: 3
tcagtaccca ggcagttatg c                                        21

<210> SEQ ID NO 4
<211> LENGTH: 22
<212> TYPE: DNA
<213> ORGANISM: Artificial Sequence
<220> FEATURE:
<223> OTHER INFORMATION: primer sequence

<400> SEQUENCE: 4
tctctccctt ctccaaagac cc                                       22

<210> SEQ ID NO 5
<211> LENGTH: 22
<212> TYPE: DNA
<213> ORGANISM: Artificial Sequence
<220> FEATURE:
<223> OTHER INFORMATION: antisense primer sequence

<400> SEQUENCE: 5
tcaatgagtc cagccagtca gc                                       22

<210> SEQ ID NO 6
<211> LENGTH: 22
<212> TYPE: DNA
<213> ORGANISM: Artificial Sequence
<220> FEATURE:
<223> OTHER INFORMATION: primer sequence

<400> SEQUENCE: 6
cggagcagtg tggcttattt tc                                       22

<210> SEQ ID NO 7
<211> LENGTH: 22
<212> TYPE: DNA
<213> ORGANISM: Artificial Sequence
<220> FEATURE:
<223> OTHER INFORMATION: antisense primer sequence

<400> SEQUENCE: 7
caggtgtatt gggtgtcaag gc                                       22

<210> SEQ ID NO 8
<211> LENGTH: 24
<212> TYPE: DNA
<213> ORGANISM: Artificial Sequence
<220> FEATURE:
<223> OTHER INFORMATION: primer sequence

<400> SEQUENCE: 8
ggacccaaca agttcaagtg tcac                                     24

<210> SEQ ID NO 9
<211> LENGTH: 22
<212> TYPE: DNA
```

```
<213> ORGANISM: Artificial Sequence
<220> FEATURE:
<223> OTHER INFORMATION: antisense primer sequence

<400> SEQUENCE: 9
aagaagaggt aggcgatgga gc                                           22

<210> SEQ ID NO 10
<211> LENGTH: 25
<212> TYPE: DNA
<213> ORGANISM: Artificial Sequence
<220> FEATURE:
<223> OTHER INFORMATION: primer sequence

<400> SEQUENCE: 10
ccttgaagat gatggactac cctcg                                        25

<210> SEQ ID NO 11
<211> LENGTH: 24
<212> TYPE: DNA
<213> ORGANISM: Artificial Sequence
<220> FEATURE:
<223> OTHER INFORMATION: antisense primer sequence

<400> SEQUENCE: 11
aaaacccaaa aaagcccccc cagc                                         24

<210> SEQ ID NO 12
<211> LENGTH: 24
<212> TYPE: DNA
<213> ORGANISM: Artificial Sequence
<220> FEATURE:
<223> OTHER INFORMATION: primer sequence

<400> SEQUENCE: 12
accgaggttg tgtgtgggtt agac                                         24

<210> SEQ ID NO 13
<211> LENGTH: 22
<212> TYPE: DNA
<213> ORGANISM: Artificial Sequence
<220> FEATURE:
<223> OTHER INFORMATION: antisense primer sequence

<400> SEQUENCE: 13
caggaagtgg aaggtgtcgt tg                                           22

<210> SEQ ID NO 14
<211> LENGTH: 20
<212> TYPE: DNA
<213> ORGANISM: Artificial Sequence
<220> FEATURE:
<223> OTHER INFORMATION: primer sequence

<400> SEQUENCE: 14
ccatcaccat cttccaggag                                              20

<210> SEQ ID NO 15
<211> LENGTH: 20
<212> TYPE: DNA
<213> ORGANISM: Artificial Sequence
<220> FEATURE:
<223> OTHER INFORMATION: antisense primer sequence

<400> SEQUENCE: 15
cctgcttcac caccttcttg                                              20
```

```
<210> SEQ ID NO 16
<211> LENGTH: 24
<212> TYPE: DNA
<213> ORGANISM: Artificial Sequence
<220> FEATURE:
<223> OTHER INFORMATION: primer sequence

<400> SEQUENCE: 16
aaagacattg cgtggtcagg cagc                                          24

<210> SEQ ID NO 17
<211> LENGTH: 23
<212> TYPE: DNA
<213> ORGANISM: Artificial Sequence
<220> FEATURE:
<223> OTHER INFORMATION: antisense primer sequence

<400> SEQUENCE: 17
ggcatcataa ggcagtcgtt cac                                           23

<210> SEQ ID NO 18
<211> LENGTH: 24
<212> TYPE: DNA
<213> ORGANISM: Artificial Sequence
<220> FEATURE:
<223> OTHER INFORMATION: primer sequence

<400> SEQUENCE: 18
ccagcacata ggagagatga gctt                                          24

<210> SEQ ID NO 19
<211> LENGTH: 24
<212> TYPE: DNA
<213> ORGANISM: Artificial Sequence
<220> FEATURE:
<223> OTHER INFORMATION: antisense primer sequence

<400> SEQUENCE: 19
ggtgtggtgg tgacatggtt aatc                                          24
```